(12) United States Patent
Catlin et al.

(10) Patent No.: US 11,679,648 B2
(45) Date of Patent: Jun. 20, 2023

(54) VEHICLE INTERIOR COMPONENT

(71) Applicant: Shanghai Yanfeng Jinqiao Automotive Trim Systems Co. Ltd., Novi, MI (US)

(72) Inventors: Michael Robert Catlin, Holland, MI (US); Thomas Scott Hodgson, Holland, MI (US); Shane M. Vorac, Caledonia, MI (US); Weining Song, Novi, MI (US); Xiaohui Pan, Novi, MI (US); Xinqing Zhu, Novi, MI (US)

(73) Assignee: Shanghai Yanfeng Jinqiao Automotive Trim Systems Co. Ltd., Novi, MI (US)

( * ) Notice: Subject to any disclaimer, the term of this patent is extended or adjusted under 35 U.S.C. 154(b) by 0 days.

(21) Appl. No.: 17/463,496

(22) Filed: Aug. 31, 2021

(65) Prior Publication Data

US 2021/0394589 A1    Dec. 23, 2021

Related U.S. Application Data

(63) Continuation of application No. PCT/US2020/023133, filed on Mar. 17, 2020.
(Continued)

(51) Int. Cl.
*B60H 3/00* (2006.01)
(52) U.S. Cl.
CPC ... *B60H 3/0007* (2013.01); *B60H 2003/0042* (2013.01); *B60H 2003/0057* (2013.01)
(58) Field of Classification Search
CPC .... B60H 2003/0042; B60H 2003/0057; B60H 3/0007
(Continued)

(56) References Cited

U.S. PATENT DOCUMENTS

| 4,035,451 A | 7/1977 | Tringali |
| 5,011,074 A | 4/1991 | Kline |
| (Continued) | | |

FOREIGN PATENT DOCUMENTS

| CN | 203802845 U | 9/2014 |
| CN | 204033844 U | 12/2014 |
| (Continued) | | |

OTHER PUBLICATIONS

EP2143575_translation (Year: 2010).*
(Continued)

*Primary Examiner* — Nathaniel E Wiehe
*Assistant Examiner* — Ket D Dang
(74) *Attorney, Agent, or Firm* — Amin, Turocy & Watson, LLP

(57) ABSTRACT

A component for a vehicle interior configured to dispense scent in a vehicle interior is disclosed. The component may comprise a scent-dispensing apparatus comprising a module configured for at least one scent-dispensing cartridge (removable/replaceable) containing scent media. An actuator may be configured to operate the module in a bypass mode or for selection/actuation of a cartridge. A selected cartridge may be actuated from a sealed state to prevent airflow through scent media to an unsealed state to allow airflow across/through scent media and into the vehicle interior. The actuator may comprise a mechanism (e.g. slider, cam mechanism); each cartridge may comprise a valve mechanism actuated by the actuator; each mechanism may comprise a spring. The module may comprise a fan to provide airflow. The component may provide a user interface. The component may comprise a console, overhead console, floor console, center console, etc.

20 Claims, 36 Drawing Sheets

Related U.S. Application Data

(60) Provisional application No. 62/927,768, filed on Oct. 30, 2019, provisional application No. 62/842,872, filed on May 3, 2019, provisional application No. 62/835,210, filed on Apr. 17, 2019, provisional application No. 62/820,082, filed on Mar. 18, 2019.

(58) Field of Classification Search
USPC .... 422/123, 124; 261/30, 115, 26, 141, 142, 261/DIG. 17, DIG. 65, DIG. 88, DIG. 89; 96/222
See application file for complete search history.

(56) References Cited

U.S. PATENT DOCUMENTS

| | | |
|---|---|---|
| 6,371,451 B1 | 4/2002 | Choi |
| D459,950 S | 7/2002 | Bush et al. |
| 6,581,915 B2 | 6/2003 | Bartsch et al. |
| 6,619,559 B2 | 9/2003 | Wohrle |
| 6,744,488 B2 | 6/2004 | Schermerhorn |
| 6,783,117 B2 | 8/2004 | Wohrle |
| 6,834,847 B2 | 12/2004 | Bartsch et al. |
| 7,185,360 B1 | 2/2007 | Anton, Jr. et al. |
| 7,344,123 B2 | 3/2008 | Pankhurst et al. |
| 7,601,297 B2 | 10/2009 | Gygax et al. |
| 7,708,256 B2 | 5/2010 | Pankhurst et al. |
| 7,712,683 B2 | 5/2010 | Robert et al. |
| 7,734,123 B2 | 6/2010 | Bar et al. |
| 7,734,159 B2 | 6/2010 | Beland et al. |
| 7,748,687 B2 | 7/2010 | Pankhurst et al. |
| 7,841,587 B2 | 11/2010 | Pankhurst et al. |
| 7,926,792 B2 | 4/2011 | Pankhurst et al. |
| 8,074,970 B2 | 12/2011 | Pankhurst et al. |
| 8,170,405 B2 | 5/2012 | Harris |
| 8,196,902 B1 | 6/2012 | Pystin |
| 8,255,089 B2 | 8/2012 | Luc et al. |
| 8,385,730 B2 | 2/2013 | Bushman et al. |
| 8,565,926 B2 | 10/2013 | Luc et al. |
| 8,603,963 B1 | 12/2013 | Steward et al. |
| 8,632,059 B2 | 1/2014 | Pankhurst et al. |
| 8,857,735 B2 | 10/2014 | Rosener et al. |
| 8,868,245 B2 | 10/2014 | Luc et al. |
| 8,897,629 B1 | 11/2014 | Deacon |
| 8,939,386 B2 | 1/2015 | Robert et al. |
| 9,233,387 B2 | 1/2016 | Fehling |
| 9,308,287 B2 | 4/2016 | Wolf et al. |
| 9,446,161 B1 | 9/2016 | Steward et al. |
| 9,446,162 B2 | 9/2016 | Chandler et al. |
| 9,460,404 B2 | 10/2016 | Chandler et al. |
| 9,474,820 B2 | 10/2016 | Rosener et al. |
| 9,539,354 B2 | 1/2017 | Rappel et al. |
| 9,586,228 B2 | 3/2017 | Roemburg et al. |
| 9,610,827 B2 | 4/2017 | Hafner |
| 9,715,223 B2 | 7/2017 | Chandler et al. |
| 9,808,550 B2 | 11/2017 | Fantuzzi et al. |
| 9,823,263 B2 * | 11/2017 | Accurso .................. G01N 1/28 |
| 9,833,532 B1 | 12/2017 | Steward et al. |
| 9,855,824 B2 | 1/2018 | Stiehler et al. |
| 9,884,298 B2 | 2/2018 | Rosener et al. |
| 9,919,070 B2 | 3/2018 | Rappel |
| 9,927,789 B2 | 3/2018 | Chandler et al. |
| 9,931,425 B2 | 4/2018 | Edwards et al. |
| 10,058,627 B2 | 8/2018 | Kelsen |
| 10,067,377 B2 | 9/2018 | Wang et al. |
| 10,073,430 B2 | 9/2018 | Chandler et al. |
| 10,143,768 B2 | 12/2018 | Roemburg et al. |
| 10,179,184 B2 | 1/2019 | Belz et al. |
| 10,258,711 B2 | 4/2019 | Robert et al. |
| 10,287,021 B2 | 5/2019 | Fantuzzi et al. |
| 10,328,169 B2 | 6/2019 | Marschall et al. |
| 10,534,339 B2 | 1/2020 | Chandler et al. |
| 10,556,034 B2 | 2/2020 | Jin et al. |
| 10,661,636 B2 | 5/2020 | Bauer et al. |
| 10,675,595 B2 | 6/2020 | Rosener et al. |
| 10,775,759 B2 | 9/2020 | Chandler et al. |
| 10,838,388 B2 | 11/2020 | Chandler et al. |
| 2002/0058595 A1 | 5/2002 | Kaiser |
| 2002/0066798 A1 | 6/2002 | Laudamiel-Pellet et al. |
| 2002/0068009 A1 | 6/2002 | Laudamiel-Pellet et al. |
| 2002/0068010 A1 | 6/2002 | Laudamiel-Pellet et al. |
| 2003/0107139 A1 | 6/2003 | Wohrle |
| 2003/0206834 A1 | 11/2003 | Chiao et al. |
| 2004/0028551 A1 | 2/2004 | Kvietok et al. |
| 2004/0033171 A1 | 2/2004 | Kvietok et al. |
| 2005/0147523 A1 | 7/2005 | Laudamiel-Pellet et al. |
| 2005/0147539 A1 | 7/2005 | Laudamiel-Pellet et al. |
| 2005/0167860 A1 | 8/2005 | Brooks |
| 2006/0067859 A1 | 3/2006 | Laudamiel-Pellet et al. |
| 2007/0124802 A1 | 5/2007 | Anton et al. |
| 2008/0191370 A1 | 8/2008 | Pankhurst et al. |
| 2009/0008470 A1 * | 1/2009 | Feuillard .............. B60H 3/0007 239/57 |
| 2010/0243754 A1 * | 9/2010 | Harris ........................ A61L 9/14 239/34 |
| 2013/0277456 A1 * | 10/2013 | Fehling ..................... A61L 9/12 239/302 |
| 2014/0377130 A1 | 12/2014 | Edwards et al. |
| 2017/0065737 A1 * | 3/2017 | Rappel ................ B60H 3/0007 |
| 2017/0216474 A1 | 8/2017 | Kelsen |
| 2017/0253338 A1 * | 9/2017 | Fantuzzi .................. A61L 9/122 |
| 2017/0322535 A1 | 11/2017 | Chandler et al. |
| 2018/0071425 A1 | 3/2018 | Jin et al. |
| 2018/0169288 A1 | 6/2018 | Kelsen |
| 2018/0208024 A1 * | 7/2018 | Bauer ....................... A61L 9/12 |
| 2018/0280557 A1 | 10/2018 | Field et al. |
| 2018/0369442 A1 | 12/2018 | Kelsen |
| 2019/0070937 A1 | 3/2019 | Yoshimatsu |
| 2019/0184792 A1 * | 6/2019 | Watanabe ............ B60H 3/0035 |
| 2019/0339654 A1 | 11/2019 | Edwards et al. |
| 2020/0078485 A1 | 3/2020 | Suarez Iribarne et al. |
| 2020/0225629 A1 | 7/2020 | Chandler et al. |
| 2020/0324011 A1 | 10/2020 | Jin et al. |
| 2020/0368698 A1 | 11/2020 | Rosener et al. |

FOREIGN PATENT DOCUMENTS

| | | |
|---|---|---|
| CN | 204219450 U | 3/2015 |
| CN | 108873752 A | 11/2018 |
| CN | 208435196 U | 1/2019 |
| CN | 105476647 B | 8/2020 |
| DE | 102004017067 A1 | 10/2005 |
| DE | 102008013218 A1 | 9/2009 |
| DE | 102008021460 A1 | 11/2009 |
| DE | 102008033806 A1 | 11/2009 |
| DE | 102008033826 A1 | 1/2010 |
| DE | 102009032729 A1 | 2/2010 |
| DE | 102009006192 A1 | 7/2010 |
| DE | 102009006193 A1 | 8/2010 |
| DE | 102010008436 A1 | 8/2011 |
| DE | 102010011596 A1 | 11/2011 |
| DE | 102012009676 A1 | 10/2012 |
| DE | 102012016994 A1 | 3/2013 |
| DE | 102012021448 A1 | 5/2013 |
| DE | 202013003476 U1 | 5/2013 |
| DE | 202013003494 U1 | 5/2013 |
| DE | 202013003495 U1 | 5/2013 |
| DE | 102012211297 A1 | 1/2014 |
| DE | 202014102849 U1 | 7/2014 |
| DE | 102013006475 A1 | 10/2014 |
| DE | 102014006925 A1 | 12/2014 |
| DE | 102014202561 A1 | 8/2015 |
| DE | 102014203195 A1 | 8/2015 |
| DE | 102014214167 A1 | 1/2016 |
| DE | 102011116897 B4 | 5/2016 |
| DE | 102013012022 B4 | 5/2016 |
| DE | 102014227015 A1 | 6/2016 |
| DE | 102015015972 A1 | 6/2017 |
| DE | 102017204895 A1 | 9/2018 |
| DE | 102017206214 A1 | 10/2018 |
| DE | 102008011174 B4 | 6/2020 |
| DE | 102015001196 B4 | 8/2020 |
| EP | 1303315 A1 | 4/2003 |
| EP | 1303316 A2 | 4/2003 |
| EP | 1543844 A3 | 8/2005 |

(56) References Cited

FOREIGN PATENT DOCUMENTS

| | | | | |
|---|---|---|---|---|
| EP | 1523340 B1 | 4/2006 | | |
| EP | 1303317 B1 | 9/2006 | | |
| EP | 1303318 B1 | 9/2006 | | |
| EP | 1303319 B1 | 9/2006 | | |
| EP | 2143575 A1 * | 1/2010 | ............... | A61L 9/03 |
| EP | 2143575 A1 | 1/2010 | | |
| EP | 2145788 B1 | 1/2010 | | |
| EP | 1961594 B1 | 8/2011 | | |
| EP | 2455108 B1 | 5/2012 | | |
| EP | 2143576 B1 | 11/2012 | | |
| EP | 1432456 B1 | 12/2012 | | |
| EP | 2541620 A1 | 1/2013 | | |
| EP | 2575904 A1 | 4/2013 | | |
| EP | 2142034 B1 | 10/2013 | | |
| EP | 2095980 B1 | 11/2013 | | |
| EP | 2670446 B1 | 12/2013 | | |
| EP | 2143577 B1 | 9/2014 | | |
| EP | 2269850 B1 | 10/2014 | | |
| EP | 2641620 B1 | 6/2015 | | |
| EP | 2968637 A2 | 1/2016 | | |
| EP | 2968638 A2 | 1/2016 | | |
| EP | 3022075 B1 | 3/2017 | | |
| EP | 2749440 B1 | 5/2017 | | |
| EP | 2769862 B1 | 8/2017 | | |
| EP | 2841208 B1 | 2/2018 | | |
| EP | 3280541 A1 | 2/2018 | | |
| EP | 3002142 B1 * | 8/2018 | ............... | A61L 2/00 |
| EP | 2455107 B1 | 2/2019 | | |
| EP | 3019917 B1 | 2/2019 | | |
| EP | 3019918 B1 | 4/2019 | | |
| EP | 3092139 B1 | 6/2019 | | |
| EP | 2903842 B1 | 2/2020 | | |
| GB | 2233230 B | 7/1992 | | |
| GB | 2560571 A | 9/2018 | | |
| KR | 20130000134 A * | 1/2013 | ............... | F24F 3/16 |
| WO | 2002/09776 A2 | 2/2002 | | |
| WO | 2002/09779 A1 | 2/2002 | | |
| WO | 0232472 A1 | 4/2002 | | |
| WO | 2005100063 A1 | 10/2005 | | |
| WO | 2011/149540 A1 | 12/2011 | | |
| WO | 2013/050134 A1 | 4/2013 | | |
| WO | 2014016533 A1 | 1/2014 | | |
| WO | 2014/144636 A2 | 9/2014 | | |
| WO | 2014/144690 A2 | 9/2014 | | |
| WO | 2016/164917 A1 | 10/2016 | | |
| WO | 2019057643 A2 | 3/2019 | | |
| WO | 2020/021076 A1 | 1/2020 | | |

OTHER PUBLICATIONS

17463496_2022-06-06_EP_3002142_B1_M.pdf (Year: 2015).*
17463496_2022-07-13_KR_20130000134_A_M.pdf (Year: 2013).*
International Search Report and Written Opinion received for PCT Application Serial No. PCT/US2020/23133 dated Aug. 14, 2020, 18 pages.
Extended European Search Report received for EP Application Serial No. 20774853.4 dated Nov. 15, 2022, 7 pages.
Office Action received for Chinese Patent Application Serial No. 202080013248.5 dated Jan. 12, 2023, 16 pages (Original Copy only).

* cited by examiner

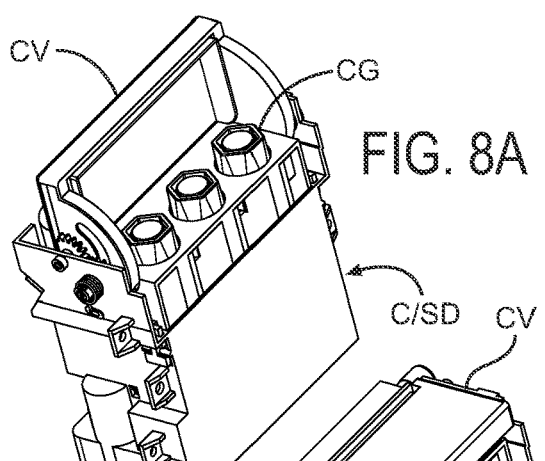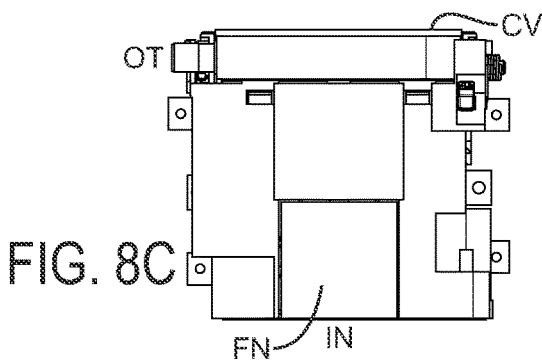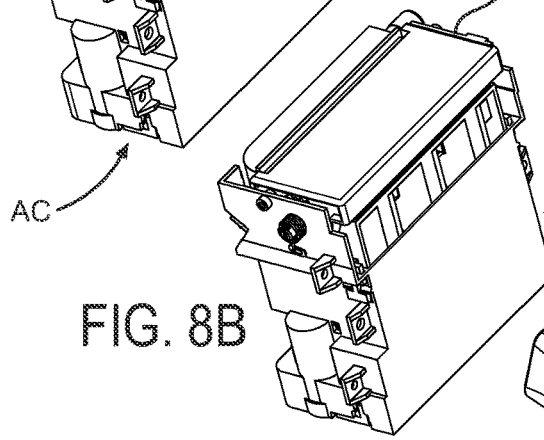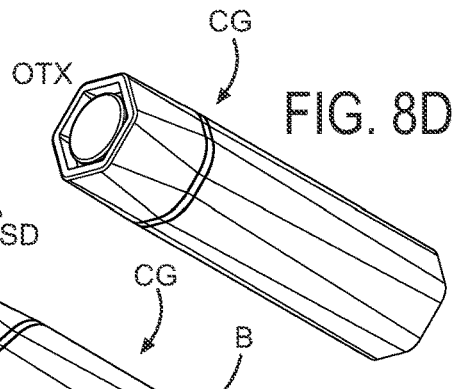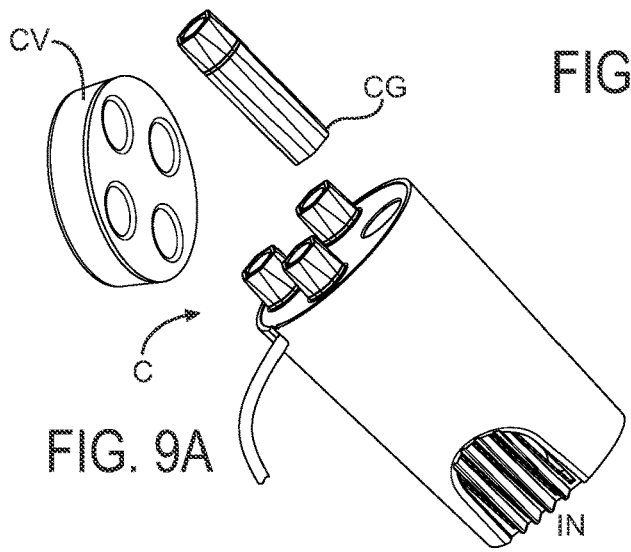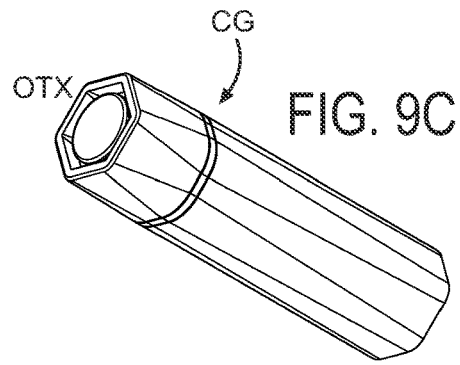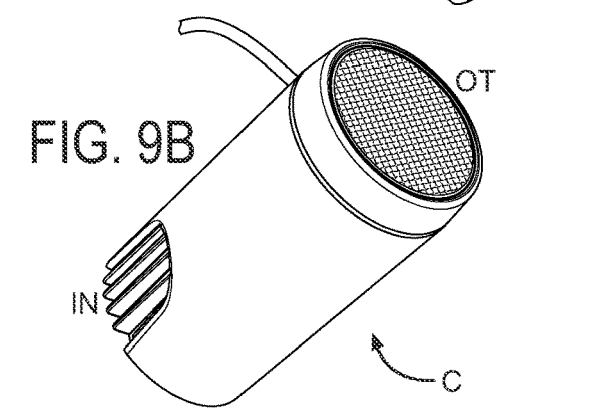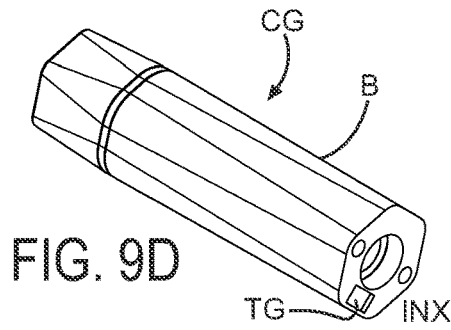

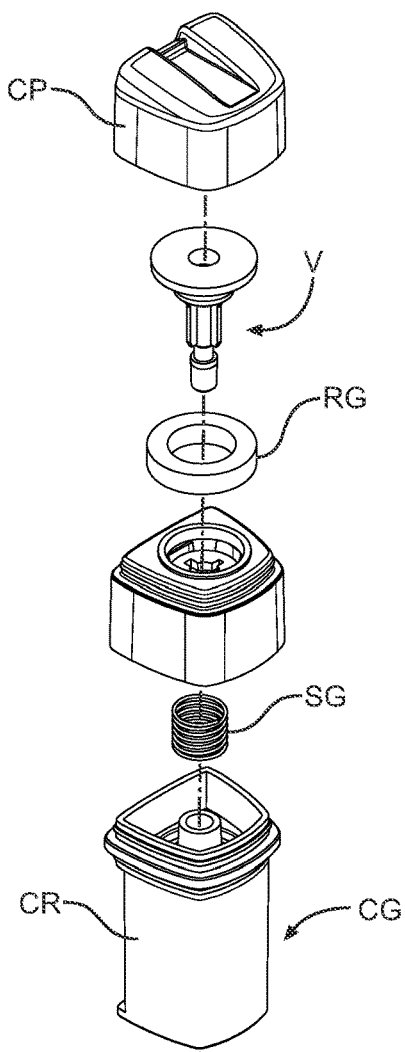
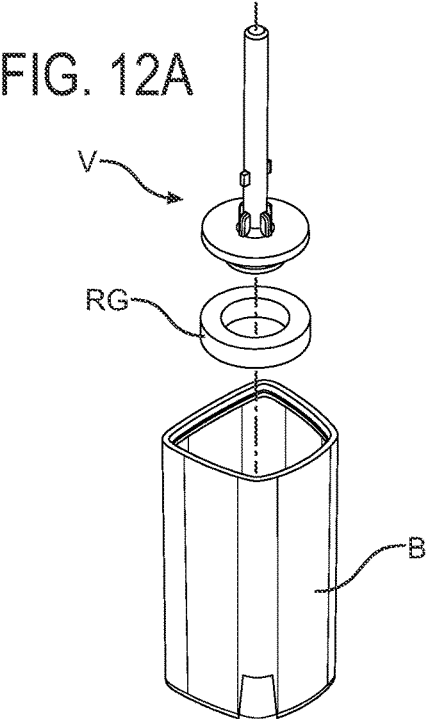
FIG. 12A
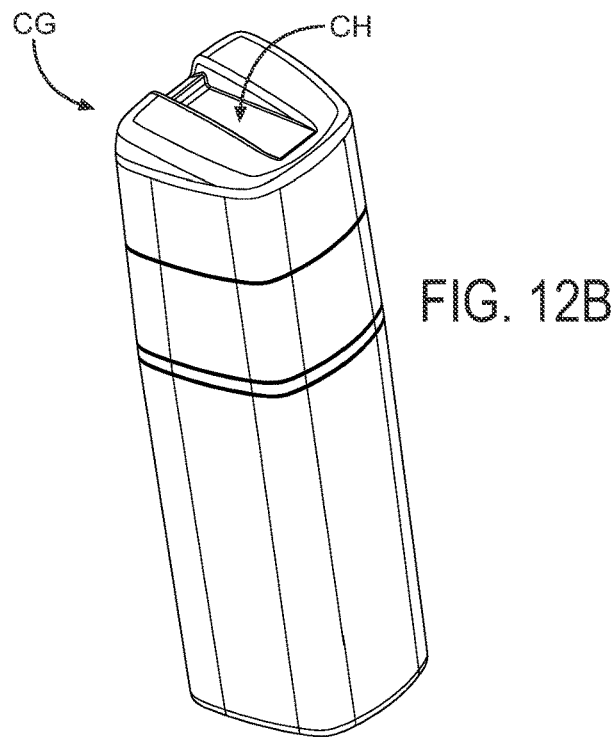
FIG. 12B
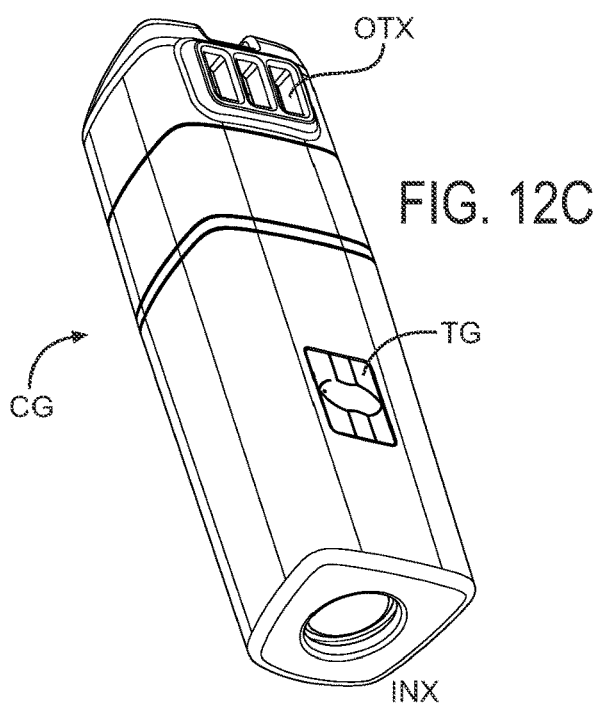
FIG. 12C

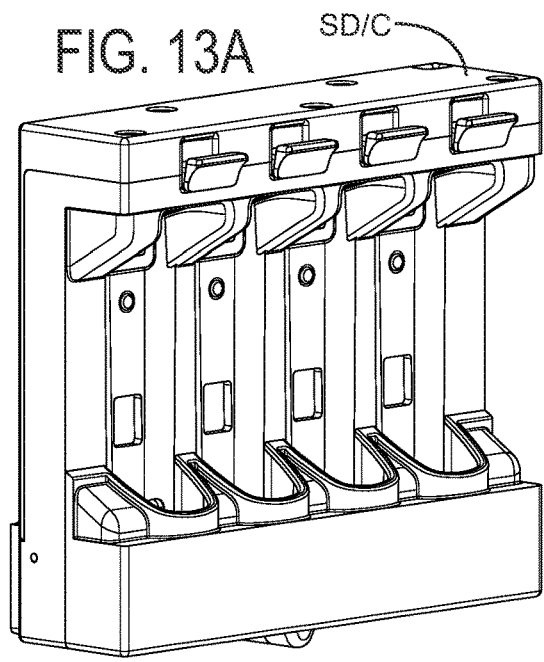
FIG. 13A
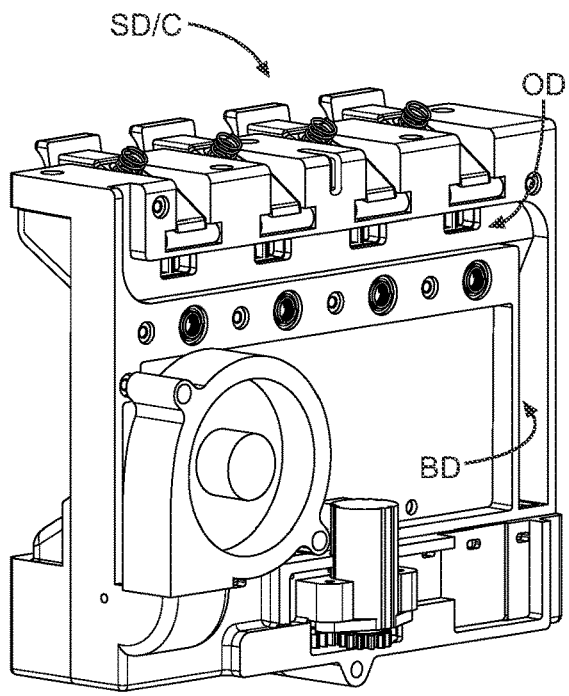
FIG. 13B
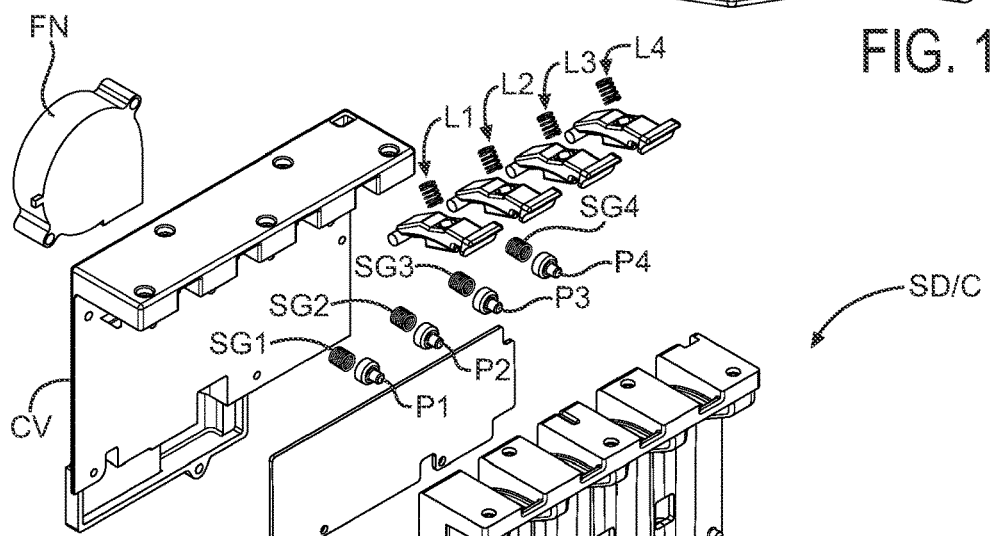
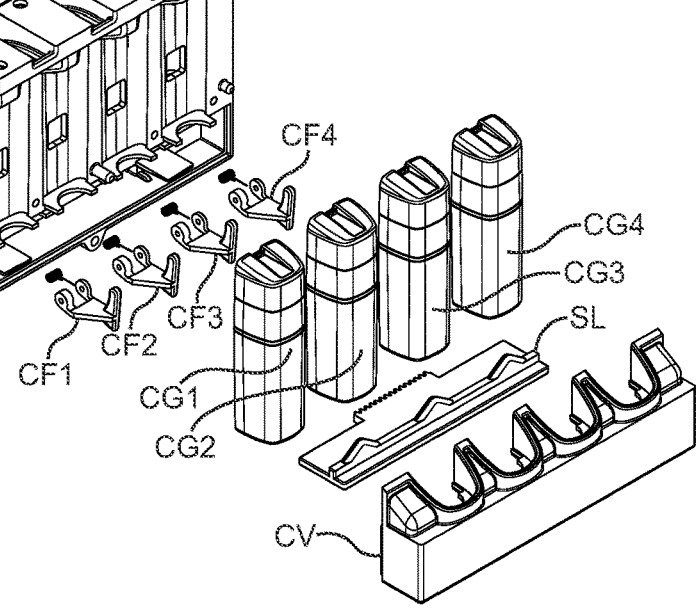
FIG. 13C

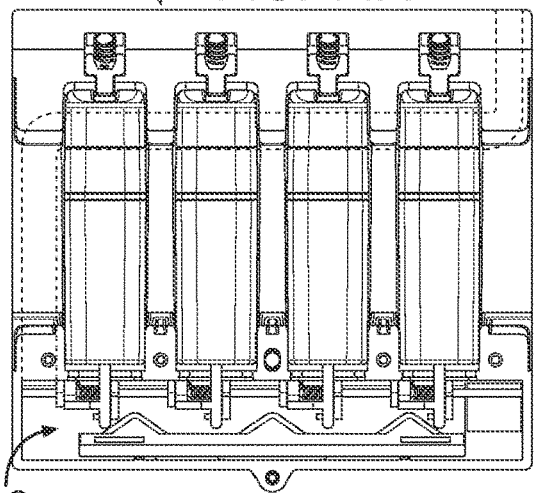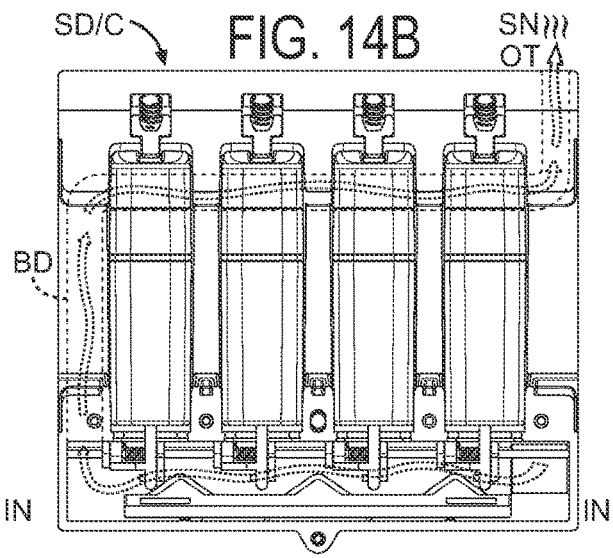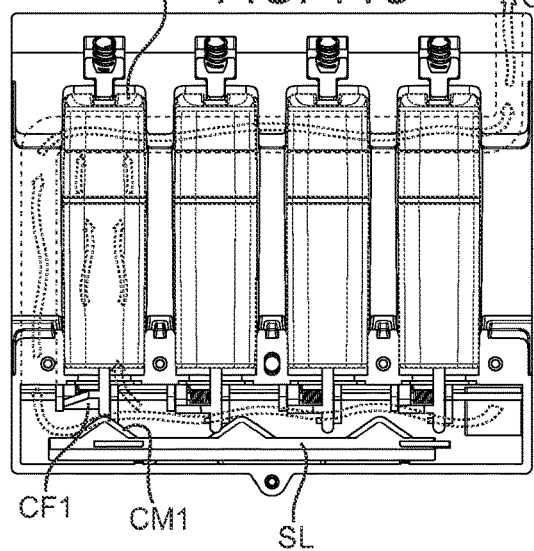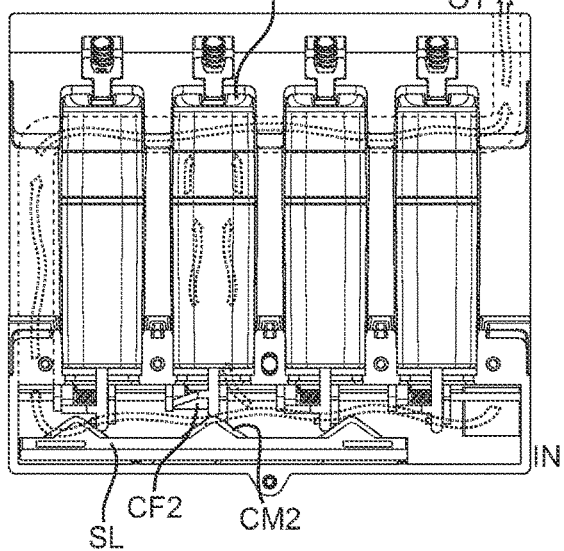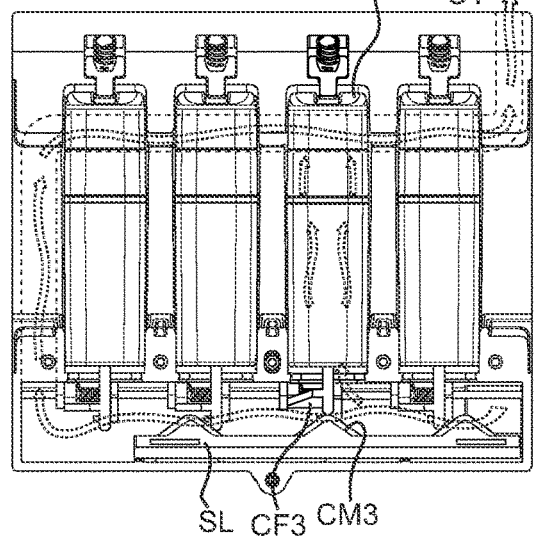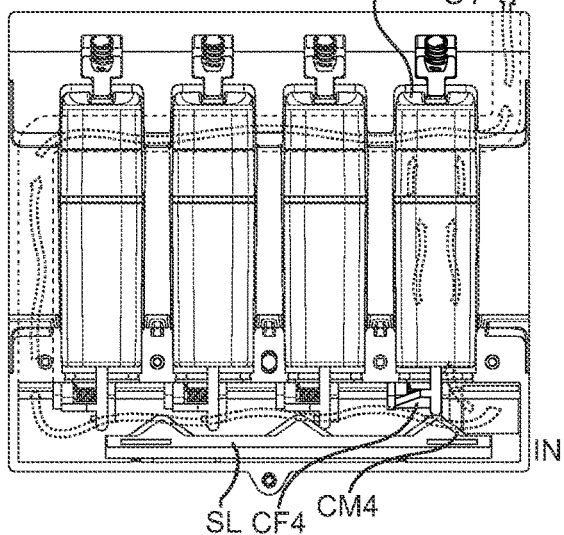

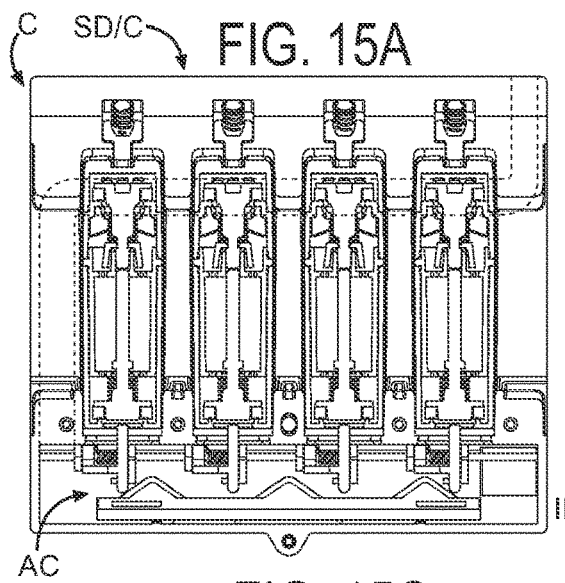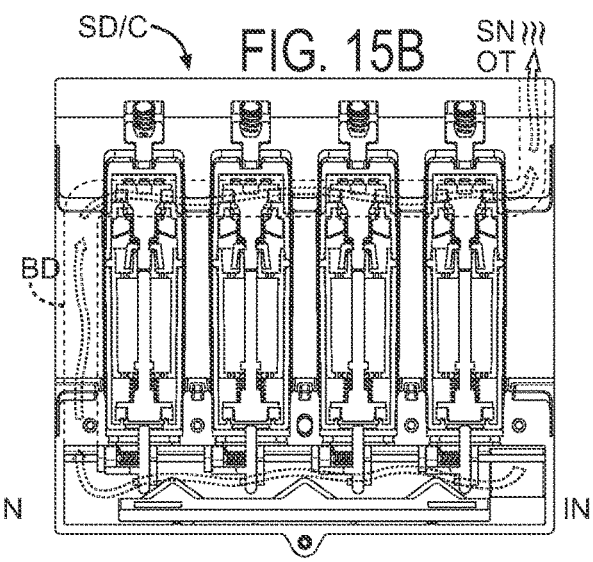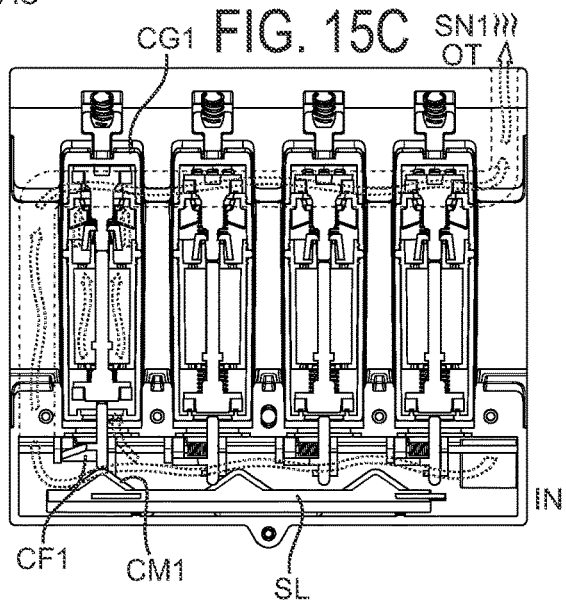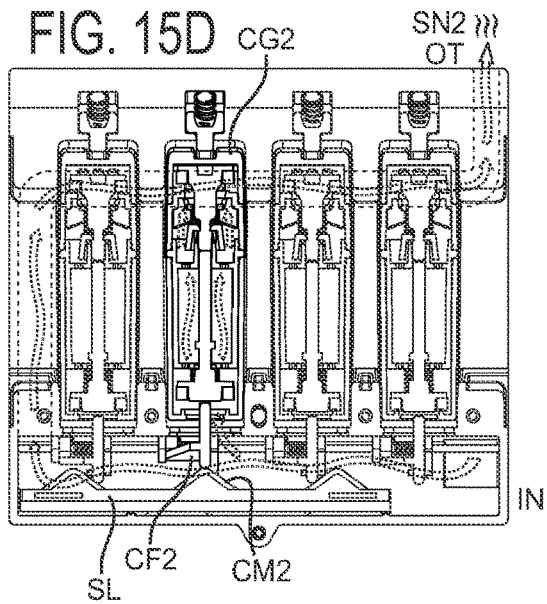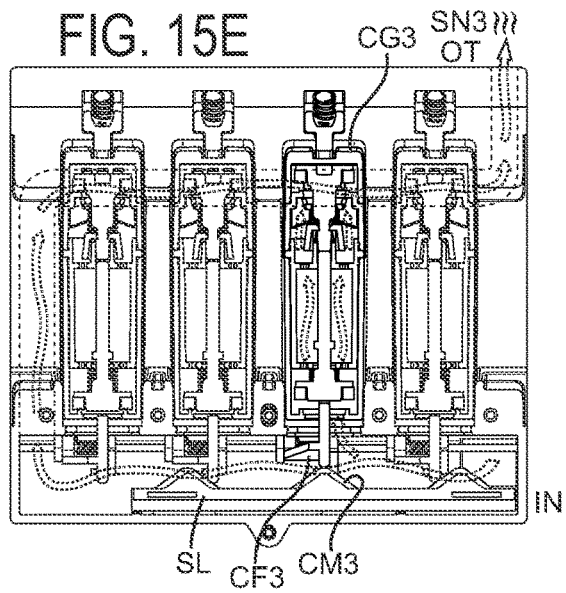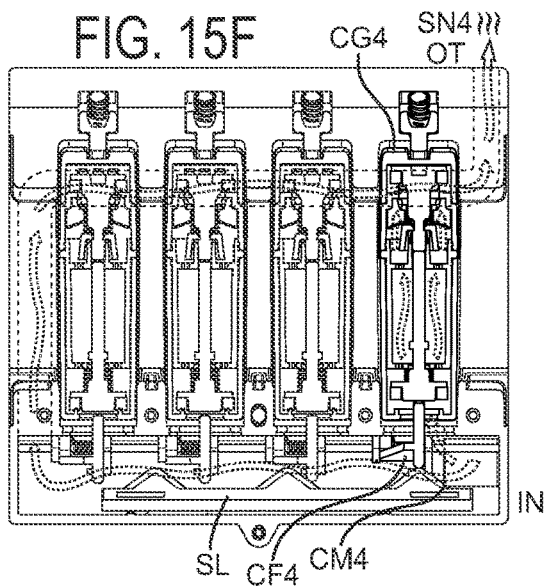

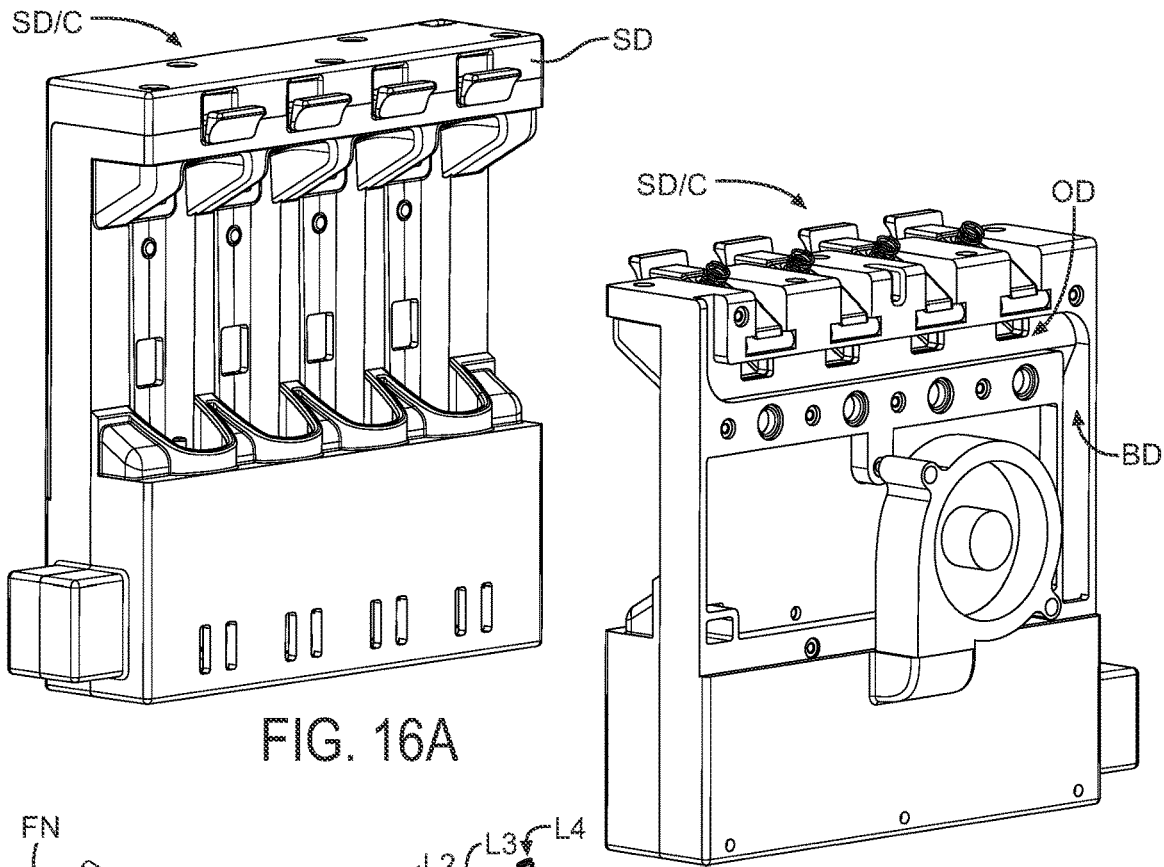
FIG. 16A
FIG. 16B
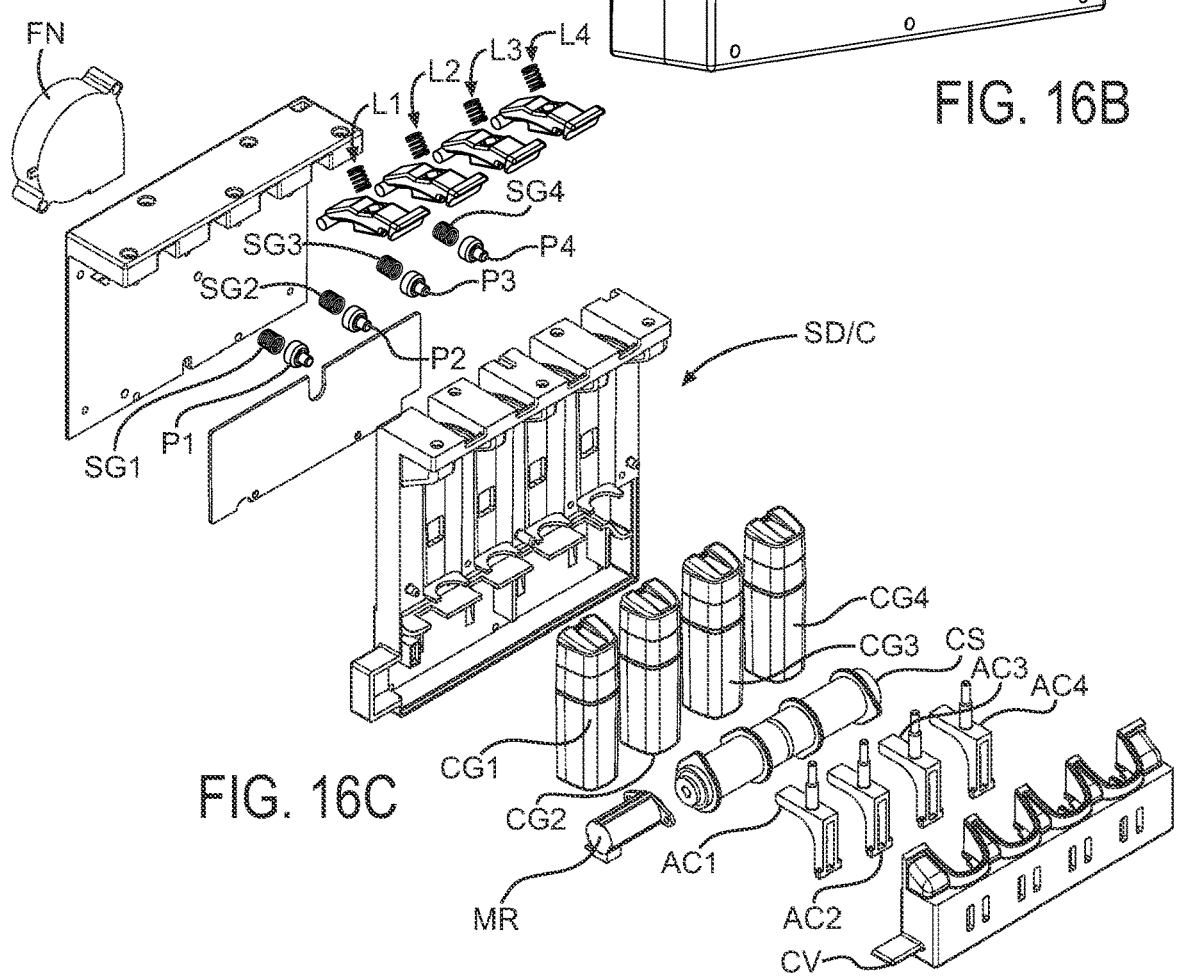
FIG. 16C

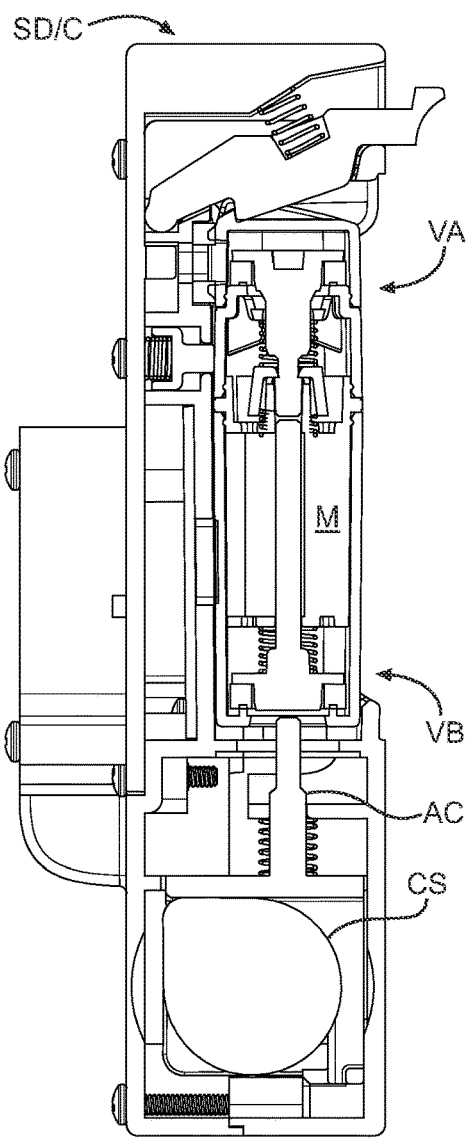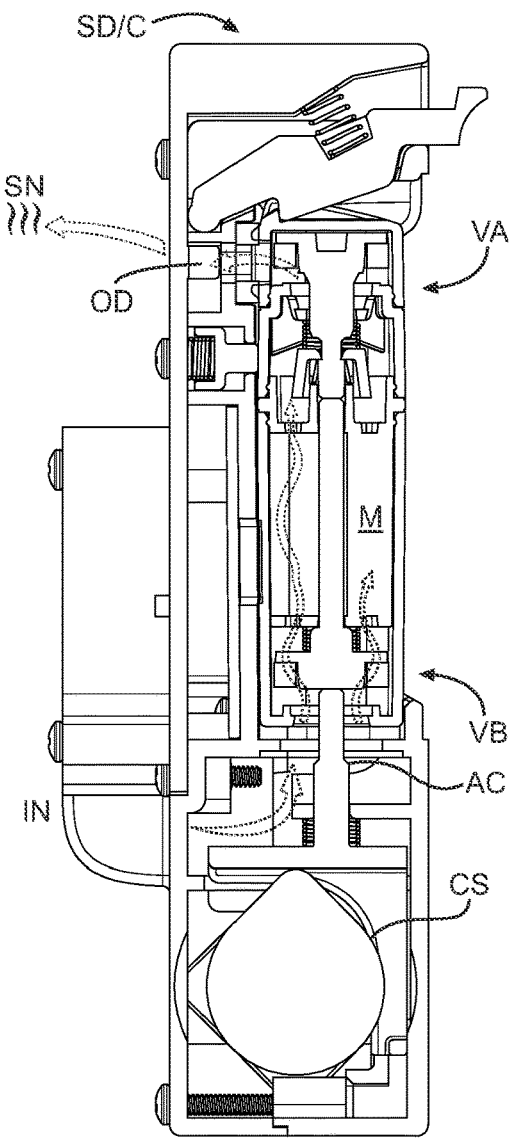
FIG. 17A  FIG. 17B
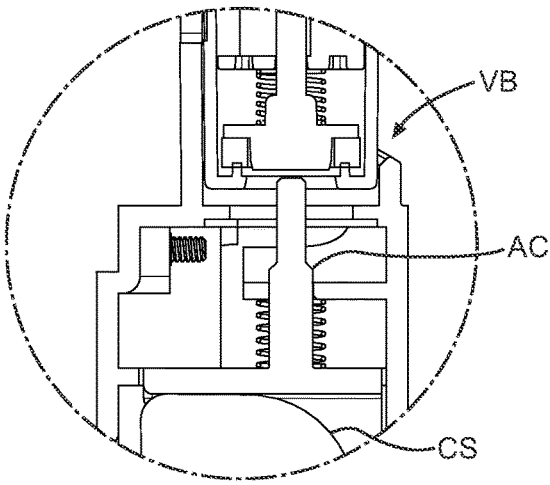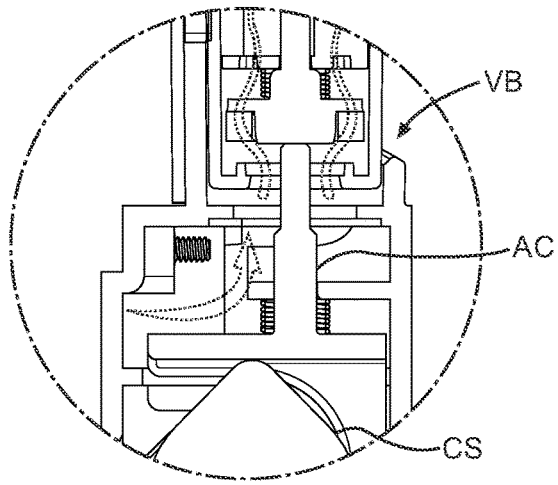
FIG. 17C  FIG. 17D

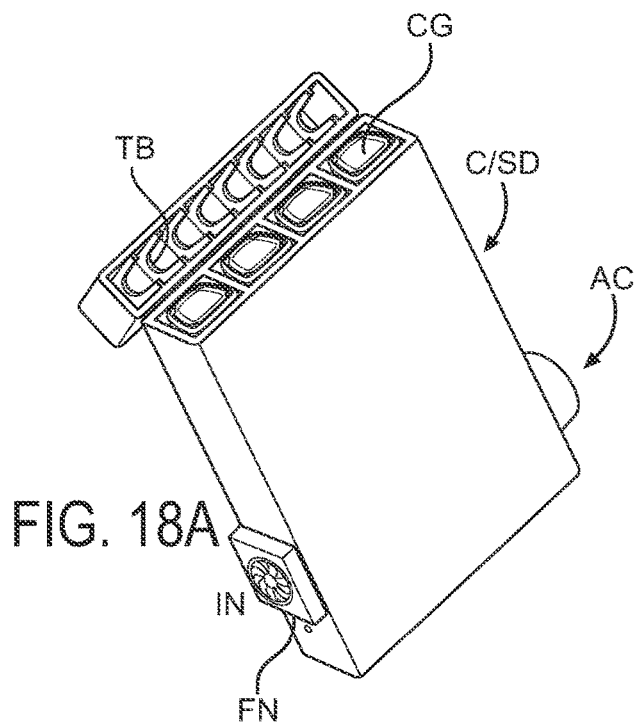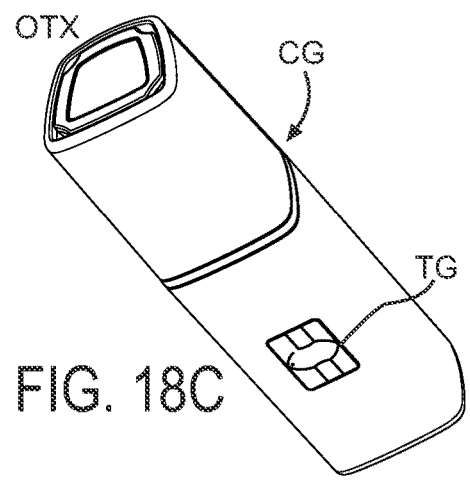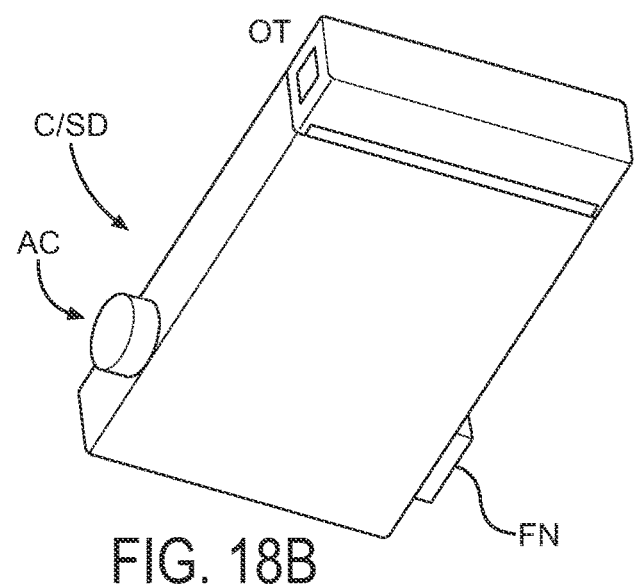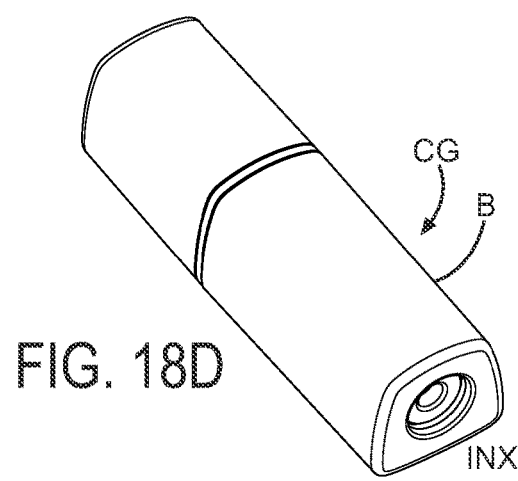

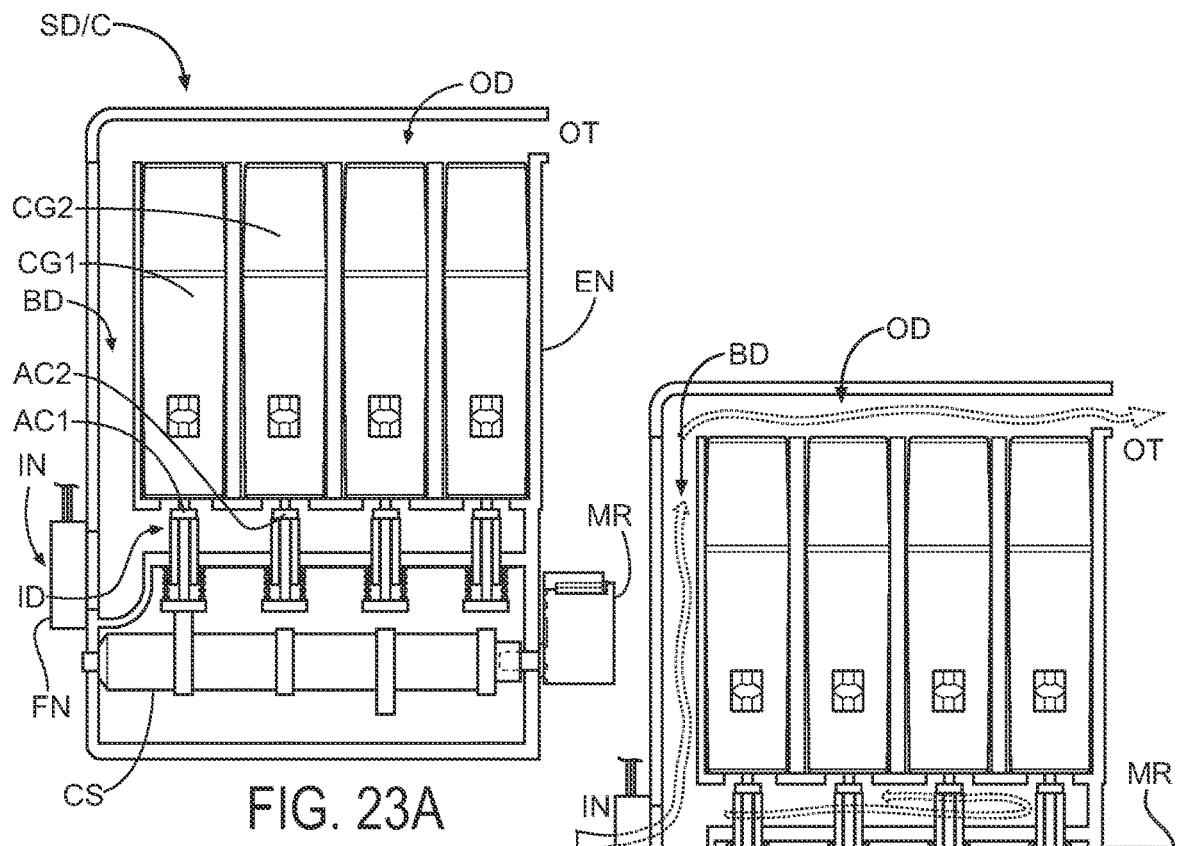
FIG. 23A
FIG. 23B
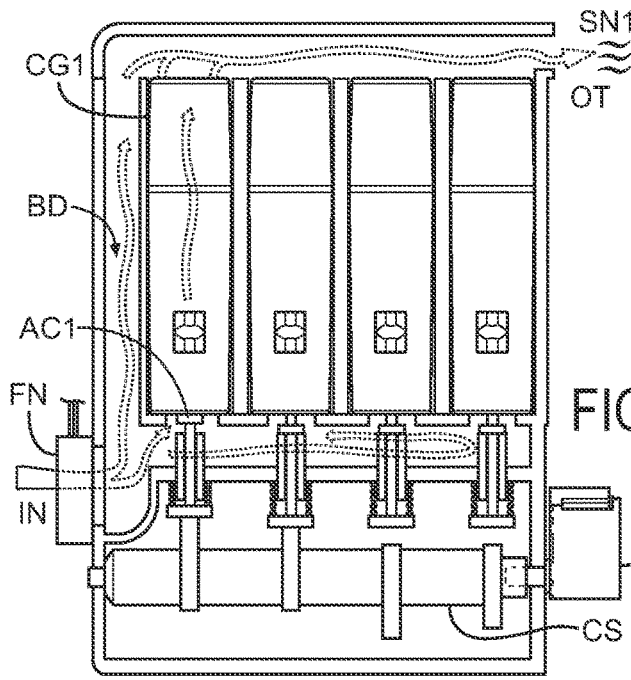
FIG. 23C

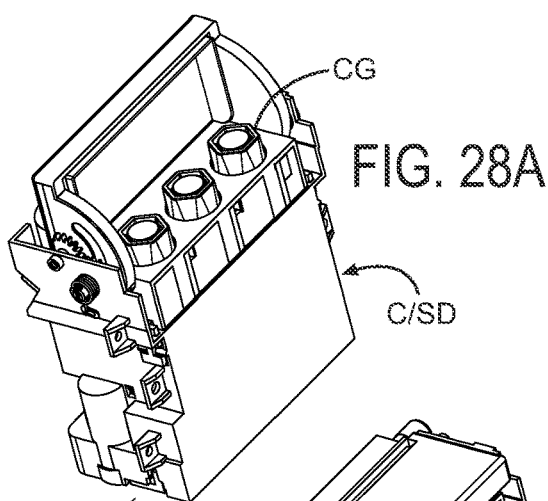
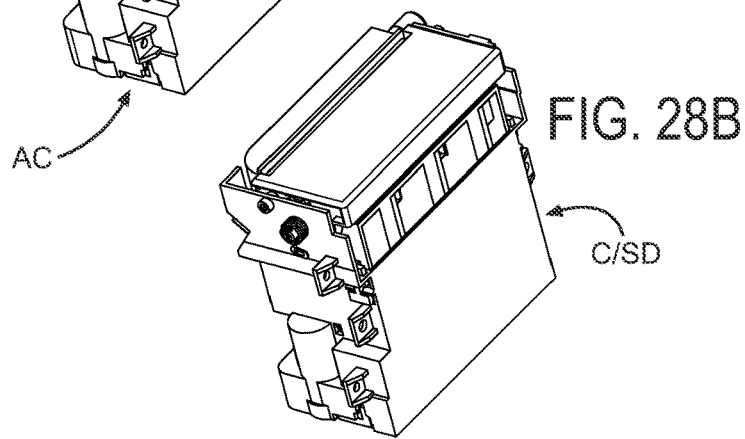
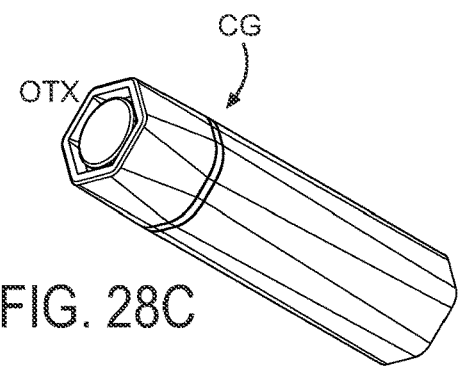
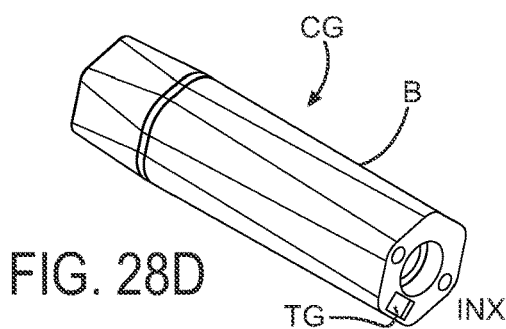
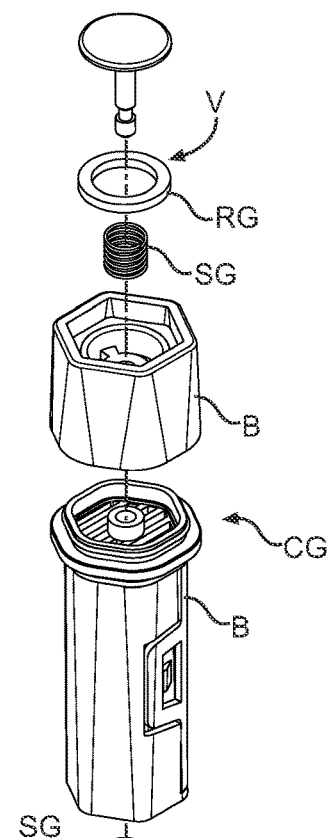
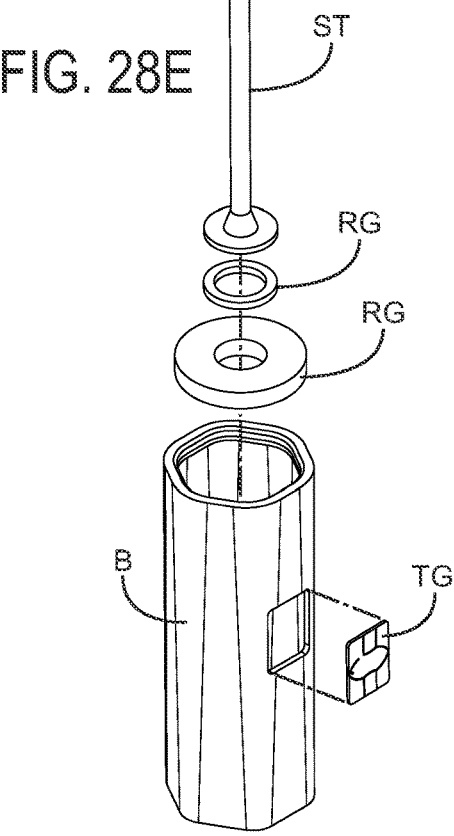

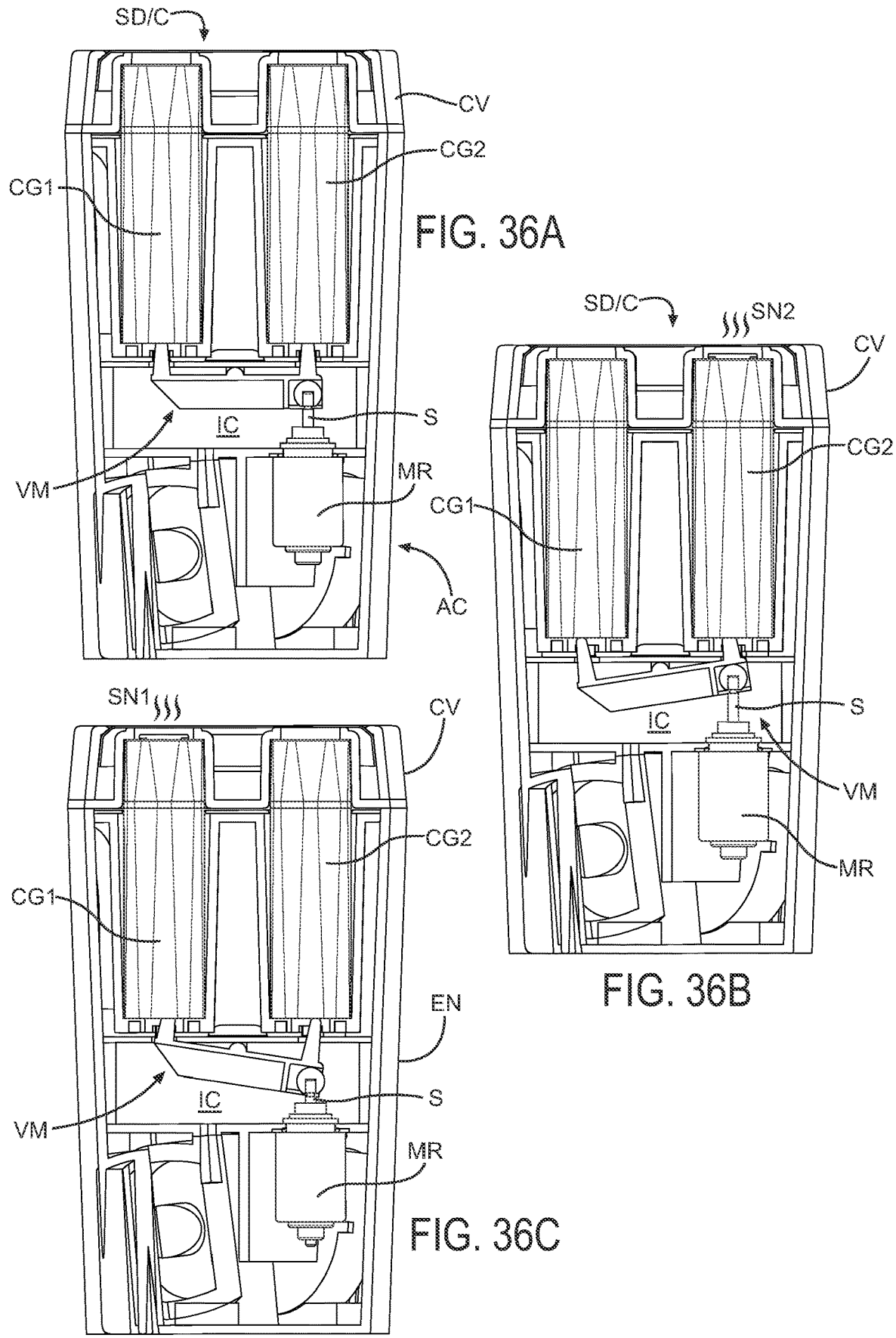

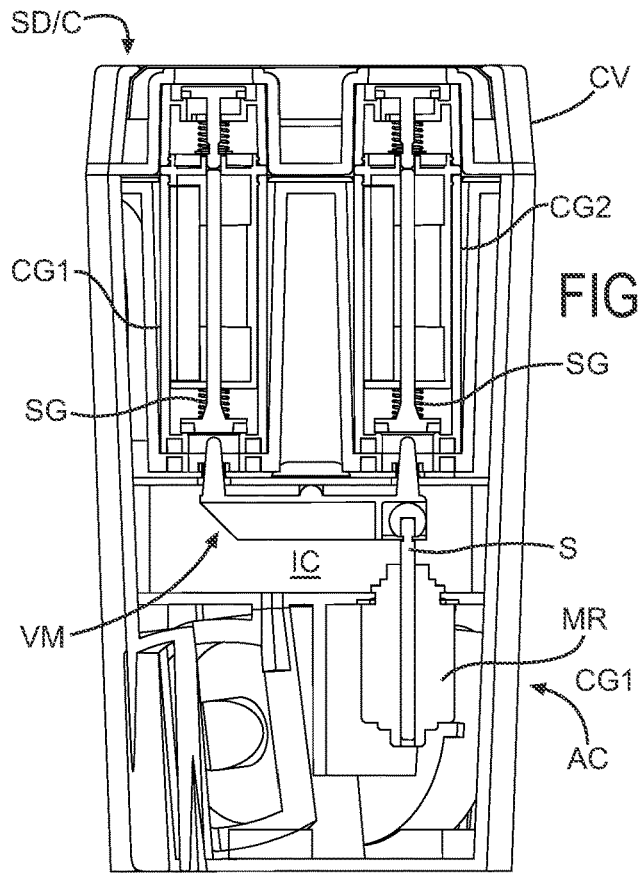
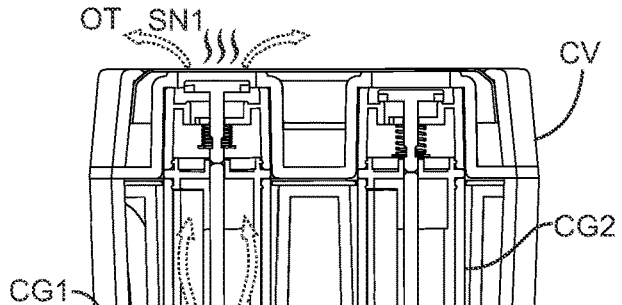
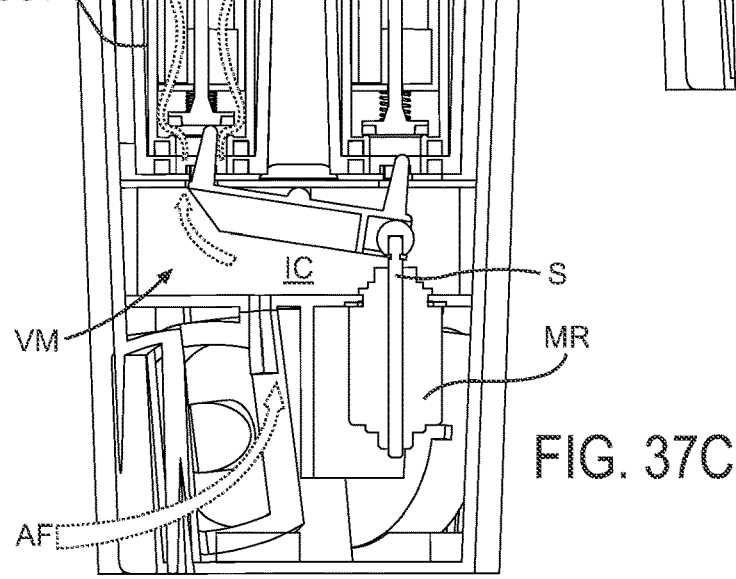
FIG. 37A
FIG. 37B
FIG. 37C

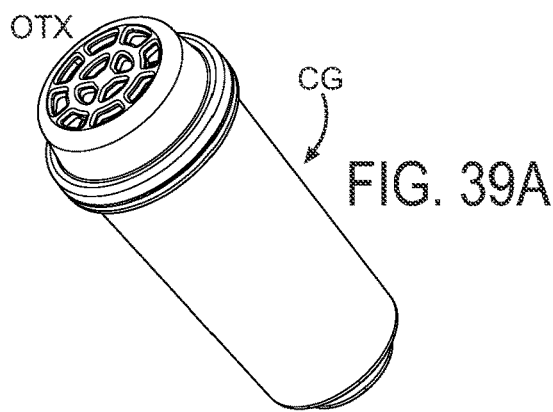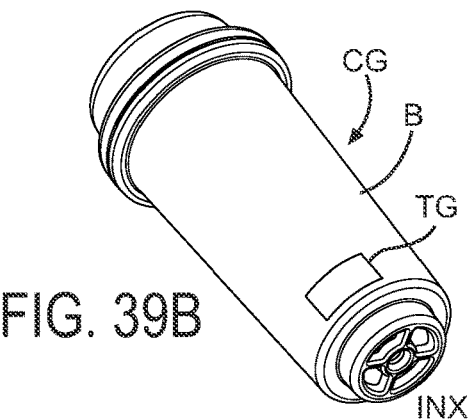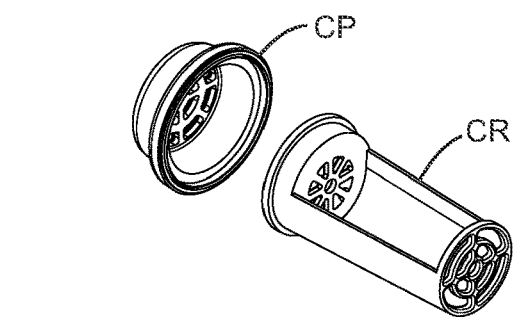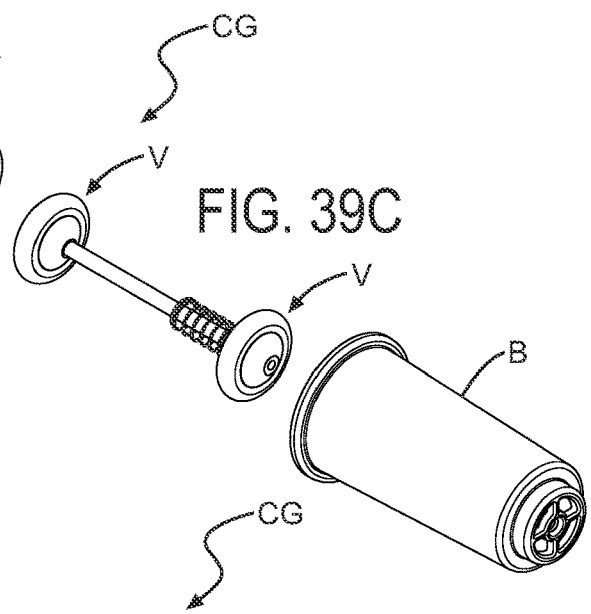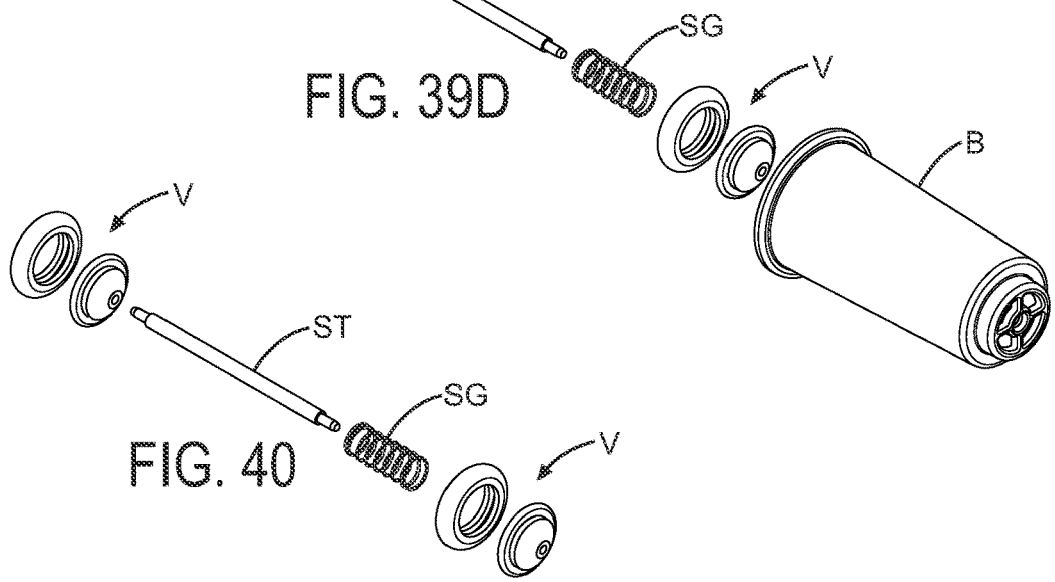

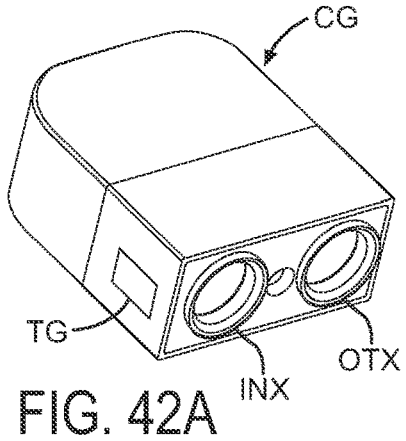
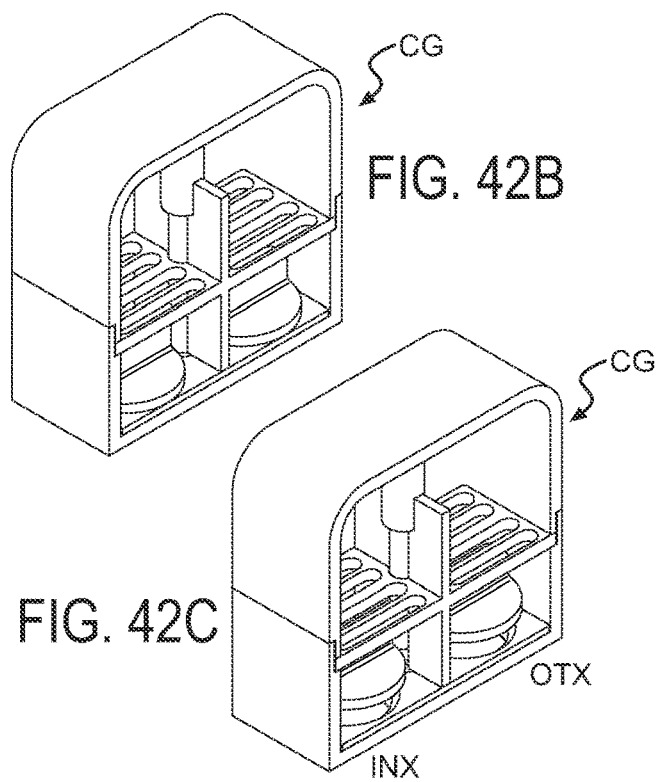
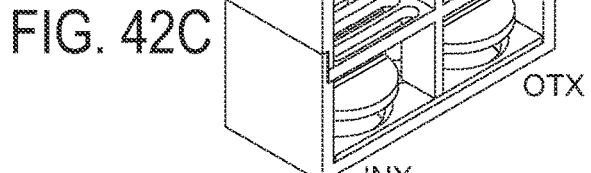
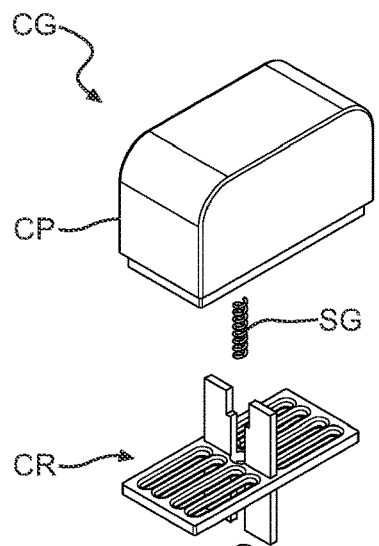
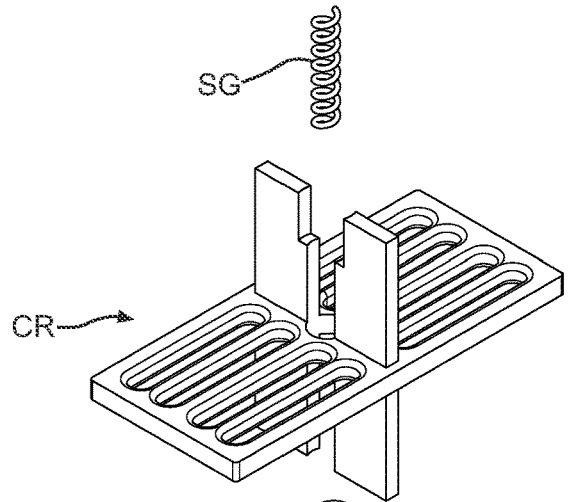
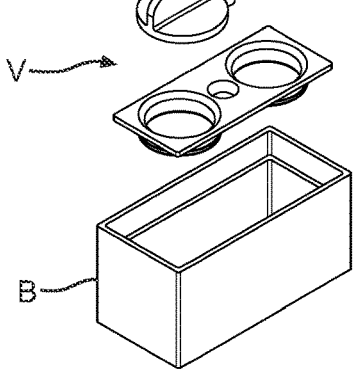
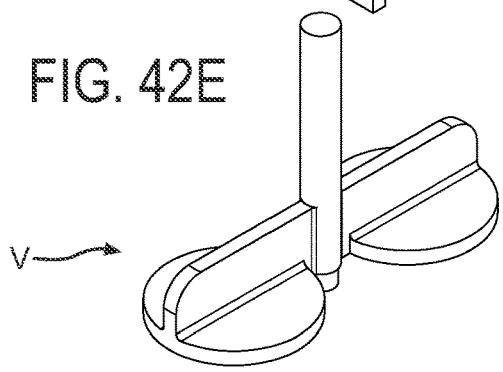

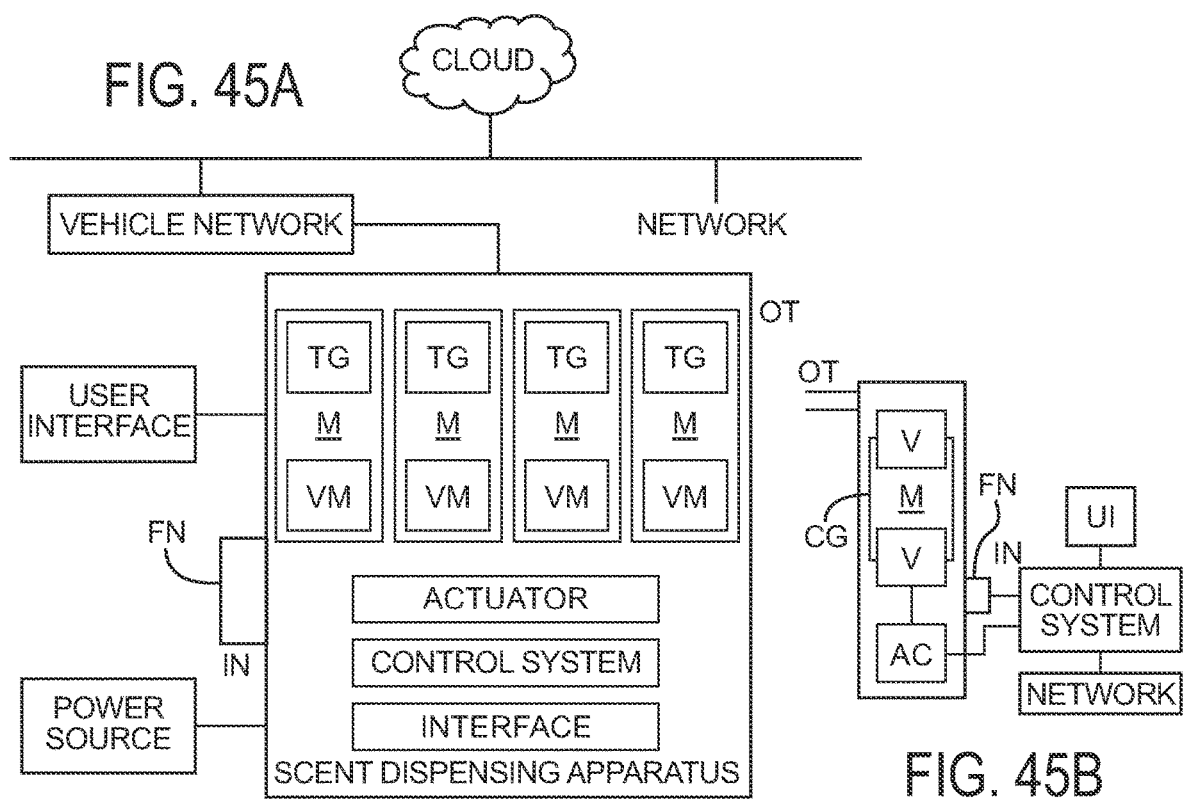
FIG. 45A
FIG. 45B
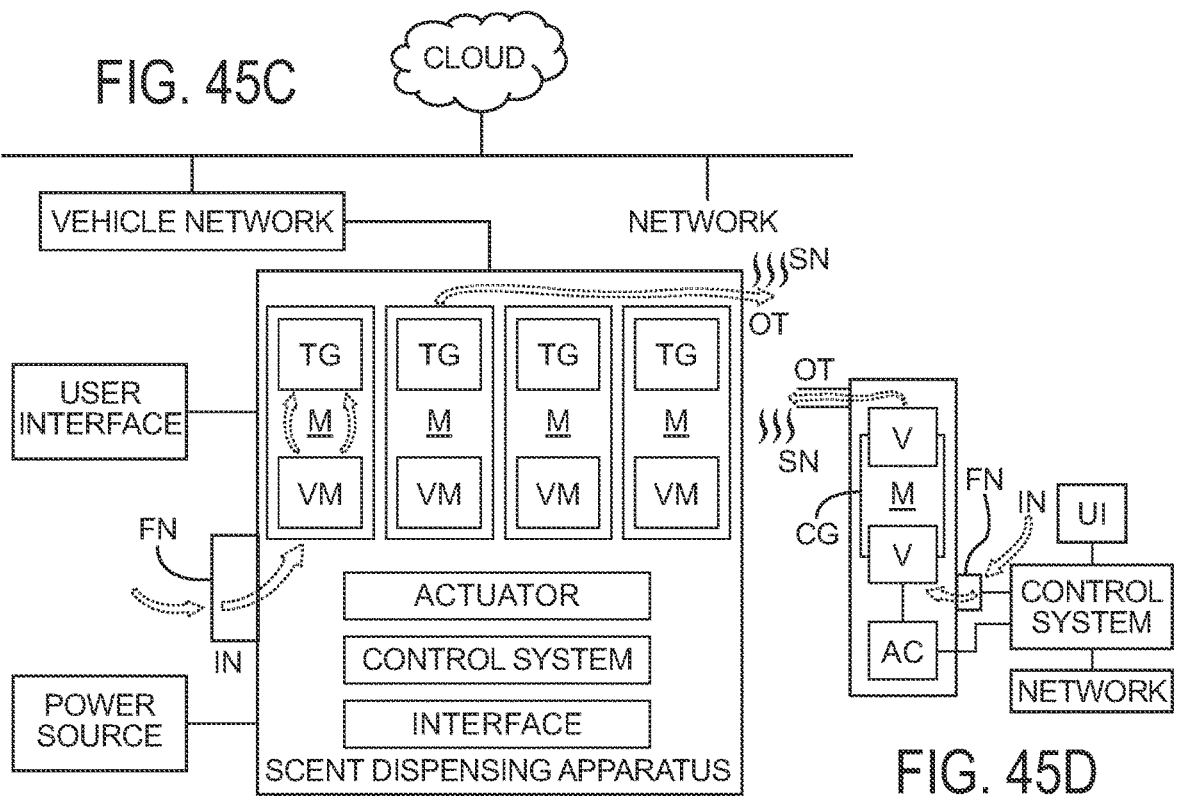
FIG. 45C
FIG. 45D

VEHICLE INTERIOR COMPONENT

CROSS-REFERENCE TO RELATED APPLICATIONS

The present application is a continuation of PCT/International Patent Application No. PCT/US2020/023133 titled "VEHICLE INTERIOR COMPONENT" filed Mar. 17, 2020, which claims the benefit of Chinese Patent Application No. 202020189673.7 filed Feb. 20, 2020 (now Chinese Utility Model No. CN212098347U) and U.S. Provisional Patent Application No. 62/927,768 titled "VEHICLE INTERIOR COMPONENT" filed Oct. 30, 2019 and U.S. Provisional Patent Application No. 62/842,872 titled "VEHICLE INTERIOR COMPONENT" filed May 3, 2019 and U.S. Provisional Patent Application No. 62/835,210 titled "CARTRIDGE FOR SCENT-DISPENSING APPARATUS" filed Apr. 17, 2019 and U.S. Provisional Patent Application No. 62/820,082 titled "CARTRIDGE FOR SCENT-DISPENSING APPARATUS" filed Mar. 18, 2019.

The present application claims priority to and incorporates by reference in full the following patent applications: (a) U.S. Provisional Patent Application No. 62/820,082 titled "CARTRIDGE FOR SCENT-DISPENSING APPARATUS" filed Mar. 18, 2019; (b) U.S. Provisional Patent Application No. 62/835,210 titled "CARTRIDGE FOR SCENT-DISPENSING APPARATUS" filed Apr. 17, 2019; (c) U.S. Provisional Patent Application No. 62/842,872 titled "VEHICLE INTERIOR COMPONENT" filed May 3, 2019; (d) U.S. Provisional Patent Application No. 62/927,768 titled "VEHICLE INTERIOR COMPONENT" filed Oct. 30, 2019; (e) Chinese Patent Application No. 202020189673.7 filed Feb. 20, 2020 (now Chinese Utility Model No. CN212098347U); (f) PCT/International Patent Application No. PCT/US2020/023133 titled "VEHICLE INTERIOR COMPONENT" filed Mar. 17, 2020.

FIELD

The present invention relates to a vehicle interior component.

The present invention relates to a vehicle interior component comprising a scent-dispensing apparatus.

BACKGROUND

It is known to provide a scent-dispensing apparatus for an interior space such as indicated in U.S. Pat. No. 10,058,627 titled "Digital Aroma Cassette Cartridge and Matrix Dispersion System for Remote Controls."

It would be advantageous to provide a vehicle interior component comprising an improved scent-dispensing apparatus/module with at least one cartridge containing scent media; the apparatus/module may comprise an improved fit/interconnection arrangement/interface for each cartridge so that scent from the scent media can be dispensed conveniently and effectively through a selected cartridge/scent media from the component into a space such as a vehicle interior. The cartridge with scent media may be removable/replaceable in the module/apparatus.

SUMMARY

The present invention relates to a component for a vehicle interior configured to dispense scent from scent media into air in a vehicle interior comprising a scent-dispensing apparatus comprising a module providing an inlet and an outlet. The module may comprise an enclosure configured for at least one scent-dispensing cartridge providing scent media. The module may comprise an actuator configured to actuate at least one scent-dispensing cartridge between a sealed state and an unsealed state. The actuator may comprise an arm configured to rotate to actuate the at least one scent-dispensing cartridge. The actuator may comprise a motor configured to pull the arm toward the motor to actuate a first scent-dispensing cartridge. The motor may be configured to push the arm to actuate a second scent-dispensing cartridge. The at least one scent-dispensing cartridge may comprise a first scent-dispensing cartridge and a second scent-dispensing cartridge. The actuator may be configured to provide the scent-dispensing apparatus with (a) a bypass state with the first scent-dispensing cartridge in a sealed state and the second scent-dispensing cartridge in a sealed state; (b) a first actuation state actuating the first scent-dispensing cartridge in an unsealed state with the second scent-dispensing cartridge in the sealed state; (c) a second actuation state actuating the second scent-dispensing cartridge in an unsealed state with the first scent-dispensing cartridge in the sealed state. The actuator may comprise an actuation mechanism comprising (a) an actuator for the first scent-dispensing cartridge; (b) an actuator for the second scent-dispensing cartridge. The actuation mechanism may comprise a cam shaft configured to (a) actuate the first scent-dispensing cartridge from the sealed state to the unsealed state to allow passage of air through scent media of the first scent-dispensing cartridge toward the outlet; (b) actuate the second scent-dispensing cartridge from the sealed state to the unsealed state to allow passage of air through scent media of the second scent-dispensing cartridge toward the outlet. The cam shaft may be configured for (a) a position to provide the bypass state; (b) a position to provide the first actuation state; (c) a position to provide the second actuation state. The actuation mechanism may comprise (a) a cam-follower arrangement to operate a valve arrangement for the first scent-dispensing cartridge; (b) a cam-follower arrangement to operate a valve arrangement for the second scent-dispensing cartridge. The component may comprise a latch configured for (a) a latched state to secure the first scent-dispensing cartridge; (b) an unlatched state to present the first scent-dispensing cartridge for replacement. The component may comprise a plunger configured to present the first scent-dispensing cartridge for replacement in response to movement of the latch from the latched state to the unlatched state.

The present invention relates to a component for a vehicle interior configured to dispense scent from scent media into air in a vehicle interior comprising a scent-dispensing apparatus comprising a module providing an inlet and an outlet. The module may comprise an enclosure configured for at least one scent-dispensing cartridge providing scent media. The module may comprise an actuator configured to actuate at least one scent-dispensing cartridge between a sealed state and an unsealed state. The module may comprise a cover configured for (a) a closed state to conceal the at least one scent-dispensing cartridge; (b) an open state to expose the at least one scent-dispensing cartridge. The cover may comprise at least one of (a) an outlet for the at least one scent-dispensing cartridge or (b) a magnet configured to couple the cover and the module or (c) a mesh configured to conceal the at least one scent-dispensing cartridge and allow air flow to the outlet or (d) a cover structure for the at least one scent-dispensing cartridge configured to form an outlet chamber for the at least one scent-dispensing cartridge. When the cover is in the open state the actuator may be configured for at least one of (a) an inaccessible state with the first scent-dispensing cartridge in an inaccessible position and the second scent-dispensing cartridge in an inaccessible position; (b) a first accessible state actuating the first scent-dispensing cartridge in an accessible position for replacement with the second scent-dispensing cartridge in the inaccessible position; (c) a second accessible state actuating the second scent-dispensing cartridge in an accessible position for replacement with the first scent-dispensing cartridge in the inaccessible position. The apparatus may comprise an inlet duct to the inlet and an outlet duct to the outlet; the inlet duct may be separated from the outlet duct within the module of the apparatus. The component may comprise a fan configured to provide air flow between the inlet and the outlet. The component may comprise a bypass duct; the fan may be configured to direct air (a) to the inlet; (b) through the bypass duct; (c) through the outlet. The fan may be configured for a high speed state and a low speed state; the high speed state may be configured to provide high intensity scent dispersion; the low speed state may be configured to provide low intensity scent dispersion. The at least one scent-dispensing cartridge may comprise a first scent-dispensing cartridge and a second scent-dispensing cartridge; the actuator may comprise a mechanism configured to (a) rotate in a first direction to actuate the first scent-dispensing cartridge and (b) rotate in a second direction generally opposite the first direction to actuate the second scent-dispensing cartridge.

The present invention relates to a component for a vehicle interior configured to dispense scent from scent media into air in a vehicle interior comprising a scent-dispensing apparatus comprising a module providing an inlet and an outlet. The module may comprise an enclosure configured for at least one scent-dispensing cartridge providing scent media. The module may comprise an actuator configured to actuate at least one scent-dispensing cartridge between a sealed state and an unsealed state. The at least one cartridge may comprise a cartridge system comprising a cartridge. The cartridge may comprise a body comprising an inlet port and an outlet port and a chamber configured to contain scent media. The valve assembly may comprise a flow control element configured to facilitate air flow for the cartridge. The flow control element of the valve assembly may be configured to control air flow for the cartridge into the inlet port across scent media in the chamber and from the outlet port; so that the flow control element when open may be configured to facilitate air flow across scent media in the chamber of the body and when closed may be configured to provide a seal of air flow to scent media in the chamber of the body. The actuator may be configured to compress a spring of the at least one scent-dispensing cartridge to actuate the at least one scent-dispensing cartridge from the sealed state to the unsealed state to allow air flow through scent media toward the outlet. The actuator may comprise an actuation mechanism comprising a shaft; the shaft may be configured to translate to actuate an actuator to rotate to actuate the first scent-dispensing cartridge. The actuator may comprise a mechanism configured to actuate a valve arrangement for the at least one scent-dispensing cartridge; the mechanism may comprise a slider arrangement configured to provide cam action to open the valve arrangement for the unsealed state and to close the valve arrangement for the sealed state.

The present invention relates to a component for a vehicle interior configured to dispense scent from scent media into air in a vehicle interior comprising a scent-dispensing apparatus comprising a module providing an inlet and an outlet. The module may comprise an enclosure configured for at least one scent-dispensing cartridge providing scent media; the module may comprise an actuator configured to actuate at least one scent-dispensing cartridge between a sealed state and an unsealed state. The at least one scent-dispensing cartridge may comprise a first scent-dispensing cartridge and a second scent-dispensing cartridge. The actuator may be configured to provide the scent-dispensing apparatus with (a) a bypass state with the first scent-dispensing cartridge in a sealed state and the second scent-dispensing cartridge in a sealed state; (b) a first actuation state actuating the first scent-dispensing cartridge in an unsealed state with the second scent-dispensing cartridge in the sealed state; (c) a second actuation state actuating the second scent-dispensing cartridge in an unsealed state with the first scent-dispensing cartridge in the sealed state. The actuator may comprise an actuation mechanism comprising (a) an actuator for the first scent-dispensing cartridge; (b) an actuator for the second scent-dispensing cartridge. The actuation mechanism may comprise a cam shaft configured to (a) actuate the first scent-dispensing cartridge from the sealed state to the unsealed state to allow passage of air through scent media of the first scent-dispensing cartridge toward the outlet; (b) actuate the second scent-dispensing cartridge from the sealed state to the unsealed state to allow passage of air through scent media of the second scent-dispensing cartridge toward the outlet. The cam shaft may be configured for (a) a position to provide the bypass state; (b) a position to provide the first actuation state; (c) a position to provide the second actuation state. The actuation mechanism may comprise (a) a cam/follower arrangement to operate a valve arrangement for the first scent-dispensing cartridge; (b) a cam/follower arrangement to operate a valve arrangement for the second scent-dispensing cartridge. The component may comprise a latch configured for (a) a latched state to secure the first scent-dispensing cartridge; (b) an unlatched state to present the first scent-dispensing cartridge for replacement. The component may comprise a plunger configured to present the first scent-dispensing cartridge for replacement in response to movement of the latch from the latched state to the unlatched state. The component may comprise a cover configured for (a) a closed state to conceal the at least one scent-dispensing cartridge; (b) an open state to expose the at least one scent-dispensing cartridge. When the cover is in the open state, the actuator may be configured for at least one of (a) an inaccessible state with the first scent-dispensing cartridge in an inaccessible position and the second scent-dispensing cartridge in an inaccessible position; (b) a first accessible state actuating the first scent-dispensing cartridge in an accessible position for replacement with the second scent-dispensing cartridge in the inaccessible position; (c) a second accessible state actuating the second scent-dispensing cartridge in an accessible position for replacement with the first scent-dispensing cartridge in the inaccessible position. The component may comprise a cover configured for (a) a closed state to conceal the at least one scent-dispensing cartridge; (b) an open state to expose the at least one scent-dispensing cartridge; the cover may comprise the outlet. The apparatus may comprise an inlet duct to the inlet and an outlet duct to the outlet; the inlet duct may be separated from the outlet duct within the module of the apparatus; a cover may be configured to form the outlet duct. The component may comprise a fan configured to provide air flow between the inlet and the outlet. The component may comprise a bypass duct; the fan may be configured to direct air (a) to the inlet; (b) through the bypass duct; (c) through the outlet. The fan may be configured for a high speed state and a low speed state; the high speed state may be configured to provide high intensity scent dispersion; the low speed state may be configured to provide low intensity scent dispersion. The actuator may comprise a mechanism configured to (a) rotate in a first direction to actuate the first scent-dispensing cartridge and (b) rotate in a second direction generally opposite the first direction to actuate the second scent-dispensing cartridge. The actuator may be configured for (a) a default state with the first scent-dispensing cartridge in a sealed state and the second scent-dispensing cartridge in a sealed state; (b) a first actuation state actuating the first scent-dispensing cartridge in an unsealed state with the second scent-dispensing cartridge in the sealed state; (c) a second actuation state actuating the second scent-dispensing cartridge in an unsealed state with the first scent-dispensing cartridge in the sealed state. The actuator may comprise a shaft configured to (a) actuate the first scent-dispensing cartridge from the sealed state to the unsealed state to allow passage of air through scent media of the first scent-dispensing cartridge toward the outlet; (b) actuate the second scent-dispensing cartridge from the sealed state to the unsealed state to allow passage of air through scent media of the second scent-dispensing cartridge toward the outlet. The shaft may be configured for (a) a first position to provide the first actuation state; (b) a second position to provide the second actuation state; (c) a third position to provide the default state; the first position may comprise an extended position; the second position may comprise a retracted position; the third position may comprise a middle position. The actuator may be configured to compress a spring of the at least one scent-dispensing cartridge to actuate the at least one scent-dispensing cartridge from the sealed state to the unsealed state to allow air flow through the scent media toward the outlet. The component may comprise a motor for the actuator; the actuator may comprise an actuation mechanism comprising a shaft; the module may be configured to provide (a) a default state with a first scent-dispensing cartridge in a sealed state and a second scent-dispensing cartridge in a sealed state and (b) a first actuation state actuating the first scent-dispensing cartridge in an unsealed state with the second scent-dispensing cartridge in the sealed state and (c) a second actuation state actuating the second scent-dispensing cartridge in an unsealed state with the first scent-dispensing cartridge in the sealed state; the motor may be configured to move the shaft between (a) a first position to provide the first actuation state; (b) a second position to provide the second actuation state; (c) a third position to provide the default state; the first position may comprise an extended position; the second position may comprise a retracted position; the third position may comprise a middle position. The shaft may be configured to translate to actuate an actuator to rotate to actuate the first scent-dispensing cartridge. The actuator may comprise a seesaw mechanism; the seesaw mechanism may comprise an arm comprising (a) an actuator for a first scent-dispensing cartridge; (b) an actuator for a second scent-dispensing cartridge. The seesaw mechanism may comprise a motor and a shaft; the motor may be configured to move the shaft at an end of the arm to rotate the arm. The actuator may comprise an arm configured to rotate to actuate the at least one scent-dispensing cartridge; the actuator may comprise a motor configured to pull the arm toward the motor to actuate a first scent-dispensing cartridge; the motor may be configured to push the arm to actuate a second scent-dispensing cartridge. The module may comprise a cover configured for (a) a closed state to conceal the at least one scent-dispensing cartridge; (b) an open state to expose the at least one scent-dispensing cartridge. The cover may comprise at least one of (a) an outlet for the at least one scent-dispensing cartridge or (b) a magnet configured to couple the cover and the module or (c) a mesh configured to conceal the at least one scent-dispensing cartridge and allow air flow to the outlet or (d) a cover structure for the at least one scent-dispensing cartridge configured to form an outlet chamber for the at least one scent-dispensing cartridge. The module may comprise an inlet chamber between the inlet and the outlet; the inlet chamber may be separated from the outlet within the enclosure of the module; the actuator may be adjacent to the inlet. The actuator may comprise a mechanism configured to actuate a valve arrangement for the at least one scent-dispensing cartridge; the mechanism may comprise a slider arrangement configured to provide cam action to open the valve arrangement for the unsealed state and to close the valve arrangement for the sealed state. The component may comprise a user interface configured to facilitate the selection of scent by selection of at least one scent-dispensing cartridge for actuation and/or for selection of intensity of scent from at least one scent-dispensing cartridge. The at least one scent-dispensing cartridge may comprise at least one interchangeable cartridge for use in the module in a vehicle interior; at least one interchangeable cartridge may be removed and replaced in the module; selection of at least one interchangeable cartridge may provide selection of scent media; actuation of at least one interchangeable cartridge may facilitate the selection of scent from scent media in at least one interchangeable cartridge for the vehicle interior. The component may comprise at least one of: (a) a console; (b) an overhead console; (c) a floor console; (d) a center console. The at least one cartridge may comprise a cartridge system comprising a cartridge; the cartridge may comprise a body comprising an inlet port and an outlet port and a chamber configured to contain scent media; the valve assembly may comprise a flow control element configured to facilitate air flow for the cartridge; the flow control element of the valve assembly may be configured to control air flow for the cartridge into the inlet port across scent media in the chamber and from the outlet port; so that the flow control element when open is configured to facilitate air flow across scent media in the chamber of the body and when closed is configured to provide a seal of air flow to scent media in the chamber of the body.

The present invention also relates to a cartridge system for a scent-dispensing apparatus providing an inlet and an outlet configured to dispense scent from scent media into air in a vehicle interior comprising: a cartridge comprising a body comprising an inlet port and an outlet port and a chamber configured to contain scent media; and a valve assembly comprising a flow control element configured to facilitate air flow for the cartridge. The flow control element of the valve assembly may be configured to control air flow for the cartridge into the inlet port across scent media in the chamber and from the outlet port so that the flow control element when open may be configured to facilitate air flow across scent media in the chamber of the body and when closed may be configured to provide a seal of air flow to scent media in the chamber of the body. The seal may comprise an air-tight leak-proof seal. The cartridge may comprise a cap for the body; the cap may be configured to be removed to provide scent media into the chamber. The valve assembly may be configured for (1) an enclosed state to provide a seal at the inlet port and a seal at the outlet port and (2) a pass-through state to provide flow of air through the inlet port across scent media through the outlet port. The flow control element of the valve assembly may comprise a valve. The flow control element of the valve assembly may comprise the valve and a seal configured for at least one of (1) to prevent air flow through the inlet port and/or (2) to prevent air flow through the outlet port. The valve may comprise a set of valves; the seal may comprise a set of seals. The valve may comprise a valve for the inlet port and a valve for the outlet port; the seal may comprise a seal for the inlet port and a seal for the outlet port. The valve assembly may comprise a valve mechanism comprising a valve for the inlet port and a valve for the outlet port. The valve mechanism may comprise a spring configured to facilitate operation of at least one of (a) the valve for the inlet port or (b) the valve for the outlet port. The valve for the inlet port may be configured to move relative to the valve for the outlet port. The valve mechanism may comprise a spring configured to compress to actuate the valve mechanism from a sealed state to prevent air flow across the scent media in the cartridge to an open state to allow air flow across the scent media in the cartridge. The valve assembly may comprise an inlet valve and an outlet valve. The inlet valve may be configured to move relative to the outlet port (a) to provide air flow from the inlet port across scent media in the chamber to the outlet port when open and (b) to provide a seal of scent media in the chamber of the body when closed. The inlet valve may be configured to move the outlet valve to provide flow of air across scent media through the outlet port. The inlet valve may be configured to provide the inlet port and the outlet valve may be configured to provide the outlet port. The cartridge may comprise the valve assembly; the valve assembly may comprise the inlet valve and the outlet valve. The valve assembly may be configured to be actuated to an unsealed state for air flow from the inlet to the outlet; scent may be dispensed from the cartridge by air flow through the inlet valve and across scent media in the chamber and through the outlet valve when the valve assembly is in the unsealed state. The cartridge may comprise a tag for data; data may comprise information.

The present invention also relates to a system configured to dispense scent by air flow across scent media into a vehicle interior comprising a module comprising an inlet and an outlet and configured to dispense scent through actuation of a valve mechanism. The module may be configured to contain at least one cartridge comprising scent media. The valve mechanism may comprise a flow control element between the inlet and the outlet and configured to control air flow across scent media in at least one cartridge so that the module may be configured to dispense scent by air flow into the inlet and across scent media in at least one cartridge and from the outlet into the vehicle interior. The system may comprise at least one cartridge and an actuation mechanism configured to actuate the valve mechanism; the at least one cartridge may comprise a valve configured to be actuated by the valve mechanism. The valve mechanism may comprise a set of valves. The at least one cartridge may be removable from the module; the at least one cartridge may be replaceable within the module. The at least one cartridge may comprise a set of cartridges; the set of cartridges may comprise a first scent cartridge comprising first scent media to provide a first scent and a second scent cartridge comprising second scent media to provide a second scent; the valve mechanism may comprise a first valve assembly for the first scent cartridge and a second valve assembly for the second scent cartridge. The system may comprise an actuation mechanism for the valve mechanism; the actuation mechanism may be configured to actuate a valve of the first valve assembly for the first scent cartridge and a valve of the second valve assembly for the second scent cartridge.

The actuation mechanism may comprise at least one of (a) a cam mechanism; (b) a cam mechanism operated by a controller. The system may comprise an actuation mechanism for the valve mechanism; the at least one cartridge may comprise a first scent cartridge comprising first scent media and a first valve assembly and a second scent cartridge comprising second scent media and a second valve assembly; the valve mechanism may comprise the first valve assembly and the second valve assembly; the actuation mechanism may comprise a cam mechanism configured to actuate the valve mechanism. The cam mechanism may be configured to selectively open and close a valve of the first valve assembly for the first scent cartridge and to selectively open and close a valve of the second valve assembly of the second scent cartridge. The cam mechanism may be configured to selectively open and close a set of valves of the first valve assembly for the first scent cartridge and to selectively open and close a set of valves of the second valve assembly of the second scent cartridge. The actuation mechanism may be operated by a controller and configured to selectively operate the valve mechanism to open and close a valve of the first valve assembly for the first scent cartridge and to open and close a valve of the second valve assembly of the second scent cartridge. The system may comprise a fan configured to provide air flow through the module; the valve mechanism may comprise at least one valve; the fan may be configured to provide air flow through the at least one valve. The system may comprise a set of cartridges comprising a first scent cartridge comprising first scent media to provide a first scent and a second scent cartridge comprising second scent media to provide a second scent; the actuation mechanism may be configured to selectively operate the valve mechanism to open and close a valve of a first valve assembly for the first scent cartridge and to open and close a valve of a second valve assembly for the second scent cartridge; a fan may be configured to provide air flow for the module; the actuation mechanism may be configured to direct air flow through the valve of the first valve assembly into the first scent cartridge and/or through the valve of the second valve assembly into the second scent cartridge. The actuation mechanism may comprise a cam mechanism configured to selectively operate the valve mechanism to open and close a valve of the first valve assembly for the first scent cartridge and to open and close a valve of the second valve assembly of the second scent cartridge. The module may be configured to provide the first scent during air flow through the first scent cartridge and the second scent during air flow through the second scent cartridge. The first scent cartridge may be sealed from air flow during air flow through the second scent cartridge and the second scent cartridge may be sealed from air flow during air flow through the first scent cartridge. The first valve assembly may comprise a set of valves; the second valve assembly may comprise a set of valves. The system may comprise a control system for the module; the control system may comprise a controller for the module; the controller may be configured to operate at least one of the actuation mechanism and/or a fan. The controller may be operated through a user interface. The system may be operated in a vehicle by a process comprising the steps of: (a) activating a user interface for the module; (b) detecting a cartridge in the module; the user interface of the module may comprise control of at least one of (1) selection of scent; (2) operation of a fan; (3) display of information; (4)

replacement of a cartridge; (5) cancel of a command; (6) shut off of the module. The system may comprise at least one cartridge; the at least one cartridge may comprise a first scent cartridge comprising first scent media and a first valve assembly and a second scent cartridge comprising second scent media and a second valve assembly; the valve mechanism may comprise the first valve assembly and the second valve assembly; the actuation mechanism may be configured to actuate the valve mechanism. The system may be configured to provide the first scent during air flow through the first scent cartridge and the second scent during air flow through the second scent cartridge; the first scent cartridge may be sealed from air flow during air flow through the second scent cartridge and the second scent cartridge may be sealed from air flow during air flow through the first scent cartridge. The system may be operated by a process comprising the step of obtaining data from the vehicle for a controller of the module; the data may comprise data from the vehicle interior; the step of detecting a cartridge may comprise obtaining data from an identification tag on the at least one cartridge. The system may comprise an interface; the interface may comprise at least one of a data/network interface and a mechanical interface. The system may comprise a vehicle interior component comprising the module.

The present invention also relates to a cartridge for a component for a vehicle interior configured to dispense scent from scent media into air in a vehicle interior comprising a body providing a chamber configured to contain scent media and a valve mechanism. The body may comprise an inlet port and an outlet port to facilitate air flow across scent media in the chamber; the valve mechanism may be configured to be actuated between a sealed position to prevent air flow for scent media in the chamber and an open position to facilitate air flow for scent media in the chamber. The cartridge may be configured for installation into a scent-dispensing apparatus for the vehicle interior comprising a module providing an inlet and an outlet and an actuator for the valve mechanism; so that when the valve mechanism is actuated to the open position by the actuator of the module scent is dispensed by air flow into the inlet of the module across scent media in the chamber from the outlet of the module into the vehicle interior. The actuator of the module may be configured to actuate the valve mechanism to the sealed position to prevent scent from being dispensed from the chamber into the vehicle interior. The body may comprise a cap and a bottom; the cap and the bottom comprise an outlet port and an inlet port. The valve mechanism may comprise a valve and a seal between the inlet port and the outlet port; at least one of the valve or the seal may be configured to seal at least one of (1) the inlet port to prevent passage of air through the inlet port; (2) the outlet port to prevent passage of air through the outlet port. The valve may comprise a valve for the inlet port and a valve for the outlet port; the seal may comprise a seal for the inlet port and a seal for the outlet port. The valve mechanism may comprise a member to couple the valve for the inlet port to the valve for the outlet port. The valve mechanism may comprise a spring configured to bias the valve mechanism to the sealed position; the spring may be configured to compress when the valve mechanism moves from the sealed position to the open position.

The present invention relates to a system configured to dispense scent into a vehicle interior comprising a module comprising an inlet and an outlet and configured to dispense scent through actuation of a valve mechanism; and an actuation mechanism for the module. The module may be configured to contain at least one cartridge comprising scent media so that the scent from the scent media is dispensed at the outlet of the module into the vehicle interior. The valve mechanism may comprise at least one valve configured as a flow control element between the inlet and the outlet. The actuation mechanism may be configured to actuate the valve mechanism. The system may comprise at least one cartridge. The at least one cartridge may comprise a valve configured to be actuated by the valve mechanism. The valve mechanism may comprise a set of valves. The at least one cartridge may be removable from the module. The at least one cartridge may be replaceable within the module. The at least one cartridge may comprise a set of cartridges. The set of cartridges may comprise a first scent cartridge comprising first scent media to provide a first scent and a second scent cartridge comprising second scent media to provide a second scent. The set of cartridges may comprise a third scent cartridge comprising third scent media to provide a third scent. The actuation mechanism may be configured to actuate the valve mechanism; the valve mechanism may comprise a first valve assembly for the first scent cartridge and a second valve assembly for the second scent cartridge. The actuation mechanism may be configured to actuate the first scent cartridge and the second scent cartridge. The actuation mechanism may be configured to actuate a valve of the first valve assembly and a valve of the second valve assembly. The actuation mechanism may comprise a cam mechanism. The actuation mechanism may comprise a cam mechanism operated by a controller. The at least one cartridge may comprise a first scent cartridge comprising first scent media and a first valve assembly and a second scent cartridge comprising second scent media and a second valve assembly; the valve mechanism may comprise the first valve assembly and the second valve assembly; the actuation mechanism may comprise a cam mechanism configured to actuate the valve mechanism. The cam mechanism may be configured to selectively open and close a valve of the first valve assembly for the first scent cartridge and to selectively open and close a valve of the second valve assembly of the second scent cartridge. The cam mechanism may be configured to selectively open and close a set of valves of the first valve assembly for the first scent cartridge and to selectively open and close a set of valves of the second valve assembly of the second scent cartridge. The actuation mechanism may be operated by a controller and configured to selectively operate the valve mechanism to open and close a valve of the first valve assembly for the first scent cartridge and to open and close a valve of the second valve assembly of the second scent cartridge. The system may comprise a fan configured to provide air flow through the module. The valve mechanism may comprise at least one valve; the fan may be configured to provide air flow through at least one valve. The system may comprise at least one cartridge; the at least one cartridge may comprise a first scent cartridge comprising first scent media and a first valve assembly and a second scent cartridge comprising second scent media and a second valve assembly; the valve mechanism may comprise the first valve assembly and the second valve assembly; the actuation mechanism may be configured to actuate the valve mechanism. The actuation mechanism may be configured to selectively operate the valve mechanism to open and close a valve of the first valve assembly for the first scent cartridge and to open and close a valve of the second valve assembly of the second scent cartridge; a fan may be configured to provide air flow through the valve of the first valve assembly into the first scent cartridge and through the valve of the second valve assembly into the second scent cartridge. The actuation mechanism may comprise a cam mechanism configured to selectively operate the valve mechanism to open and close a valve of the first valve assembly for the first scent cartridge and to open and close a valve of the second valve assembly of the second scent cartridge; a fan may be configured to provide air flow through the valve of the first valve assembly into the first scent cartridge and through the valve of the second valve assembly into the second scent cartridge. The system may be configured to provide the first scent during air flow through the first cartridge and the second scent during air flow through the second cartridge. The first cartridge may be sealed from air flow during air flow through the second cartridge and the second cartridge may be sealed from air flow during air flow through the first cartridge. The first valve assembly may comprise a set of valves; the second valve assembly may comprise a set of valves. The first valve assembly may comprise a set of valves; the second valve assembly may comprise a set of valves. The system may comprise a control system for the module. The control system may comprise a controller for the module. The controller may be configured to operate the actuation mechanism. The controller may be configured to operate the fan. The controller may be operated through a user interface. The system may comprise a user interface for the module. The system may be operated in a vehicle by a process comprising the steps of: (a) activating a user interface for the module; (b) detecting a cartridge in the module. The user interface of the module may comprise control of at least one of (1) selection of scent; (2) operation of a fan; (3) display of information; (4) replacement of a cartridge; (5) cancel of a command; (6) shut off of the module. The system may comprise at least one cartridge; the at least one cartridge may comprise a first scent cartridge comprising first scent media and a first valve assembly and a second scent cartridge comprising second scent media and a second valve assembly; the valve mechanism may comprise the first valve assembly and the second valve assembly; the actuation mechanism may be configured to actuate the valve mechanism. The fan may be configured to provide air flow through the valve of the first valve assembly into the first scent cartridge and through the valve of the second valve assembly into the second scent cartridge. The system may be configured to provide the first scent during air flow through the first cartridge and the second scent during air flow through the second cartridge. The first cartridge may be sealed from air flow during air flow through the second cartridge and the second cartridge may be sealed from air flow during air flow through the first cartridge. The system may be operated by a process further comprising the step of obtaining data from the vehicle for the controller of the module; the data may comprise data from the vehicle interior. The at least one cartridge may comprise an identification tag; data may comprise data from the identification tag. The system may comprise an interface; the interface may comprise at least one of a data/network interface and a mechanical interface. The system may comprise a power supply for the actuation mechanism. The system may comprise a vehicle interior component comprising the module. The vehicle interior component may comprise at least one of (a) a console; (b) an overhead console; (c) a floor console.

The present invention relates to a component for a vehicle interior configured to dispense scent from scent media into air in a vehicle interior and may comprise an inlet; an outlet; an enclosure configured for at least one scent-containing cartridge arrangement providing scent media (e.g. media contained within the body of the cartridge); and an actuator configured to actuate at least one scent-containing cartridge arrangement between a sealed state and an unsealed state (e.g. through a valve arrangement configured to open and close). The at least one scent-containing cartridge arrangement may comprise a first scent-containing cartridge arrangement and a second scent-containing cartridge arrangement. The at least one scent-containing cartridge arrangement may comprise a third scent-containing cartridge arrangement. The at least one scent-containing cartridge arrangement may comprise a fourth scent-containing cartridge arrangement. The actuator may be configured for (a) a bypass state with the first scent-containing cartridge arrangement in a sealed state and the second scent-containing cartridge arrangement in a sealed state and the third scent-containing cartridge arrangement in a sealed state and the fourth scent-containing cartridge arrangement in a sealed state; (b) a first actuation state actuating the first scent-containing cartridge arrangement in an unsealed state with the second scent-containing cartridge arrangement in the sealed state and the third scent-containing cartridge arrangement in a sealed state and the fourth scent-containing cartridge arrangement in the sealed state; (c) a second actuation state actuating the second scent-containing cartridge arrangement in an unsealed state with the first scent-containing cartridge arrangement and the third scent-containing cartridge arrangement in the sealed state and the fourth scent-containing cartridge arrangement in the sealed state; (d) a third actuation state actuating the third scent-containing cartridge arrangement in an unsealed state with the first scent-containing cartridge arrangement and the second scent-containing cartridge arrangement in the sealed state and the fourth scent-containing cartridge arrangement in the sealed state; (e) a fourth actuation state actuating the fourth scent-containing cartridge arrangement in an unsealed state with first scent-containing cartridge arrangement, the second scent-containing cartridge arrangement and the third scent-containing cartridge arrangement in the sealed state. The actuator/mechanism may comprise a motor and a slider arrangement and may be configured for (a) a position to provide the bypass state; (b) a position to provide the first actuation state; (c) a position to provide the second actuation state; (d) a position to provide the third actuation state; (e) a position to provide the fourth actuation state. The actuator may comprise (a) a cam/follower arrangement to operate a valve arrangement for the first cartridge arrangement; (b) a cam/follower arrangement to operate a valve arrangement for the second cartridge arrangement; (c) a cam/follower arrangement to operate a valve arrangement for the third cartridge arrangement; (d) a cam/follower arrangement to operate a valve arrangement for the fourth cartridge arrangement. The component may comprise a latch configured for (a) a latched state to secure the at least one cartridge arrangement; (b) an unlatched state to present the at least one cartridge arrangement for replacement. The component may comprise at least one plunger and at least one spring configured to present the at least one cartridge arrangement for replacement. The component may comprise a catch. The latch may be configured to secure the at least one cartridge arrangement at the catch. The actuator/mechanism may comprise a motor and a cam shaft and may be configured for (a) a position to provide the bypass state; (b) a position to provide an actuation state. The actuator may be configured to rotate to operate a valve arrangement for a cartridge arrangement. The cartridge may comprise an inlet port and an outlet port. The inlet port may be positioned at a bottom surface of the cartridge and the outlet port may be positioned at a rear surface of the cartridge. The inlet port may be positioned at a bottom surface of the cartridge and the outlet port may be positioned at a top surface of the cartridge generally opposite the bottom surface of the cartridge. The inlet port may be positioned at a bottom surface of the cartridge and the outlet port may be positioned at a bottom surface of the cartridge.

The present invention relates to a component for a vehicle interior configured to dispense scent from scent media into air in a vehicle interior comprising an inlet; an outlet; an enclosure configured for at least one scent cartridge providing scent media; and an actuator configured to actuate at least one scent cartridge between a sealed state and an unsealed state. The at least one scent cartridge may comprise a first scent cartridge and a second scent cartridge. The actuator may be configured for (a) a bypass state with the first scent cartridge in a sealed state and the second scent cartridge in a sealed state; (b) a first actuation state actuating the first scent cartridge in an unsealed state with the second scent cartridge in the sealed state; (c) a second actuation state actuating the second scent cartridge in an unsealed state with the first scent cartridge in the sealed state. The actuator may comprise (a) an actuator for the first scent cartridge; (b) an actuator for the second scent cartridge. The actuator may comprise a cam shaft configured to (a) actuate the first scent cartridge from the sealed state to the unsealed state to allow passage of air through scent media of the first scent cartridge toward the outlet; (b) actuate the second scent cartridge from the sealed state to the unsealed state to allow passage of air through scent media of the second scent cartridge toward the outlet. The cam shaft may be configured for (a) a position to provide the bypass state; (b) a position to provide the first actuation state; (c) a position to provide the second actuation state. The component may comprise a cover configured for (a) a closed state to conceal the at least one scent cartridge; (b) an open state to expose the at least one scent cartridge. When the cover is in the open state, the actuator may be configured for at least one of (a) an inaccessible state with the first scent cartridge in an inaccessible position and the second scent cartridge in an inaccessible position; (b) a first accessible state actuating the first scent cartridge in an accessible position for replacement with the second scent cartridge in the inaccessible position; (c) a second accessible state actuating the second scent cartridge in an accessible position for replacement with the first scent cartridge in the inaccessible position. The component may comprise a spring configured to move the first scent cartridge and the second scent cartridge to an accessible position for replacement in response to movement of the cover from the closed state to the open state. The cover may be configured to compress the spring in the closed state. The component may comprise a release mechanism configured to move the at least one scent cartridge to an accessible position for replacement in response to an external force applied to at least one scent cartridge when the cover is in the open state. The component may comprise a cover configured for (a) a closed state to conceal the at least one scent cartridge; (b) an open state to expose the at least one scent cartridge; the cover may comprise the outlet. The component may comprise an inlet duct and an outlet duct. The inlet duct may be separated from outlet duct by the enclosure. The component may comprise a cover for the at least one scent cartridge; the cover may be configured to form the outlet duct. The actuator may be positioned at an end of the inlet duct. The component may comprise a fan. The fan may be configured to direct air (a) to the inlet duct; (b) through scent media of the at least one scent cartridge; (c) through the outlet duct; (d) to the outlet. The component may comprise a bypass duct; the fan may be configured to direct air (a) to the inlet duct; (b) through the bypass duct; (c) through the outlet duct; (d) to the outlet. The fan may be configured to direct air (a) to the inlet duct; (b) through the bypass duct and through scent media of the at least one scent cartridge; (c) through the outlet duct; (d) to the outlet. The fan may be configured for at least one of (a) an off state; (b) an on state. The fan may be configured for (a) a high speed state; (b) a low speed state to provide (1) a high intensity scent dispersion; (2) a low intensity scent dispersion. The fan may be positioned at an end of the inlet duct. The actuator may be configured to compress a spring of the at least one scent cartridge to actuate the at least one scent cartridge from the sealed state to the unsealed state to allow passage of air through the scent media toward the outlet. The component may comprise at least one of: (a) a console; (b) an overhead console; (c) a floor console; (d) a center console.

The present invention relates to a system for a vehicle interior configured to dispense scent from scent media contained in at least one cartridge into air in a vehicle interior comprising an inlet and an outlet and an enclosure configured for at least one cartridge providing scent media and an actuator configured to actuate at least one cartridge between a sealed state and an unsealed state and a user interface. The user interface may be configured to facilitate the selection of scent by selection of at least one cartridge for actuation; the user interface may be configured for selection of intensity of scent from at least one cartridge.

The present invention relates to an apparatus for a vehicle interior configured to dispense scent from scent media contained in at least one cartridge into air in a vehicle interior. The apparatus may comprise an inlet and an outlet and a chamber configured for at least one scent cartridge providing scent media and an actuator configured to actuate at least one cartridge between a sealed state and an unsealed state; scent is dispensed from the outlet by selection of the at least one cartridge.

The present invention relates to a module for a vehicle interior configured to dispense scent from scent media contained in at least one interchangeable cartridge into air in a vehicle interior comprising an enclosure configured for at least one interchangeable scent-dispensing cartridge comprising scent media and an actuator configured to actuate at least one cartridge to dispense scent and an interface between the at least one cartridge and the enclosure; the chamber is configured so that at least one cartridge can be removed and replaced with at least one cartridge; the interface may comprise at least one of a data/network interface and a mechanical interface.

The present invention relates to a cartridge system for a scent-dispensing apparatus configured to dispense scent from scent media into air in a vehicle interior. The cartridge system may comprise a cartridge comprising a body providing a chamber for scent media and a valve assembly configured to provide an inlet port and an outlet port; the valve assembly may be configured to provide flow of air from the inlet port across scent media to the outlet port when open and to provide a seal of the chamber of the body when closed. The cartridge system may comprise a tag for data/information. The seal may comprise an air-tight leak-proof seal. The cartridge system may further comprise a cap for the body to be removed to fill/refill the chamber of the body with scent media.

The present invention relates to a component for a vehicle interior providing an inlet and an outlet configured for an open position to allow passage of air from the inlet to the outlet and a closed position to prevent passage of air from the inlet to the outlet. The component may comprise an enclosure; a screen within the enclosure; a valve mechanism within the enclosure; and scent media within the enclosure; the valve mechanism may be configured to move within the enclosure between a sealed position and an open position. The enclosure may comprise a cap and a bottom. The cap may comprise one of the outlet; the inlet; the bottom may comprise the other of the outlet; the inlet. One of (a) the cap; (b) the bottom may comprise the outlet and the inlet. The valve mechanism may comprise a valve and a seal; at least one of (a) the valve; (b) the seal may be configured to seal at least one of (1) the inlet to prevent passage of air through the inlet; (2) the outlet to prevent passage of air through the outlet. The valve may comprise a set of valves; the seal may comprise a set of seals. The valve may comprise a valve for the inlet and a valve for the outlet; the seal may comprise a seal for the inlet and a seal for the outlet. The valve mechanism may comprise a stem configured couple movement of the valve for the inlet; the valve for the outlet; the seal for the inlet; the seal for the outlet. The valve for the inlet may be configured to move relative to the valve for the outlet. The valve mechanism may comprise a spring for the inlet and a spring for the outlet. At least one of (a) the spring for the inlet; (b) the spring for the outlet may be configured to compress when the valve mechanism moves from the sealed position to the open position. The spring for the inlet and the spring for the outlet may be configured to compress when the valve mechanism moves from the sealed position to the open position. The valve mechanism may be configured for movement to a transitional position to (1) allow passage of air through the inlet and (2) prevent passage of air through the outlet. The valve mechanism may comprise a spring configured to bias the valve mechanism in the sealed position. The spring may be configured to compress when the valve mechanism moves from the sealed position to the open position. The valve mechanism may comprise a valve. The spring may be configured to bias the valve. The valve may be configured to compress the spring. The valve may comprise a set of valves. The screen may comprise at least one aperture. The screen may be configured to position the scent media. The open position may comprise a gapped position.

The present invention relates to a cartridge system for a scent-dispensing apparatus configured to dispense scent from scent media into air in a vehicle interior comprising (a) a cartridge comprising a body providing a chamber for scent media; (b) a valve assembly configured to provide an inlet port and an outlet port. The valve assembly may be configured for (1) an enclosed state to provide a seal at the inlet port and a seal at the outlet port; (2) a transitional state to provide a seal at one of the inlet port and the outlet port and to provide flow of air through the other of the inlet port and the outlet port; (3) a pass-through state to provide flow of air through the inlet port across scent media through the outlet port. The valve mechanism may comprise a valve and a seal; at least one of (a) the valve; (b) the seal may be configured to seal at least one of (1) the inlet to prevent passage of air through the inlet; (2) the outlet to prevent passage of air through the outlet. The valve may comprise a set of valves; the seal may comprise a set of seals. The valve may comprise a valve for the inlet and a valve for the outlet; the seal may comprise a seal for the inlet and a seal for the outlet. The valve for the inlet may be configured to move relative to the valve for the outlet. The valve mechanism may comprise a spring for the inlet and a spring for the outlet. At least one of (a) the spring for the inlet; (b) the spring for the outlet may be configured to compress when the valve mechanism moves from the enclosed state to the transitional state. The spring for the inlet and the spring for the outlet may be configured to compress when the valve mechanism moves from the enclosed state to the pass-through state.

The present invention relates to a cartridge system for a scent-dispensing apparatus configured to dispense scent from scent media into air in a vehicle interior comprising: (a) a cartridge comprising a body providing a chamber for scent media; (b) a valve assembly configured to provide an inlet port and an outlet port. The valve assembly may comprise an inlet valve configured to provide the inlet port and an outlet valve configured to provide the outlet port. The inlet valve may be configured (1) to move relative to the outlet port to provide flow of air from the inlet port across scent media to the outlet port when open and (2) to provide a seal of the chamber of the body when closed. The inlet valve may be configured to move the outlet valve to provide flow of air across scent media through the outlet port.

The present invention relates to a cartridge system for a scent-dispensing apparatus configured to dispense scent from scent media into air in a vehicle interior comprising: (a) a cartridge comprising a body providing a chamber for scent media; (b) a valve assembly configured to provide an inlet port and an outlet port. The valve assembly may comprise an inlet valve configured to provide the inlet port and an outlet valve configured to provide the outlet port. The body may comprise an inlet section and an outlet section. The inlet valve may be configured (1) to move relative to the outlet port to provide flow of air from the inlet port across scent media to the outlet port when open and (2) to provide a seal of the chamber of the body when closed. The inlet valve may be configured to move the outlet valve to provide flow of air across scent media through the outlet port. The inlet section may comprise the chamber for scent media and the outlet section may comprise an outlet chamber. The outlet section may comprise the outlet valve. The inlet section may comprise the inlet valve.

The present invention relates to a component for a vehicle interior configured to dispense scent from scent media into air in a vehicle interior comprising: an inlet; an outlet; an enclosure configured for at least one scent cartridge providing scent media; and an actuator configured to actuate at least one scent cartridge between a sealed state and an unsealed state. The at least one scent cartridge may comprise a first scent cartridge and a second scent cartridge. The actuator may comprise (a) an actuator for the first scent cartridge; (b) an actuator for the second scent cartridge. The actuator may be configured to (a) rotate in a first direction to actuate the first scent cartridge and (b) rotate in a second direction generally opposite the first direction to actuate the second scent cartridge. The actuator may be configured for (a) a default state with the first scent cartridge in a sealed state and the second scent cartridge in a sealed state; (b) a first actuation state actuating the first scent cartridge in an unsealed state with the second scent cartridge in the sealed state; (c) a second actuation state actuating the second scent cartridge in an unsealed state with the first scent cartridge in the sealed state. The actuator may comprise a shaft configured to (a) actuate the first scent cartridge from the sealed state to the unsealed state to allow passage of air through scent media of the first scent cartridge toward the outlet; (b) actuate the second scent cartridge from the sealed state to the unsealed state to allow passage of air through scent media of the second scent cartridge toward the outlet. The shaft may be configured for (a) a first position to provide the first actuation state; (b) a second position to provide the second actuation state; (c) a third position to provide the default state. The first position may comprise an extended position; the second position may comprise a retracted position; the third position may comprise a middle position. The component may comprise a motor configured to move the shaft between the first position; the second position; the third position. The shaft may be configured to translate to actuate an actuator to rotate to actuate the first scent cartridge. The actuator may comprise a seesaw mechanism. The seesaw mechanism may comprise an arm comprising (a) an actuator for the first scent cartridge; (b) an actuator for the second scent cartridge. The seesaw mechanism may comprise a motor and a shaft; the motor may be configured to move the shaft at an end of the arm to rotate the arm. The actuator may comprise an arm configured to rotate to actuate the at least one scent cartridge. The at least one scent cartridge may comprise a first scent cartridge and a second scent cartridge; the actuator may comprise a motor configured to pull the arm toward the motor to actuate the first scent cartridge; the motor may be configured to push the arm to actuate the second scent cartridge. The component may comprise a cover configured for (a) a closed state to conceal the at least one scent cartridge; (b) an open state to expose the at least one scent cartridge. The cover may comprise a mesh configured to conceal the at least one scent cartridge and allow air to pass through the outlet. The cover may comprise the outlet. The cover may comprise a magnet configured to couple the cover and the enclosure. The component may comprise an inlet chamber. The inlet chamber may be separated from the outlet by the enclosure. The component may comprise a cover for the at least one scent cartridge; the cover may be configured to form the outlet. The actuator may be positioned at an end of the inlet chamber. The component may comprise a fan. The fan may be configured to direct air (a) to the inlet chamber; (b) through scent media of the at least one scent cartridge; (c) through the outlet. The fan may be configured for at least one of (a) an off state; (b) an on state. The fan may be configured for (a) a high speed state; (b) a low speed state to provide (1) a high intensity scent dispersion; (2) a low intensity scent dispersion. The fan may be positioned at an end of the inlet chamber. The fan may comprise a first fan and a second fan. The fan may be configured for (1) a high intensity scent dispersion with the first fan on and the second fan on; (2) a low intensity scent dispersion with the first fan on and the second fan off. The at least one scent cartridge may comprise a first scent cartridge, a second scent cartridge, a third scent cartridge and a fourth scent cartridge; the first fan may be configured to direct air through scent media of the first scent cartridge and through scent media of the second scent cartridge; the second fan may be configured to direct air through scent media of the third scent cartridge and through scent media of the fourth scent cartridge. The actuator may be configured to compress a spring of the at least one scent cartridge to actuate the at least one scent cartridge from the sealed state to the unsealed state to allow passage of air through the scent media toward the outlet. The component may comprise at least one of: (a) a console; (b) an overhead console; (c) a floor console; (d) a center console; (e) a cup holder; (f) a module configured to mount within a cupholder.

The present invention relates to a system for a vehicle interior configured to dispense scent from scent media contained in at least one cartridge into air in a vehicle interior comprising: an inlet; an outlet; an enclosure configured for at least one cartridge providing scent media; an actuator configured to actuate at least one cartridge between a sealed state and an unsealed state; and a user interface. The user interface may be configured to facilitate the selection of scent by selection of at least one cartridge for actuation. The user interface may be configured for selection of intensity of scent from at least one cartridge.

The present invention relates to an apparatus for a vehicle interior configured to dispense scent from scent media contained in at least one cartridge into air in a vehicle interior comprising: an inlet; an outlet; a chamber configured for at least one scent cartridge providing scent media; and an actuator configured to actuate at least one cartridge between a sealed state and an unsealed state. The scent may be dispensed from the outlet by selection of the at least one cartridge.

The present invention relates to a module for a vehicle interior configured to dispense scent from scent media contained in at least one interchangeable cartridge into air in a vehicle interior comprising: an enclosure configured for at least one interchangeable scent-dispensing cartridge comprising scent media; an actuator configured to actuate at least one cartridge to dispense scent; and an interface between the at least one cartridge and the enclosure. The chamber may be configured so that at least one cartridge can be removed and replaced with at least one cartridge. The interface may comprise at least one of a data/network interface and a mechanical interface.

The present invention relates to a system for a vehicle interior configured to dispense scent from scent media contained in at least one cartridge into air in a vehicle interior comprising: an inlet; an outlet; an enclosure configured for at least one cartridge providing scent media; a valve mechanism configured to actuate at least one cartridge between a sealed state and an unsealed state; and a user interface. The user interface may be configured to facilitate the selection of scent by selection of at least one cartridge for actuation.

The present invention relates to an apparatus for a vehicle interior configured to dispense scent from scent media contained in at least one cartridge into air in a vehicle interior comprising: an inlet; an outlet; a chamber configured for at least one scent cartridge providing scent media; and a valve mechanism configured to actuate at least one cartridge between a sealed state and an unsealed state. The scent may be dispensed from the outlet by selection of the at least one cartridge.

The present invention relates to a module for a vehicle interior configured to dispense scent from scent media contained in at least one interchangeable cartridge into air in a vehicle interior comprising: an enclosure configured for at least one interchangeable scent-dispensing cartridge comprising scent media; a valve mechanism configured to actuate at least one cartridge to dispense scent; and an interface between the at least one cartridge and the enclosure. The chamber may be configured so that at least one cartridge can be removed and replaced with at least one cartridge; the interface may comprise at least one of a data/network interface and a mechanical interface. The valve mechanism may comprise an actuator. The valve mechanism may be configured to be operated by a power supply. The interface may comprise a user interface for a vehicle component. The valve mechanism may be configured to be operated by the user interface. The valve mechanism may comprise a valve arrangement.

FIGURES

FIGS. 8A and 8B are schematic perspective views of a component/apparatus for dispensing scent according to an exemplary embodiment.

FIG. 8C is a schematic rear view of a component/apparatus for dispensing scent according to an exemplary embodiment.

FIGS. 8D and 8E are schematic perspective views of an apparatus/system for dispensing scent with a cartridge according to an exemplary embodiment.

FIGS. 9A and 9B are schematic perspective views of a component/apparatus for dispensing scent according to an exemplary embodiment.

FIGS. 9C and 9D are schematic perspective views of an apparatus/system for dispensing scent with a cartridge according to an exemplary embodiment.

FIG. 12A is a schematic exploded perspective view of an apparatus/system for dispensing scent with a cartridge according to an exemplary embodiment.

FIGS. 12B and 12C are schematic perspective views of an apparatus/system for dispensing scent with a cartridge according to an exemplary embodiment.

FIGS. 13A and 13B are schematic perspective views of a component/apparatus for dispensing scent according to an exemplary embodiment.

FIG. 13C is a schematic perspective exploded view of a component/apparatus for dispensing scent according to an exemplary embodiment.

FIGS. 14A through 14F are schematic front views of a component/apparatus for dispensing scent according to an exemplary embodiment.

FIGS. 15A through 15F are schematic section views of a component/apparatus for dispensing scent according to an exemplary embodiment.

FIGS. 16A and 16B are schematic perspective views of a component/apparatus for dispensing scent according to an exemplary embodiment.

FIG. 16C is a schematic exploded perspective view of a component/apparatus for dispensing scent according to an exemplary embodiment.

FIGS. 17A and 17B are schematic section views of a component/apparatus for dispensing scent according to an exemplary embodiment.

FIGS. 17C and 17D are schematic partial section views of a component/apparatus for dispensing scent according to an exemplary embodiment.

FIGS. 18A and 18B are schematic perspective views of a component/apparatus for dispensing scent according to an exemplary embodiment.

FIGS. 18C and 18D are schematic perspective views of an apparatus/system for dispensing scent with a cartridge according to an exemplary embodiment.

FIGS. 23A through 23C are schematic front views of a component/apparatus for dispensing scent according to an exemplary embodiment.

FIGS. 28A and 28B are schematic perspective views of a component/apparatus for dispensing scent according to an exemplary embodiment.

FIGS. 28C and 28D are schematic perspective views of an apparatus/system for dispensing scent with a cartridge according to an exemplary embodiment.

FIG. 28E is a schematic exploded perspective view of an apparatus/system for dispensing scent with a cartridge according to an exemplary embodiment.

FIGS. 36A through 36C are schematic front views of a component/apparatus for dispensing scent according to an exemplary embodiment.

FIGS. 37A through 37C are schematic section views of a component/apparatus for dispensing scent according to an exemplary embodiment.

FIGS. 39A and 39B are schematic perspective views of an apparatus/system for dispensing scent with a cartridge according to an exemplary embodiment.

FIGS. 39C and 39D are schematic exploded perspective views of an apparatus/system for dispensing scent with a cartridge according to an exemplary embodiment.

FIG. 40 is a schematic exploded partial perspective view of an apparatus/system for dispensing scent with a cartridge according to an exemplary embodiment.

FIG. 42A is a schematic perspective view of an apparatus/system for dispensing scent with a cartridge according to an exemplary embodiment.

FIGS. 42B and 42C are schematic partial perspective views of an apparatus/system for dispensing scent with a cartridge according to an exemplary embodiment.

FIG. 42D is a schematic exploded perspective view of an apparatus/system for dispensing scent with a cartridge according to an exemplary embodiment.

FIG. 42E is a schematic exploded partial perspective view of an apparatus/system for dispensing scent with a cartridge according to an exemplary embodiment.

FIGS. 45A through 45D are schematic diagrams of a system comprising a component/apparatus for dispensing scent from a scent-dispensing cartridge/system according to an exemplary embodiment.

DESCRIPTION

Figure 1A:
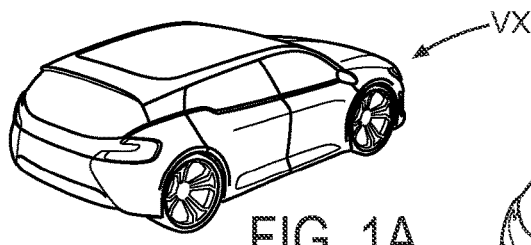
FIGS. 1A and 1B are schematic perspective views of a vehicle providing an interior according to an exemplary embodiment.
Figure 1B:
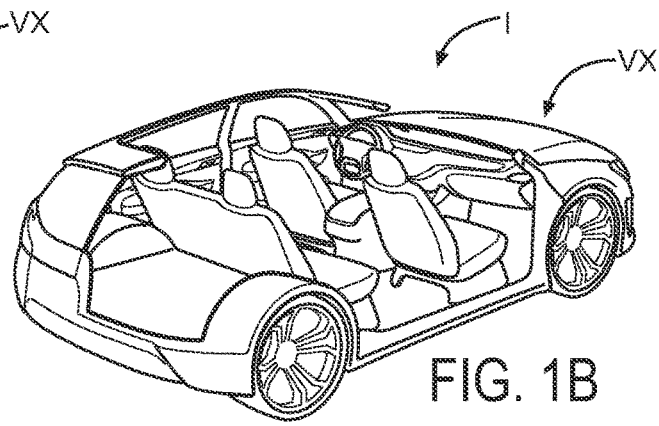
Figure 2:
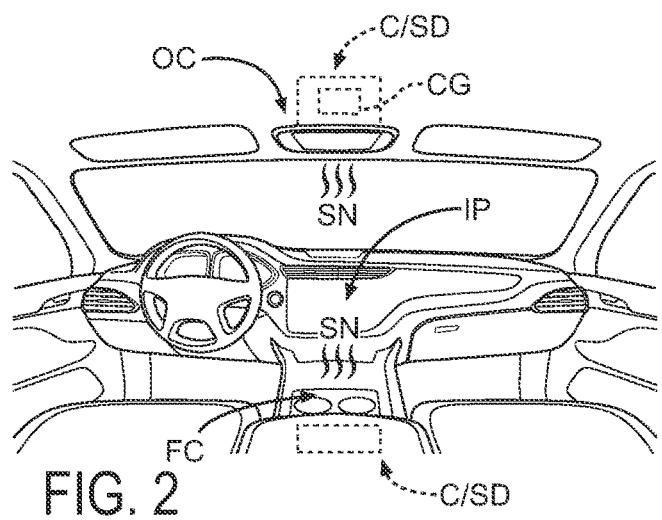
FIG. 2 is a schematic perspective view of a vehicle interior with a component comprising an apparatus/module for dispensing scent from a scent-dispensing cartridge/system according to an exemplary embodiment.

Referring to FIGS. 1A, 1B and 2, a vehicle VX providing an interior/interior space I is shown schematically according to an exemplary embodiment.

Figure 3:
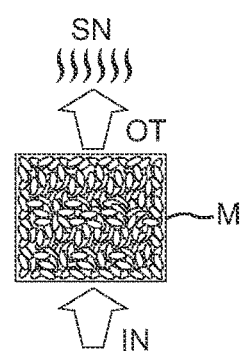
FIG. 3 is a schematic diagram of media for a cartridge for an apparatus for dispensing scent according to an exemplary embodiment.

As shown schematically in FIGS. 2 and 3, the vehicle interior may comprise a component C configured to dispense scent SN from scent media M into air in a vehicle interior. Component C may comprise a scent-dispensing apparatus SD. Component C may comprise an enclosure for an apparatus/system for dispensing scent SN configured with a cartridge CG that may contain scent media M to provide a scent SN (e.g. scented air comprising air containing/infused with scent media in a concentration to be perceptible) in the vehicle interior (e.g. when the apparatus with cartridge is actuated/in operation); the apparatus for dispensing scent SN may be configured for installation/assembly into component C. Component C may be configured for installation/assembly into a console (shown as floor console FC, overhead console OC, etc.) or panel (shown as instrument panel IP) or other trim panel/component.

As indicated schematically according to an exemplary embodiment in FIG. 2, the vehicle interior I may comprise a component C comprising an apparatus/module SD for dispensing scent from a scent-dispensing cartridge CG; the cartridge CG for the apparatus/module may comprise scent media M and a flow control element such as a valve mechanism/valve V and an information/data tag TG; scent SN is dispensed by airflow from inlet IN across scent media M to outlet OT. See FIGS. 3 and 4. As indicated schematically according to an exemplary embodiment in FIGS. 5A and 5B, the system/component C with module/apparatus SD for dispensing scent may comprise a user interface UI to operate a control system/controller for an actuator for selection/operation of each cartridge CG and a fan FN. See also FIGS. 45A-45D (schematic diagrams of a system comprising a component/apparatus for dispensing scent from a scent-dispensing cartridge/system according to an exemplary embodiment) and FIG. 46 (schematic flow diagram of operation of a component/apparatus for dispensing scent according to an exemplary embodiment). As shown schematically according to an exemplary embodiment in FIG. 2, the vehicle interior I may comprise the component C with scent-dispensing apparatus/module SD; as indicated schematically each cartridge CG containing scent media SM is fit within the apparatus/module SD with a fit/interconnection arrangement/interface for each cartridge so that scent from the scent media can be dispensed conveniently and effectively (e.g as selected and/or without leakage) from a selected cartridge/scent media through the component into an interior space such as a vehicle interior; each cartridge may be removable/replaceable in the module/apparatus. See also FIGS. 5A-5B, 45A-45D and 46. The component for a vehicle interior configured to dispense scent in a vehicle interior may comprise a scent-dispensing apparatus comprising a module configured for at least one scent-dispensing cartridge (removable/replaceable) containing scent media. See FIGS. 2 and 4. As indicated schematically in FIGS. 5A-5B and 13A-13D, an actuator may be configured to operate the module in a bypass mode or for selection/actuation of a cartridge; a selected cartridge may be actuated from a sealed state to prevent airflow through scent media to an unsealed state to allow airflow across/through scent media and from the outlet of the module into the vehicle interior. As indicated schematically, the actuator may comprise a mechanism (e.g. slider, cam mechanism; etc.); each cartridge may comprise a valve mechanism actuated by the actuator; each mechanism may comprise a spring. See e.g. FIGS. 27A-27B, 38A-38B and 45A-45D. As shown schematically in FIGS. 5A-5B, the module may comprise a fan to provide airflow. As shown schematically, the component may provide a user interface.

According to an exemplary embodiment as shown schematically in FIGS. 1A-1B, 2, 3, 4, 5A-5B and 45A-45D, a vehicle interior component C may comprise a system comprising a module SD configured to dispense scent into the vehicle interior space; the module may comprise an inlet IN and an outlet OT and configured to dispense scent from scent media M in a cartridge CG through actuation of a valve mechanism V/VM; and an actuation mechanism AC for the module. See also FIGS. 11A-11D, 19A-19B, 21A-21C, 22D, 23A-23C, 25A-25C, 27A-27B, 30A-30B, 36A-36C, 37A-37C, 38A-38B, 39A-39D, 41A-41D, 43A-43D and 46. As shown schematically, the module may be configured to contain at least one cartridge comprising scent media so that the scent from the scent media is dispensed at the outlet of the module into the vehicle interior; the valve mechanism may comprise at least one valve configured as a flow control element (e.g. valve/seal, etc.) between the inlet and the outlet; the actuation mechanism may be configured to actuate the valve mechanism. As shown schematically, each cartridge may comprise a valve configured to be actuated by the valve mechanism; the valve mechanism may comprise a set of valves; each cartridge may be removable from the module; the at least one cartridge may be replaceable within the module. See e.g. FIG. 46. As shown schematically in FIGS. 5A-5B, 27A-27B, 38A-38B and 45A-45D, the at least one cartridge may comprise a first scent cartridge comprising first scent media and a first valve assembly and a second scent cartridge comprising second scent media and a second valve assembly; the valve mechanism may comprise the first valve assembly and the second valve assembly; the cartridge system CG may comprise a set of cartridges; the set of cartridges may comprise a first scent cartridge comprising first scent media to provide a first scent and a second scent cartridge comprising second scent media to provide a second scent; the set of cartridges may comprise a third scent cartridge comprising third scent media to provide a third scent. As shown schematically in FIGS. 27A-27B, 38A-38B and 45A-45D, the actuation mechanism AC may be configured to actuate the valve mechanism VM/V; the valve mechanism may comprise a first valve assembly for the first scent cartridge and a second valve assembly for the second scent cartridge; the actuation mechanism may be configured to actuate the first scent cartridge and the second scent cartridge. As shown schematically, the actuation mechanism AC may be configured to actuate a valve of the first valve assembly and a valve of the second valve assembly; the actuation mechanism may comprise a cam mechanism (e.g. operated by a controller). See e.g. FIGS. 10A-10D, 13A-13C, 14A-14F, 15A-15F, 16A-16C and 45A-45D. As indicated schematically according to an exemplary embodiment in FIG. 46, the module with actuation mechanism may be configured to selectively open and close a valve of the first valve assembly for the first scent cartridge and to selectively open and close a valve of the second valve assembly of the second scent cartridge; the mechanism may be configured to selectively open and close a set of valves of the first valve assembly for the first scent cartridge and to selectively open and close a set of valves of the second valve assembly of the second scent cartridge. See e.g. FIGS. 4, 5A, 11A-11D, 19A-19B, 21A-21C, 22D, 23A-23C, 25A-25C, 27A-27B, 30A-30B, 36A-36C, 37A-37C, 38A-38B, 39A-39D, 41A-41D, 43A-43D and 45A-45D.

As shown schematically in FIGS. 6A-6C, 10A-10D, 11A-11D, 12A-12C, 13A-13C, 14A-14F, 15A-15F, 16A-16C, and 17A-17D, a component C for a vehicle interior configured to dispense scent SN from scent media M into air in a vehicle interior may comprise an inlet IN; an outlet OT; an enclosure EN configured for at least one scent-containing cartridge arrangement CG providing scent media M (e.g. media contained within the body of the cartridge); and an actuator AC configured to actuate at least one scent-containing cartridge arrangement CG between a sealed state and an unsealed state (e.g. through a valve arrangement VA/VB configured to open and close). The at least one scent-containing cartridge arrangement CG may comprise a first scent-containing cartridge arrangement CG1 and a second scent-containing cartridge arrangement CG2. The at least one scent-containing cartridge arrangement CG may comprise a third scent-containing cartridge arrangement CG3. The at least one scent-containing cartridge arrangement CG may comprise a fourth scent-containing cartridge arrangement CG4.

Actuator AC may be configured for (a) a bypass state with first scent-containing cartridge arrangement CG1 in a sealed state and second scent-containing cartridge arrangement CG2 in a sealed state and third scent-containing cartridge arrangement CG3 in a sealed state and fourth scent-containing cartridge arrangement CG4 in a sealed state as shown schematically in FIGS. 14B and 15B; (b) a first actuation state actuating first scent-containing cartridge arrangement CG1 in an unsealed state with second scent-containing cartridge arrangement CG2 in the sealed state and third scent-containing cartridge arrangement CG3 in a sealed state and fourth scent-containing cartridge arrangement CG4 in the sealed state as shown schematically in FIGS. 14C and 15C; (c) a second actuation state actuating second scent-containing cartridge arrangement CG2 in an unsealed state with first scent-containing cartridge arrangement CG1 and third scent-containing cartridge arrangement CG3 in the sealed state and fourth scent-containing cartridge arrangement CG4 in the sealed state as shown schematically in FIGS. 14D and 15D; (d) a third actuation state actuating third scent-containing cartridge arrangement CG3 in an unsealed state with first scent-containing cartridge arrangement CG1 and second scent-containing cartridge arrangement CG2 in the sealed state and fourth scent-containing cartridge arrangement CG4 in the sealed state as shown schematically in FIGS. 14E and 15E; (e) a fourth actuation state actuating fourth scent-containing cartridge arrangement CG4 in an unsealed state with first scent-containing cartridge arrangement CG1, second scent-containing cartridge arrangement CG2 and third scent-containing cartridge arrangement CG3 in the sealed state as shown schematically in FIGS. 14F and 15F.

Actuator/mechanism AC may comprise a motor MR and a slider arrangement SL as shown schematically in FIG. 13C and may be configured for (a) a position to provide the bypass state as shown schematically in FIGS. 14A, 14B, 15A and 15B; (b) a position to provide the first actuation state as shown schematically in FIGS. 14C and 15C; (c) a position to provide the second actuation state as shown schematically in FIGS. 14D and 15D; (d) a position to provide the third actuation state as shown schematically in FIGS. 14E and 15E; (e) a position to provide the fourth actuation state as shown schematically in FIGS. 14F and 15F. Actuator AC may comprise (a) a cam/follower arrangement CM1/CF1 to operate a valve arrangement for first cartridge arrangement CG1; (b) a cam/follower arrangement CM2/CF2 to operate a valve arrangement for second cartridge arrangement CG2; (c) a cam/follower arrangement CM3/CF3 to operate a valve arrangement for third cartridge arrangement CG3; (d) a cam/follower arrangement CM4/CF4 to operate a valve arrangement for fourth cartridge arrangement CG4.

Figure 10A:
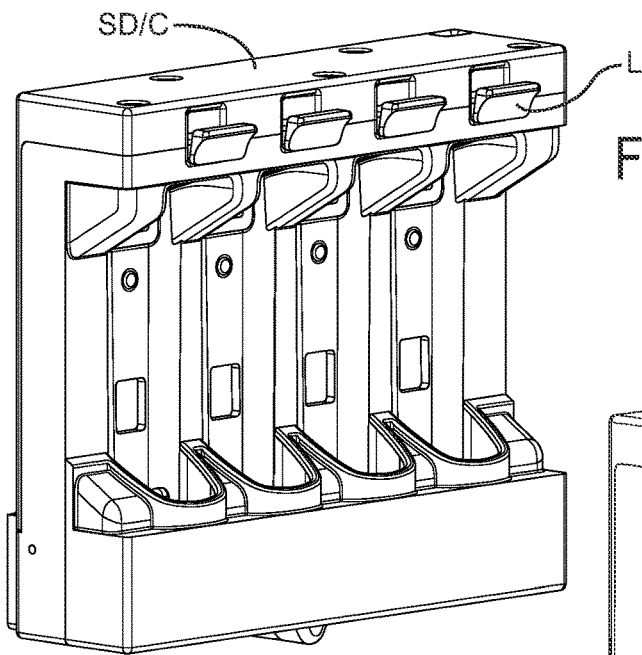
FIGS. 10A through 10D are schematic perspective views of a component/apparatus for dispensing scent according to an exemplary embodiment.
Figure 10B:
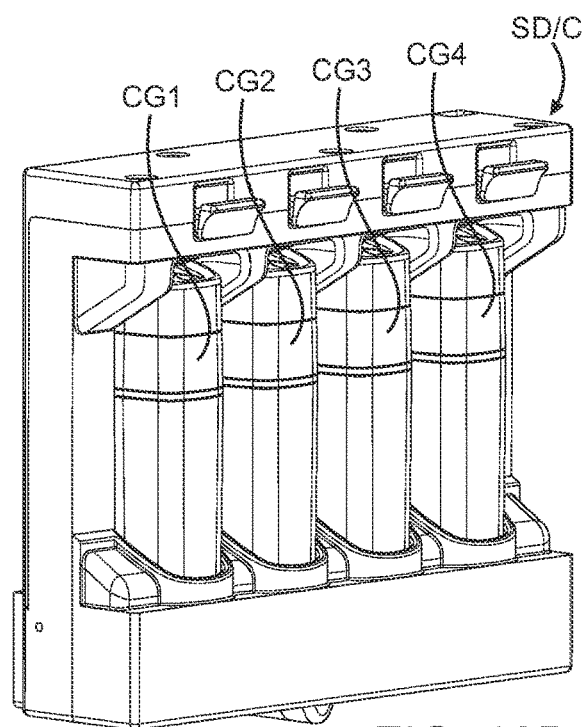
Figure 10C:
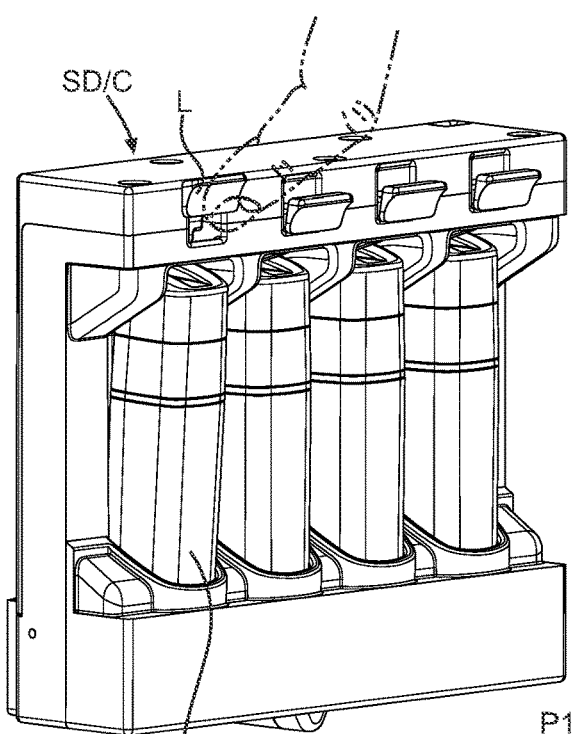
Figure 10D:
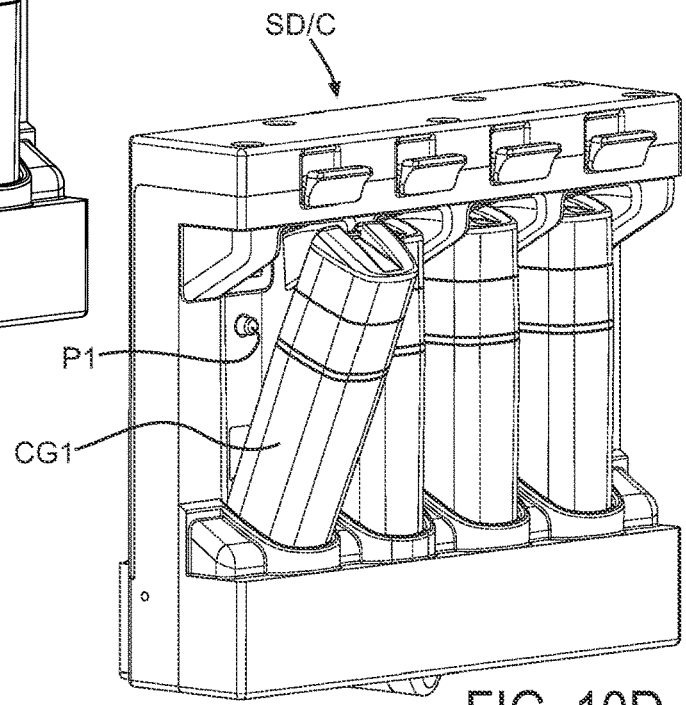
Figure 11A:
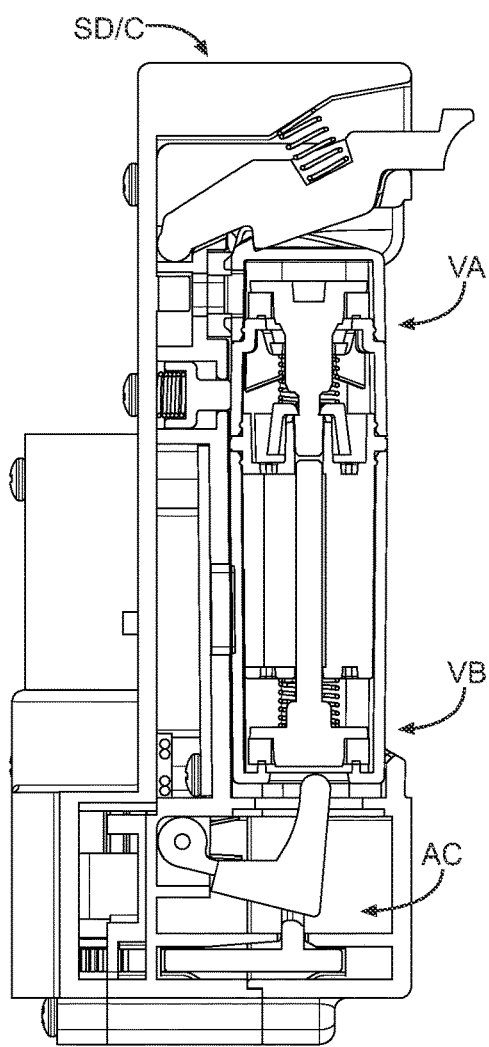
FIGS. 11A and 11B are schematic section views of a component/apparatus for dispensing scent according to an exemplary embodiment.
Figure 11B:
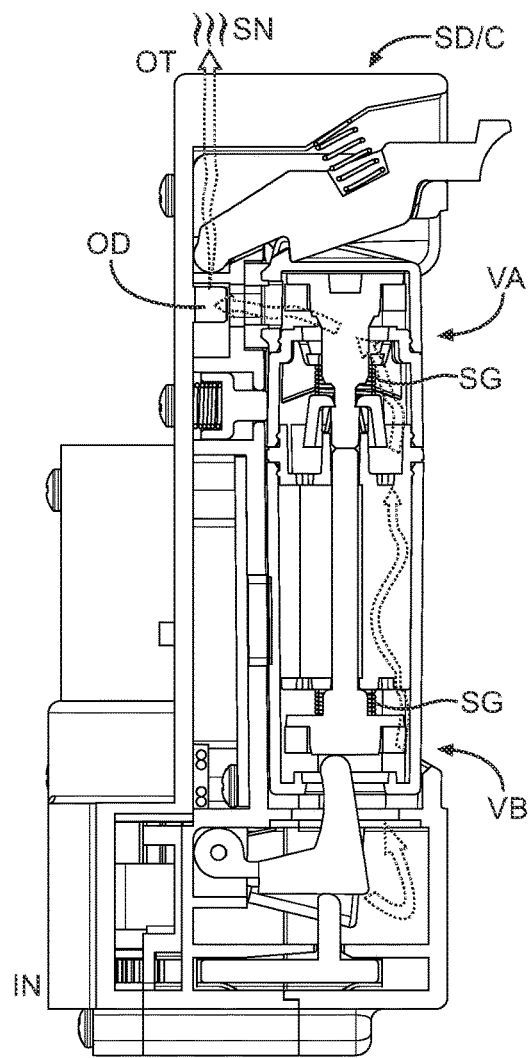
Figure 11C:
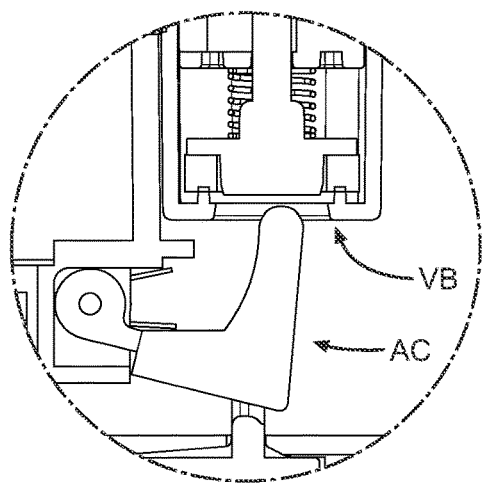
FIGS. 11C and 11D are schematic partial section views of a component/apparatus for dispensing scent according to an exemplary embodiment.
Figure 11D:
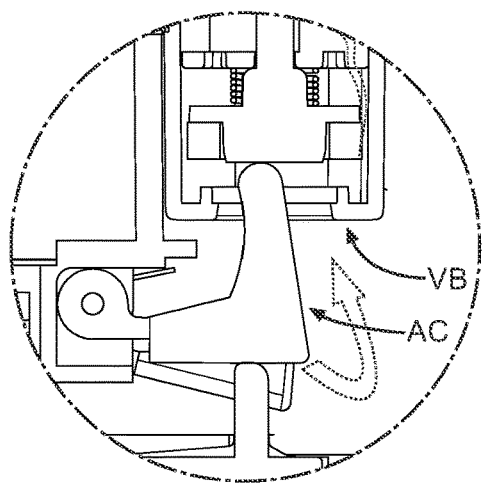
Figure 19A:
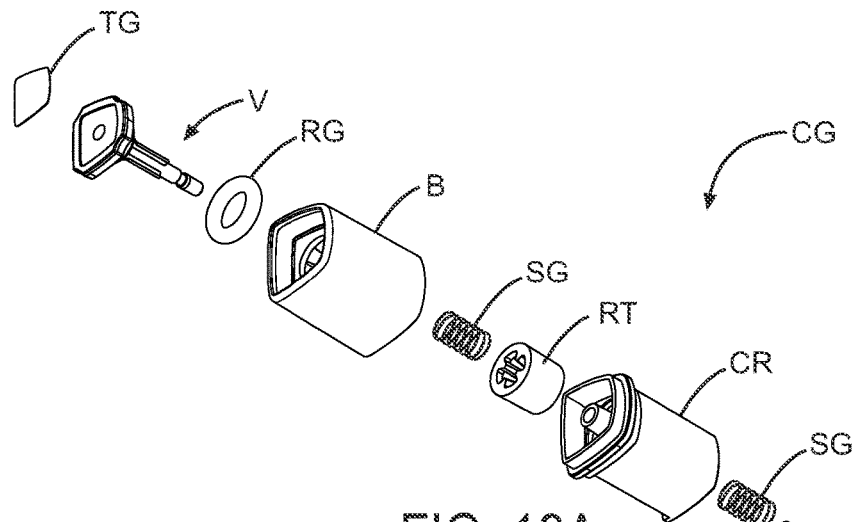
FIGS. 19A and 19B are schematic exploded perspective views of an apparatus/system for dispensing scent with a cartridge according to an exemplary embodiment.
Figure 19B:
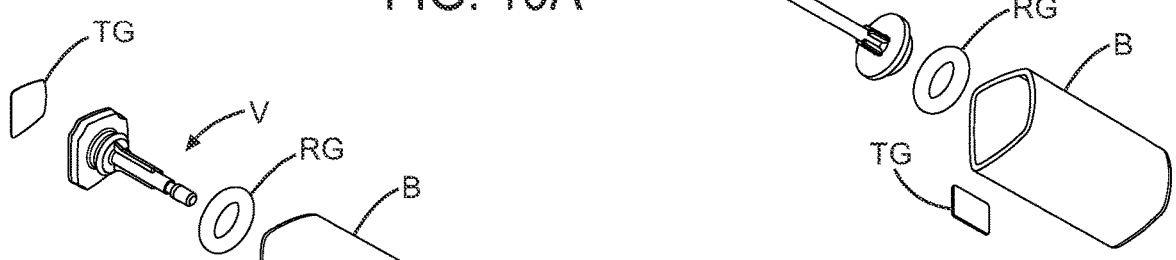
Figure 20:
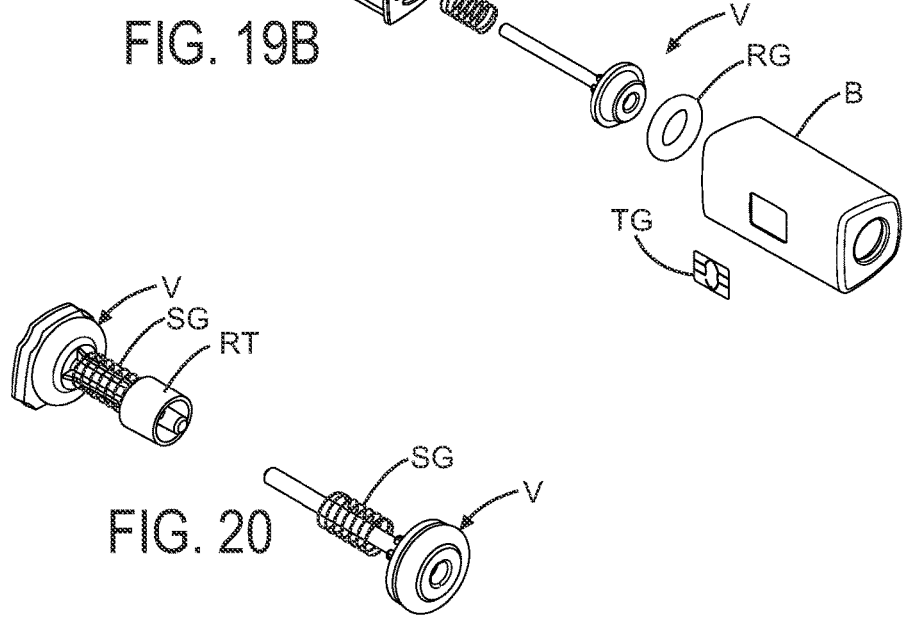
FIG. 20 is a schematic exploded partial perspective view of an apparatus/system for dispensing scent with a cartridge according to an exemplary embodiment.
Figure 21A:
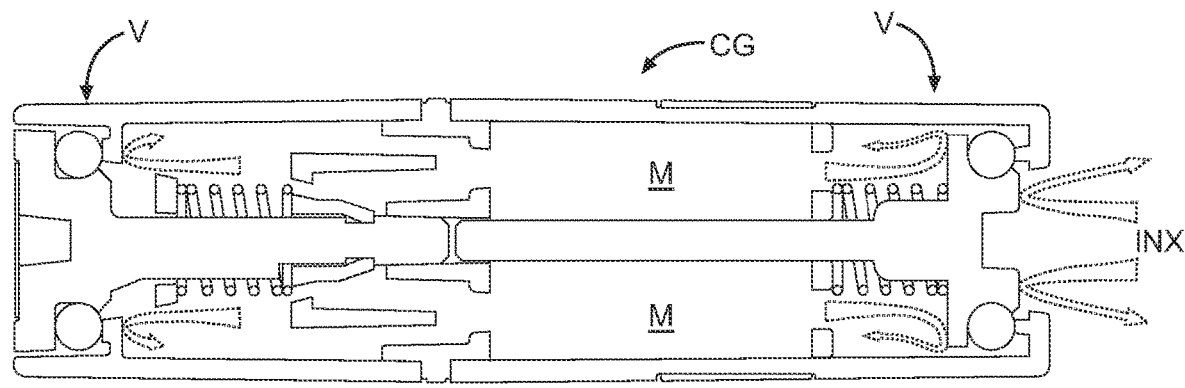
FIGS. 21A through 21C are schematic section views of an apparatus/system for dispensing scent with a cartridge according to an exemplary embodiment.
Figure 21B:
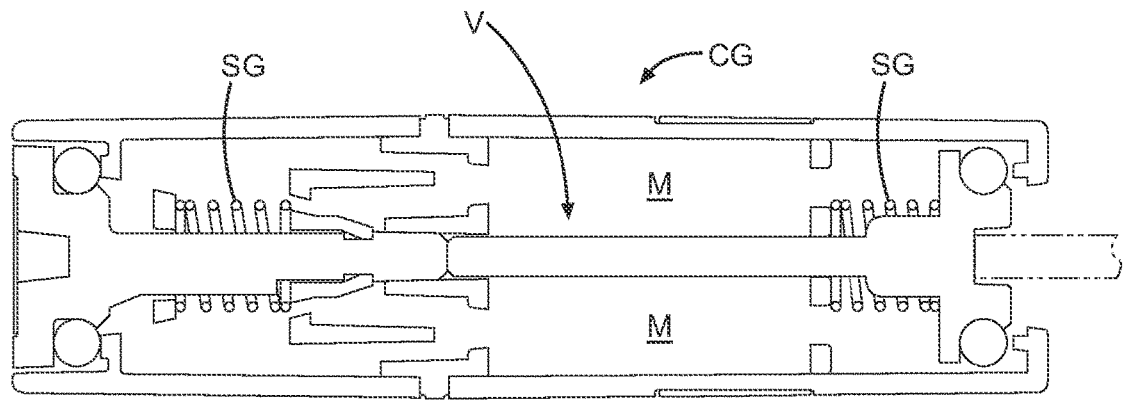
Figure 21C:
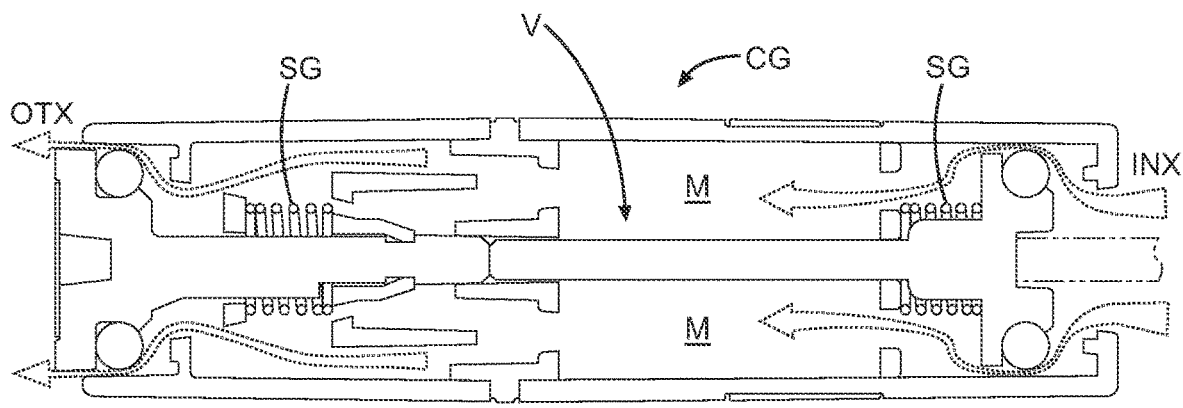
Figure 22A:
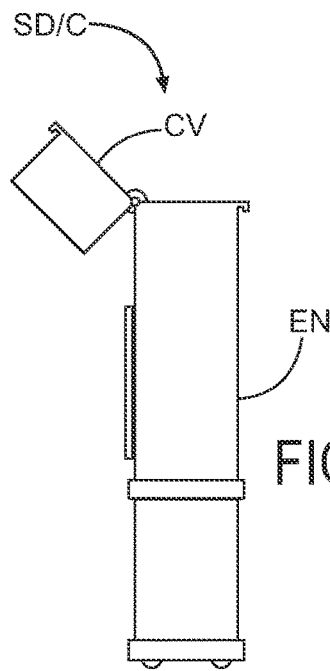
FIGS. 22A through 22C are schematic side views of a component/apparatus for dispensing scent according to an exemplary embodiment.
Figure 22B:
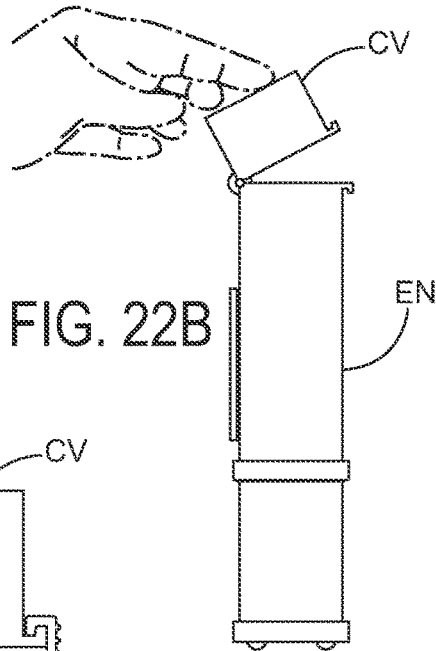
Figure 22C:
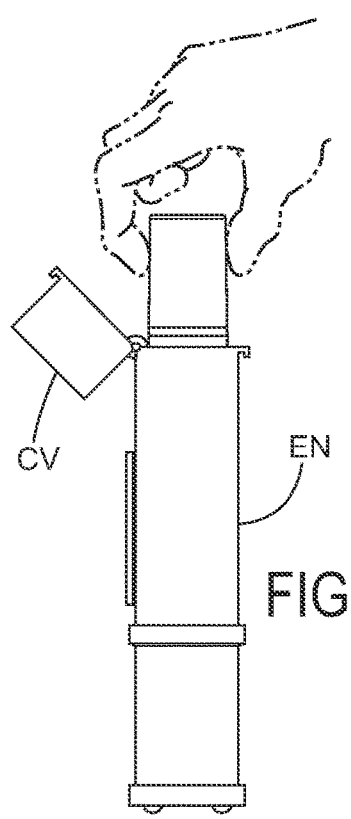
Figure 22D:
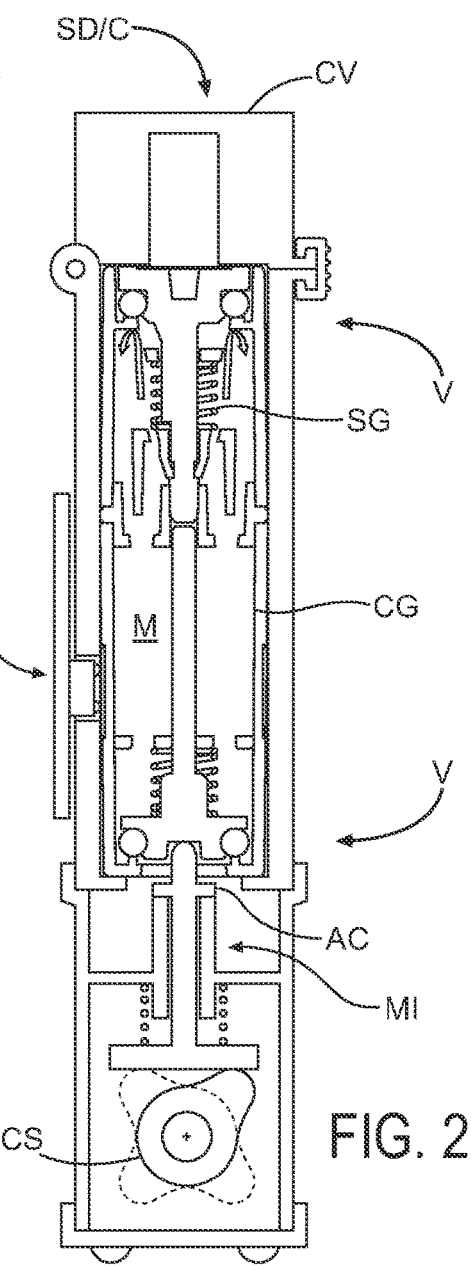
FIG. 22D is a schematic section view of a component/apparatus for dispensing scent according to an exemplary embodiment.

Component C may comprise a latch L/L1/L2/L3/L4 configured for (a) a latched state to secure the at least one cartridge arrangement CG/CG1 as shown schematically in FIG. 10B; (b) an unlatched state to present the at least one cartridge arrangement CG/CG1 for replacement as shown schematically in FIG. 10D. Component C may comprise at least one plunger P/P1/P2/P3/P4 and at least one spring SG1/SG2/SG3/SG4 configured to present the at least one cartridge arrangement CG/CG1 for replacement as shown schematically in FIG. 10D. See also FIG. 13C. Component C may comprise a catch CH as shown schematically in FIG. 12B. Latch L/L1/L2/L3/L4 may be configured to secure the at least one cartridge arrangement CG at catch CH.

Actuator/mechanism AC may comprise a motor MR and a cam shaft CS as shown schematically in FIG. 16C and may be configured for (a) a position to provide the bypass state as shown schematically in FIGS. 17A and 17C; (b) a position to provide an actuation state as shown schematically in FIGS. 17B and 17D. Actuator AC may be configured to rotate to operate a valve arrangement for a cartridge arrangement CG as shown schematically in FIGS. 17A-17D.

Cartridge CG may comprise an inlet INX and an outlet OTX. As shown schematically in FIGS. 6B and 12C, inlet INX may be positioned at a bottom surface of cartridge CG and outlet OTX may be positioned at a rear surface of cartridge CG. As shown schematically in FIGS. 8D-8E, 9C-9D, 18C-18D, 28C-28D, 34C-34D and 39A-39B, inlet INX may be positioned at a bottom surface of cartridge CG and outlet OTX may be positioned at a top surface of cartridge CG generally opposite the bottom surface of cartridge CG. As shown schematically in FIGS. 42A and 42C, inlet INX may be positioned at a bottom surface of cartridge CG and outlet OTX may be positioned at a bottom surface of cartridge CG.

Figure 24A:
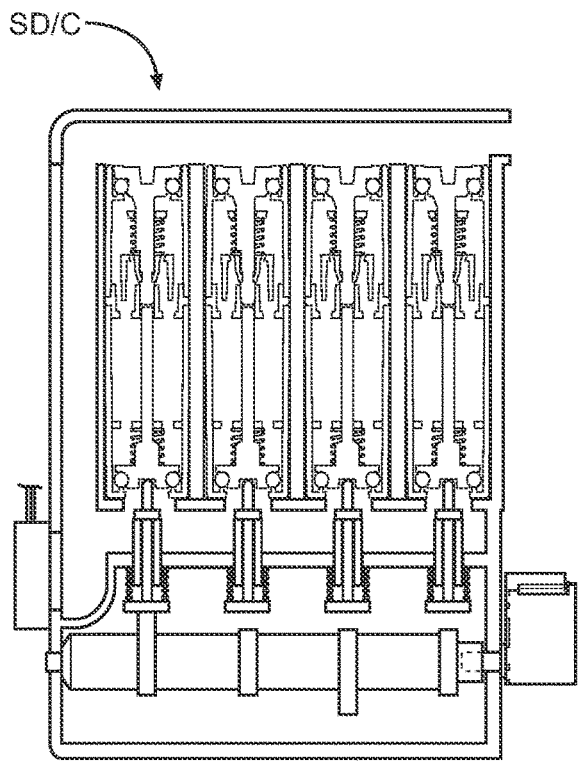
FIGS. 24A through 24C are schematic section views of a component/apparatus for dispensing scent according to an exemplary embodiment.
Figure 24B:
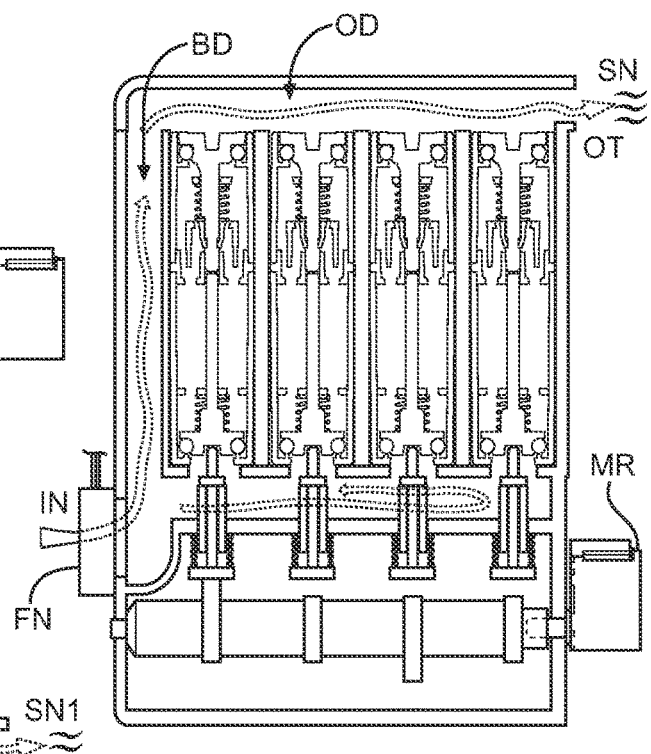
Figure 24C:
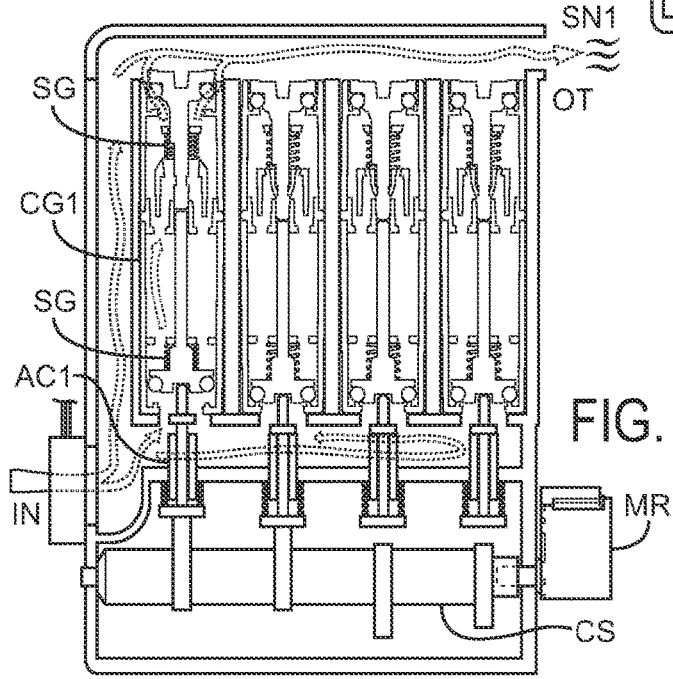
Figure 25A:
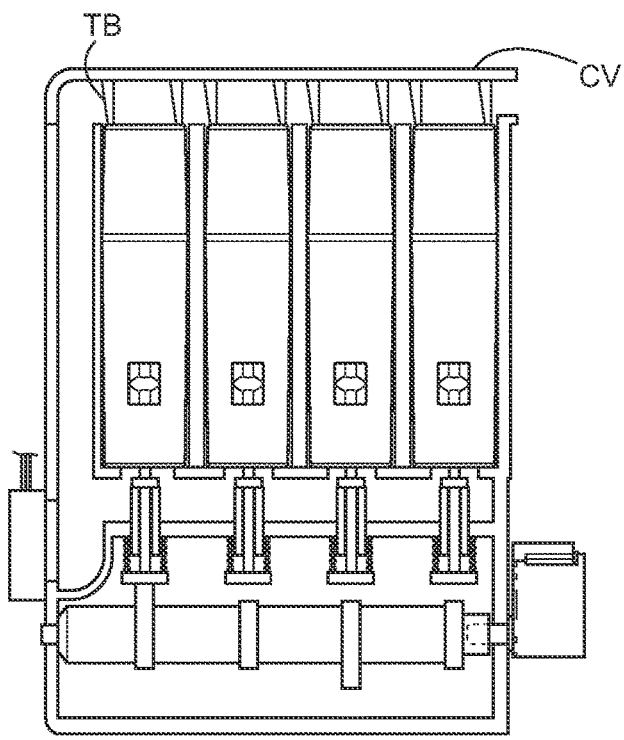
FIGS. 25A through 25C are schematic front views of a component/apparatus for dispensing scent according to an exemplary embodiment.
Figure 25B:
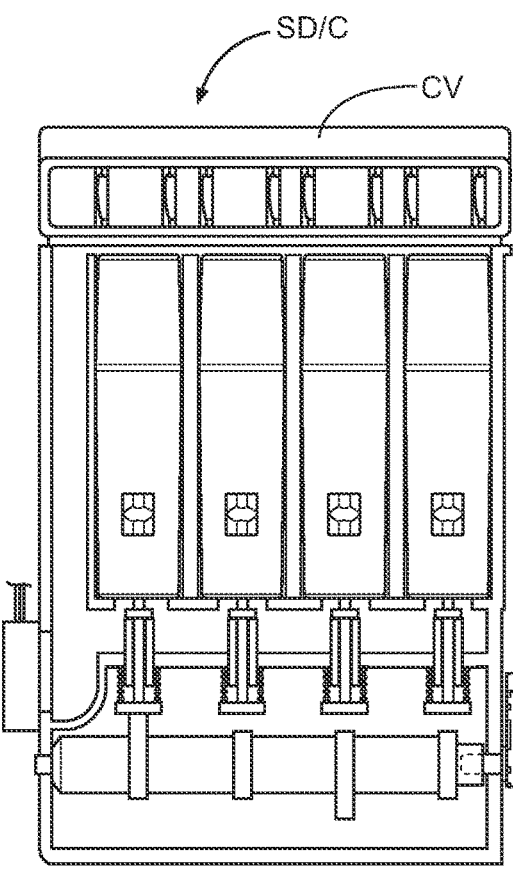
Figure 25C:
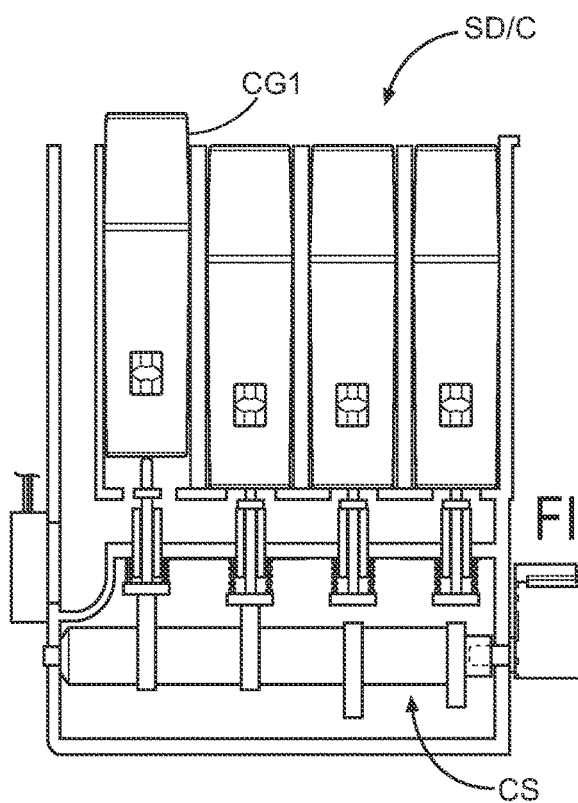
Figure 26A:
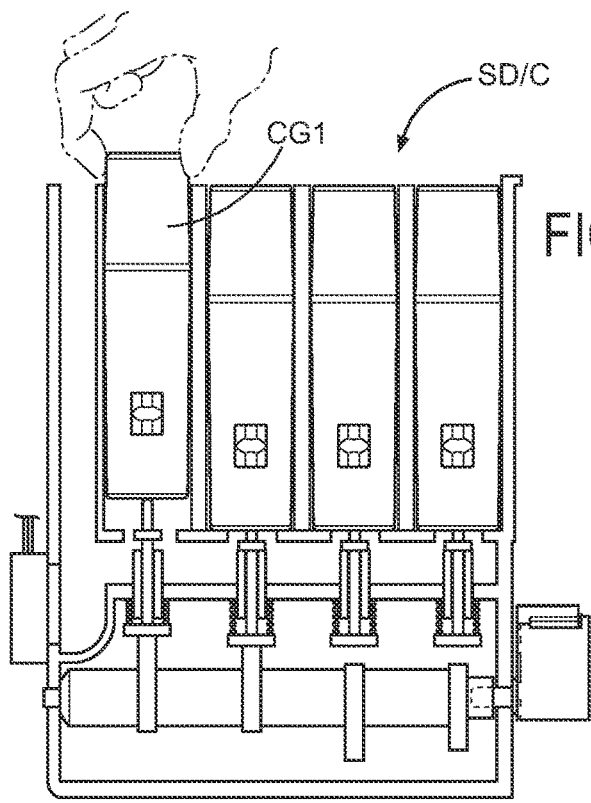
FIGS. 26A through 26C are schematic front views of a component/apparatus for dispensing scent according to an exemplary embodiment.
Figure 26B:
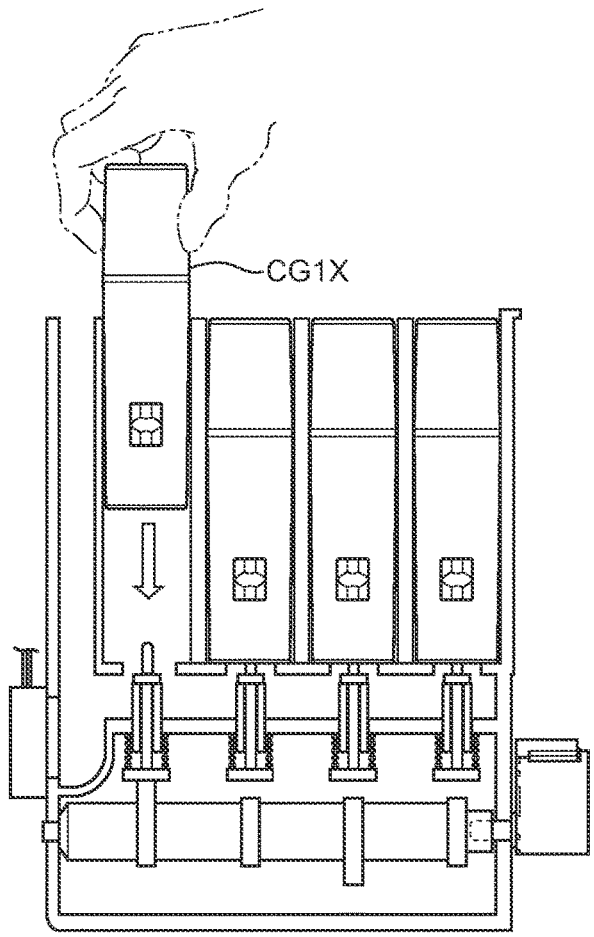
Figure 26C:
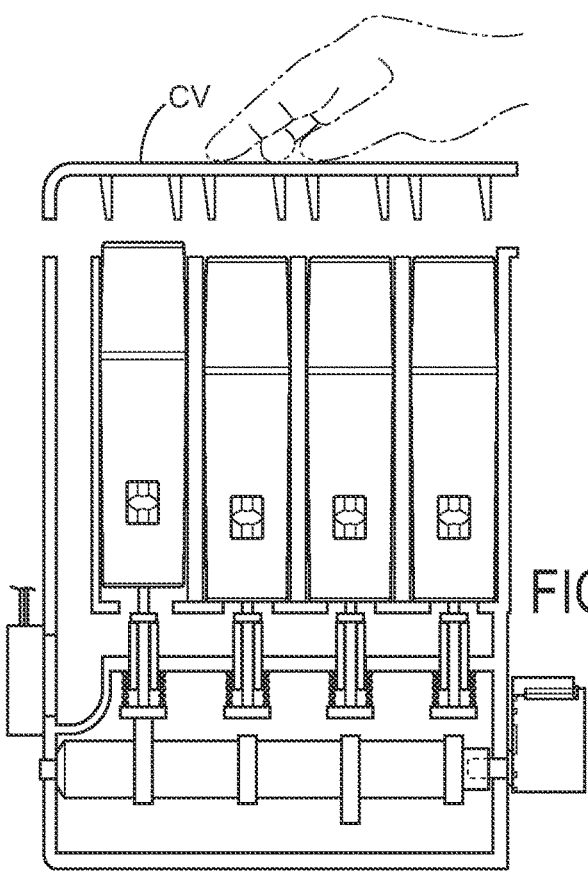

As shown schematically in FIGS. 18A, 18B, 22A-22D, 23A-23C, 24A-24C, 25A-25C and 26A-26C, a component C for a vehicle interior configured to dispense scent SN from scent media M into air in a vehicle interior may comprise an inlet IN; an outlet OT; an enclosure EN configured for at least one scent cartridge CG providing scent media M; and an actuator AC configured to actuate at least one scent cartridge CG between a sealed state and an unsealed state. The at least one scent cartridge CG may comprise a first scent cartridge CG1 and a second scent cartridge CG2. Actuator AC may be configured for (a) a bypass state with first scent cartridge CG1 in a sealed state and second scent cartridge CG2 in a sealed state as shown schematically in FIGS. 23B and 24B; (b) a first actuation state actuating first scent cartridge CG1 in an unsealed state with second scent cartridge CG2 in the sealed state as shown schematically in FIGS. 23C and 24C; (c) a second actuation state actuating second scent cartridge CG2 in an unsealed state with first scent cartridge CG1 in the sealed state. Actuator AC may comprise (a) an actuator AC1 for first scent cartridge CG1; (b) an actuator AC2 for second scent cartridge CG2. Actuator AC may comprise a cam shaft CS configured to (a) actuate first scent cartridge CG1 from the sealed state to the unsealed state to allow passage of air through scent media M of first scent cartridge CG1 toward outlet OT as shown schematically in FIGS. 23A-23C and 24A-24C; (b) actuate second scent cartridge CG2 from the sealed state to the unsealed state to allow passage of air through scent media M of second scent cartridge CG2 toward outlet OT. Cam shaft CS may be configured for (a) a position to provide the bypass state as shown schematically in FIGS. 23B and 24B; (b) a position to provide the first actuation state as shown schematically in FIGS. 23C and 24C; (c) a position to provide the second actuation state. Component C may comprise a cover CV configured for (a) a closed state to conceal the at least one scent cartridge CG as shown schematically in FIGS. 18B, 22D, 23A-23C, 24A-24C and 25A; (b) an open state to expose the at least one scent cartridge CG as shown schematically in FIGS. 18A, 22A, 22C, 25B, 25C, 26A and 26B. When cover CV is in the open state, actuator AC may be configured for at least one of (a) an inaccessible state with first scent cartridge CG1 in an inaccessible position and second scent cartridge CG2 in an inaccessible position as shown schematically in FIG. 25B; (b) a first accessible state actuating first scent cartridge CG1 in an accessible position for replacement with second scent cartridge CG2 in the inaccessible position as shown schematically in FIGS. 25C and 26A-26C; (c) a second accessible state actuating second scent cartridge CG2 in an accessible position for replacement with first scent cartridge CG1 in the inaccessible position. Component C may comprise a spring configured to move first scent cartridge CG1 and second scent cartridge CG2 to an accessible position for replacement in response to movement of cover CV from the closed state to the open state. Cover CV may be configured to compress the spring in the closed state. Component C may comprise a release mechanism configured to move the at least one scent cartridge CG to an accessible position for replacement in response to an external force applied to the at least one scent cartridge CG when cover CV is in the open state. Component C may comprise a cover CV configured for (a) a closed state to conceal the at least one scent cartridge CG; (b) an open state to expose the at least one scent cartridge CG; cover CV may comprise outlet OT. Component C may comprise an inlet duct ID and an outlet duct OD. Inlet duct ID may be separated from outlet duct OD by enclosure EN as shown schematically in FIG. 23A. Component C may comprise a cover CV for the at least one scent cartridge CG; cover CV may be configured to form outlet duct OD. Actuator AC may be positioned at an end of inlet duct ID. Component C may comprise a fan FN. Fan FN may be configured to direct air (a) to inlet duct ID; (b) through scent media M of the at least one scent cartridge CG; (c) through outlet duct OD; (d) to outlet OT. Component C may comprise a bypass duct BD. Fan FN may be configured to direct air (a) to inlet duct ID; (b) through bypass duct BD; (c) through outlet duct OD; (d) to outlet OT. Fan FN may be configured to direct air (a) to inlet duct ID; (b) through bypass duct BD and through scent media M of the at least one scent cartridge CG; (c) through outlet duct OD; (d) to outlet OT. Fan FN may be configured for at least one of (a) an off state; (b) an on state. Fan FN may be configured for (a) a high speed state; (b) a low speed state to provide (1) a high intensity scent dispersion; (2) a low intensity scent dispersion. Fan FN may be positioned at an end of inlet duct ID. Actuator AC may be configured to compress a spring SG of the at least one scent cartridge CG to actuate the at least one scent cartridge CG from the sealed state to the unsealed state to allow passage of air through the scent media M toward outlet OT as shown schematically in FIG. 24C. Component C may comprise a motor MR. Component C may comprise at least one of (a) a console; (b) an overhead console; (c) a floor console; (d) a center console.

As shown schematically in FIGS. 6B, 6C, 7B, 8D, 8E, 9C, 9D, 12B, 12C, 18C, 18D, 28C, 28D, 34C, 34D, 39A, 39B and 42A-42C the cartridge CG may be configured in a form to fit within the apparatus for use and removal/replacement (e.g. to alter/change the scent, to replace/refill, etc.) with the scent-dispensing apparatus; the cartridge CG may comprise a container for data/information shown schematically as tag TG (e.g. label, RFID tag, data tag, transmitter, etc. for tracking, matching, monitoring, authenticating, identification, serialization, communication, indication of content/media, instructions, etc.).

As shown schematically in FIGS. 8E, 9D, 12A, 18D, 19A, 19B, 28D, 28E, 34D, 39B-39D and 42D, the cartridge may comprise a chamber/body B configured to contain scent media M (e.g. material such as beads, solids, particulate matter, liquid/fluid, wick, etc. to be included at assembly/filling).

As indicated schematically in FIGS. 6A-6C, 7A-7B, 8A, 8D-8E, 9A, 9C-9D, 10A-10D, 11A-11D, 14A-14F, 15A-15F, 17A-17D, 18A-18D, 21A-21C, 23A-23C, 24A-24C, 30A-30B, 31A-31B, 32A-32B, 33A-33D, 36A-36C, 37A-37C, 41A-41D, 43A-43D and 44A-44B, the cartridge CG may be configured to contain scent media M and to provide a fit/interconnection arrangement comprising an operative interface to the scent-dispensing apparatus SD so that scent SN from the scent media M can be dispensed selectively and effectively into the interior space of the vehicle (e.g. at the direction of the vehicle occupant, vehicle control system, etc.).

As shown schematically in FIGS. 39C-39D and 42D, the cartridge/assembly CG may comprise a body B with a cap CP (shown as removable/replaceable for filling of chamber/body with scent media) and a core CR (shown as comprising a screen/divider) and a valve assembly V (shown as comprising a flow control mechanism). As indicated schematically in FIGS. 39C-39D and 40, the valve assembly may comprise flow control elements shown as valve/member and seal with a spring SG (and core/stem ST) configured to be selectively actuated to regulate/control flow of air through inlet/port INX and outlet/port OTX for the dispenser/cartridge (e.g. to provide a generally fluid-tight/leak-proof seal when closed and to provide an effective flow path for air between inlet ITX though chamber/media M within body B of cartridge CG to outlet OTX to infuse the air with scent SN when opened).

As indicated schematically in FIGS. 11A, 11C, 17A 17C, 21A, 21B, 30A, 41A, 41C, 43A, 43C and 44A when the valve assembly V/VA/VB of the cartridge/assembly CG is closed (e.g. not actuated to open) flow may be obstructed into and out of the chamber/body of the cartridge containing media M (e.g. cartridge is sealed by flow control elements). As indicated schematically in FIGS. 11B, 11D, 17B, 17D, 21C, 30B, 41B, 41D, 43B, 43D and 44B, when the valve assembly V/VA/VB of the cartridge/assembly CG is open (e.g. actuated at flow control elements to open by vehicle occupant, through user interface, by vehicle control/system, etc.) flow will pass from inlet INX though scent media M and through outlet OTX (e.g. as scented air with scent SN of scent media).

As indicated schematically in FIGS. 11B, 11D, 17B, 17D, 21C, 30B, 41D and 43D, air flow (e.g. air supply into the apparatus SD passively and/or actively such as by fan, vacuum/pressure, etc.) provided to an inlet/port INX through the scent media M and from outlet/port OTX will be infused with a scent SN (e.g. dispensed to include a scent SN in a concentration intended to be perceptible within the air/ambient environment to occupants of the vehicle). See also FIG. 1C.

As shown schematically in FIGS. 8A-8E, 28A-28E, 29A-29C, 30A-30B, 31A-31B, 32A-32B and 33A-33D, a component C for a vehicle interior configured to dispense scent SN from scent media M into air in a vehicle interior may comprise an inlet IN; an outlet OT; an enclosure EN configured for at least one scent-containing cartridge arrangement CG providing scent media M (e.g. media contained within the body of the cartridge); and an actuator AC configured to actuate at least one scent-containing cartridge arrangement CG between a sealed state and an unsealed state (e.g. through a valve arrangement VA/VB configured to open and close). The at least one scent-containing cartridge arrangement CG may comprise a first scent-containing cartridge arrangement CG1 and a second scent-containing cartridge arrangement CG2. The at least one scent-containing cartridge arrangement CG may comprise a third scent-containing cartridge arrangement CG3.

Figure 31A:
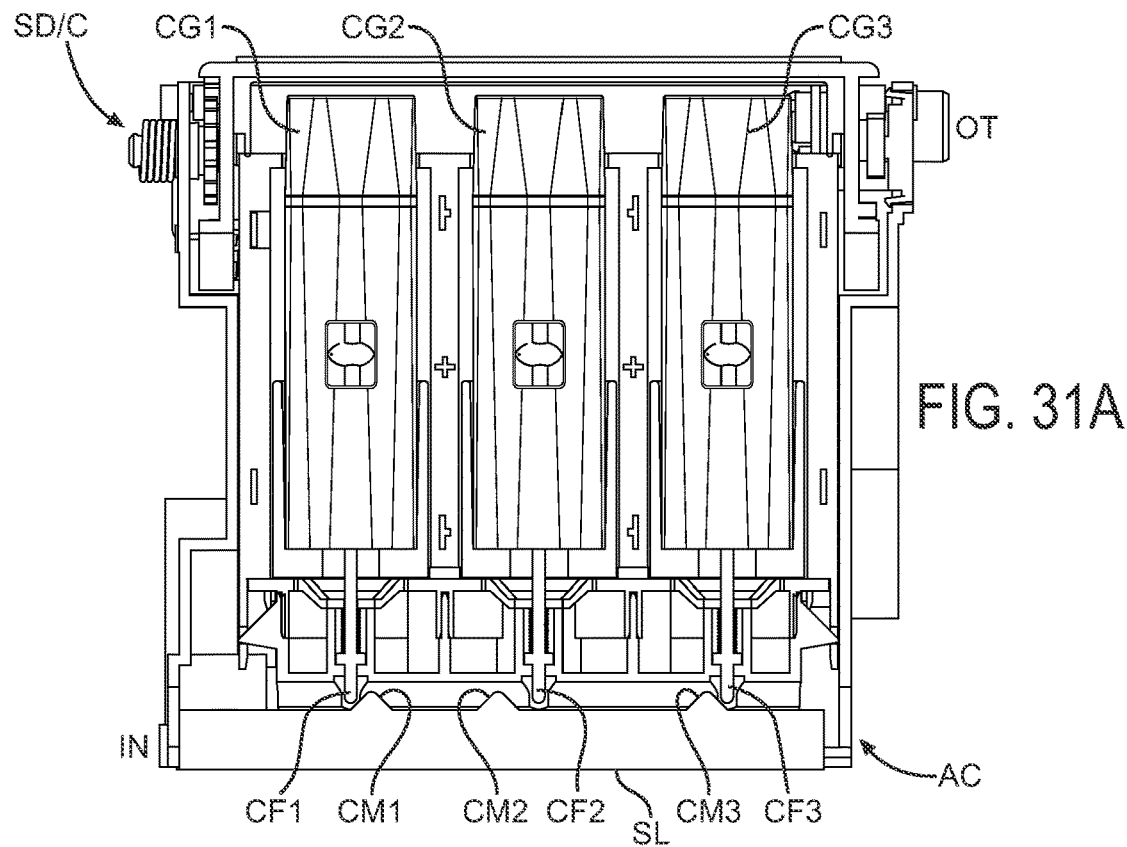
FIGS. 31A and 31B are schematic front views of a component/apparatus for dispensing scent according to an exemplary embodiment.
Figure 31B:
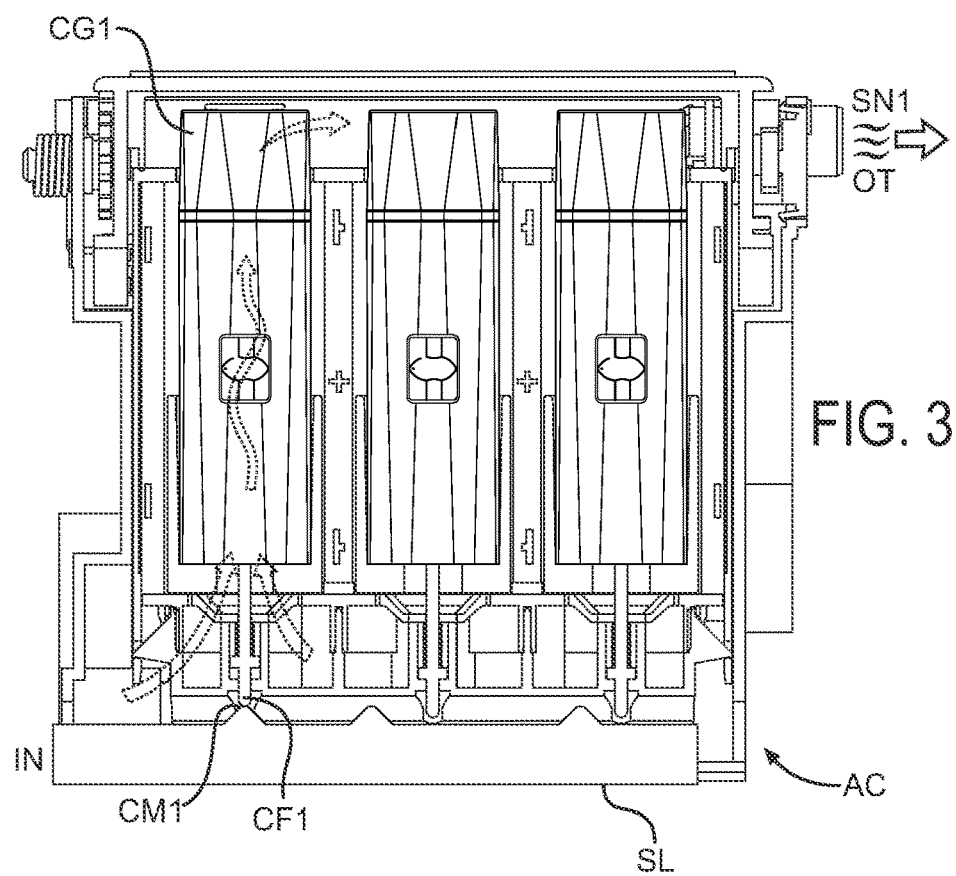
Figure 32A:
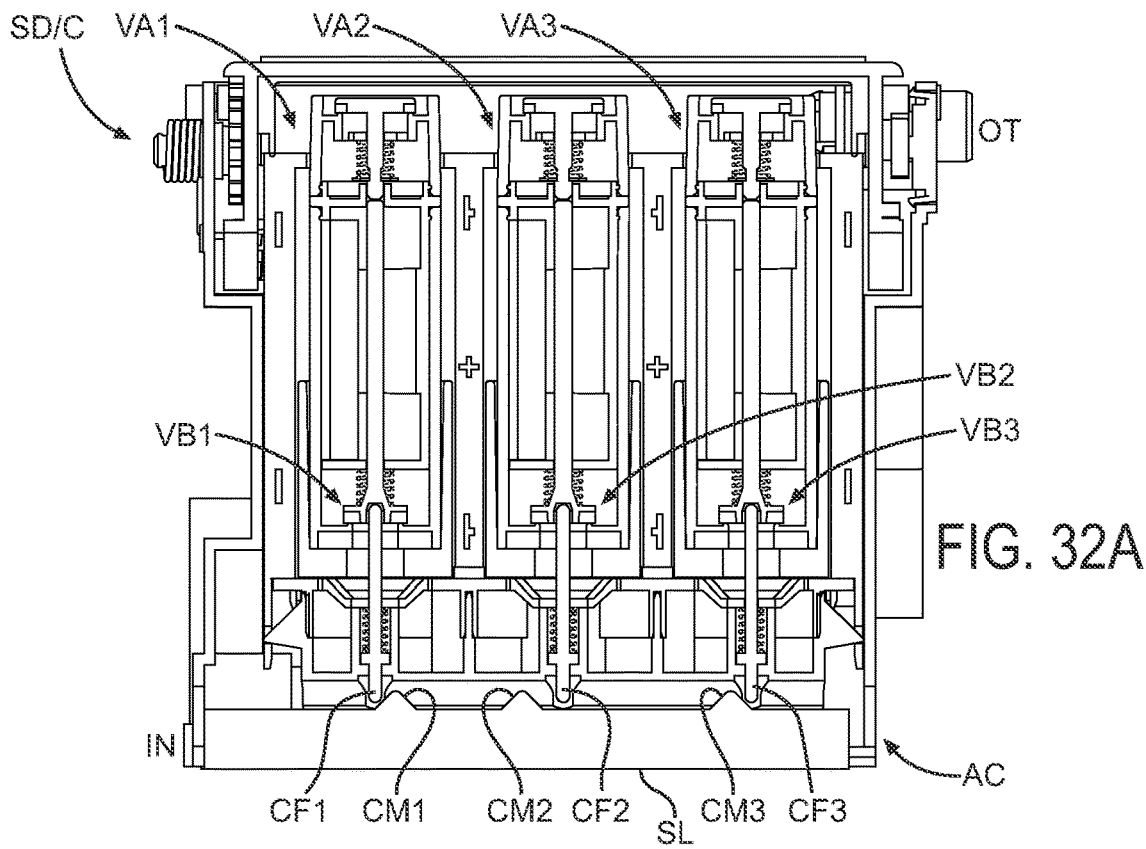
FIGS. 32A and 32B are schematic section views of a component/apparatus for dispensing scent according to an exemplary embodiment.
Figure 32B:
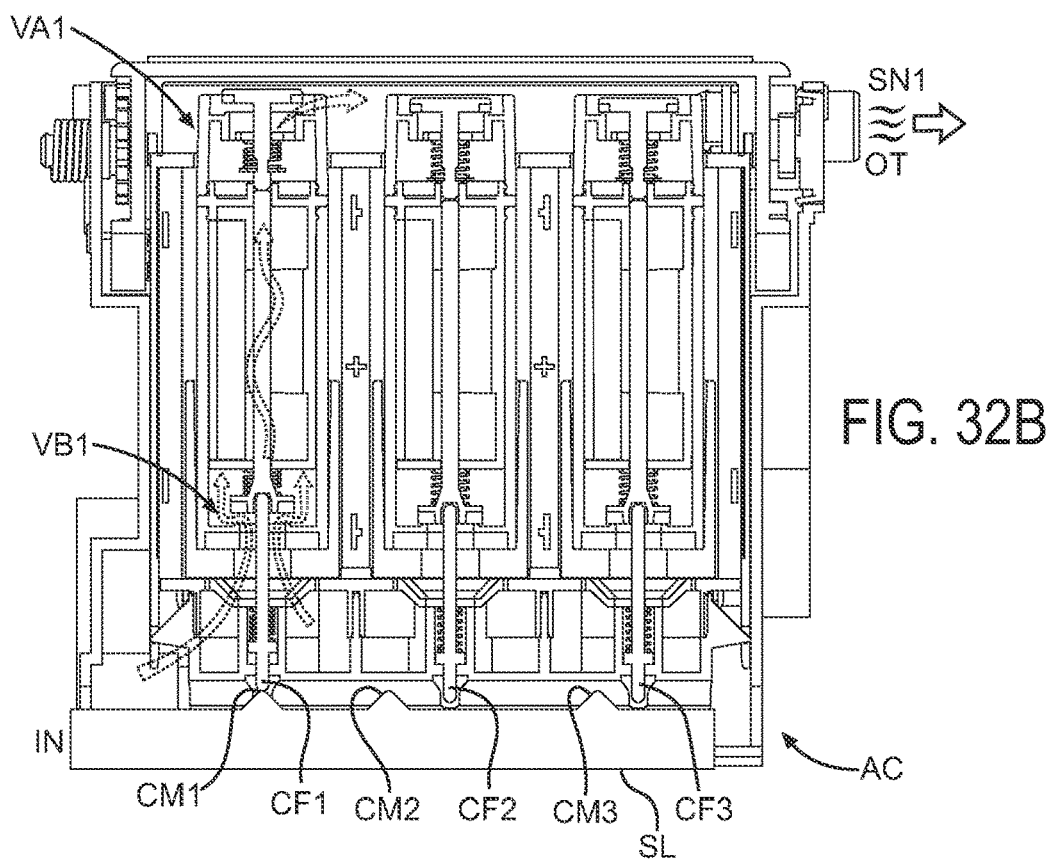
Figure 33A:
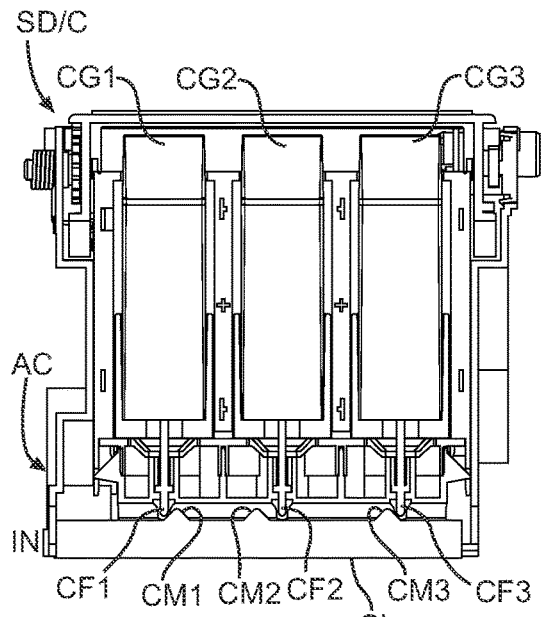
FIGS. 33A through 33D are schematic front views of a component/apparatus for dispensing scent according to an exemplary embodiment.
Figure 33B:
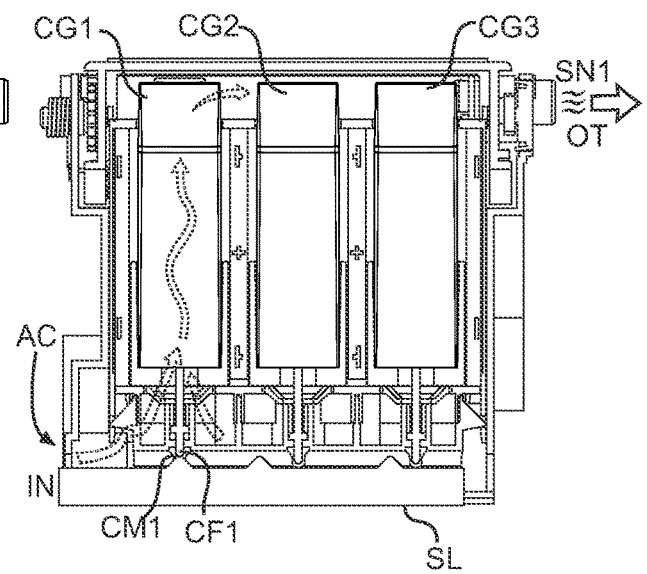
Figure 33C:
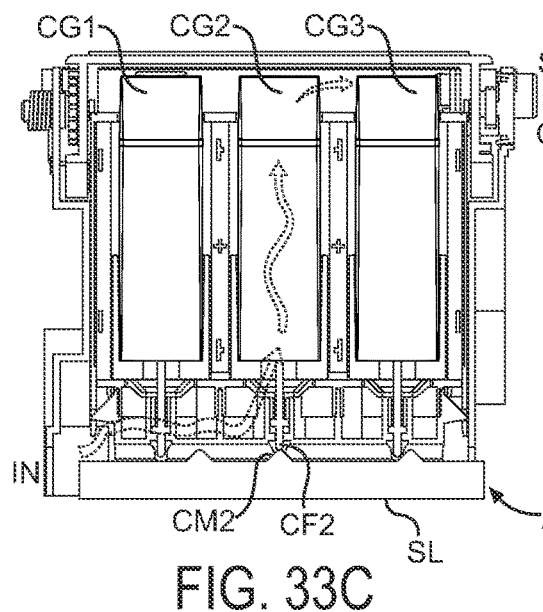

Actuator AC may be configured for (a) a bypass state with first scent-containing cartridge arrangement CG1 in a sealed state and second scent-containing cartridge arrangement CG2 in a sealed state and third scent-containing cartridge arrangement CG3 in a sealed state as shown schematically in FIGS. 31A, 32A and 33A; (b) a first actuation state actuating first scent-containing cartridge arrangement CG1 in an unsealed state with second scent-containing cartridge arrangement CG2 in the sealed state and third scent-containing cartridge arrangement CG3 in a sealed state as shown schematically in FIGS. 31B, 32B and 33B; (c) a second actuation state actuating second scent-containing cartridge arrangement CG2 in an unsealed state with first scent-containing cartridge arrangement CG1 and third scent-containing cartridge arrangement CG3 in the sealed state as shown schematically in FIG. 33C; (d) a third actuation state actuating third scent-containing cartridge arrangement CG3 in an unsealed state with first scent-containing cartridge arrangement CG1 and second scent-containing cartridge arrangement CG2 in the sealed state as shown schematically in FIG. 33D.

Actuator/mechanism AC may comprise a motor MR and slider arrangement SL and may be configured for (a) a position to provide the bypass state as shown schematically in FIGS. 31A and 32A; (b) a position to provide the first actuation state as shown schematically in FIGS. 31B and 32B; (c) a position to provide the second actuation state; (c) a position to provide the third actuation state. See also FIGS. 33A-33D. Actuator AC may comprise (a) a cam/follower arrangement CM1/CF1 to operate a valve arrangement VA1/VB1 for first cartridge arrangement CG1; (b) a cam/follower arrangement CM2/CF2 to operate a valve arrangement VA2/VB2 for second cartridge arrangement CG2; (c) a cam/follower arrangement CM3/CF3 to operate a valve arrangement VA3/VB3 for third cartridge arrangement CG3. Actuator AC may comprise a shaft configured to (a) actuate first cartridge arrangement CG1 from the sealed state to the unsealed state to allow passage of air through scent media M of first cartridge arrangement CG1 toward outlet OT as shown schematically in FIGS. 31A-31B and 32A-32B; (b) actuate second cartridge arrangement CG2 from the sealed state to the unsealed state to allow passage of air through scent media M of second cartridge arrangement CG2 toward outlet OT.

Component C may comprise a cover CV configured for (a) a closed state to conceal the at least one cartridge arrangement CG as shown schematically in FIGS. 8B, 28B, 30A, 30B, 31A, 31B, 32A, 32B and 33A-33D; (b) an open state to expose the at least one cartridge arrangement CG as shown schematically in FIGS. 8A, 28A, 29A and 29B. When cover CV is in the open state, first cartridge arrangement CG1, second cartridge arrangement CG2 and third cartridge arrangement CG3 may be accessible for replacement. Component C may comprise a cover CV configured for (a) a closed state to conceal the at least one cartridge arrangement CG as shown schematically in FIGS. 28B, 30A, 30B, 31A, 31B, 32A, 32B and 33A-33D; (b) an open state to expose the at least one cartridge arrangement CG as shown schematically in FIGS. 28A, 29A and 29B.

Component C may comprise an inlet duct ID and an outlet duct OD. Inlet duct ID may be separated from outlet duct OD by enclosure EN as shown schematically in FIG. 31A. Component C may comprise a cover CV for the at least one cartridge arrangement CG. Actuator AC may be positioned at an end of inlet duct ID. Component C may comprise a fan FN as shown schematically in FIG. 8C. Fan FN may be configured to direct air (a) to inlet duct ID; (b) through scent media M of the at least one cartridge arrangement CG; (c) through outlet duct OD; (d) to outlet OT. Fan FN may be configured to direct air (a) to inlet duct ID; (b) through scent media M of the at least one cartridge arrangement CG; (c) through outlet duct OD; (d) to outlet OT. Fan FN may be configured for at least one of (a) an off state; (b) an on state. Fan FN may be configured for (a) a high speed state; (b) a low speed state to provide (1) a high intensity scent dispersion; (2) a low intensity scent dispersion. Fan FN may be positioned at an end of inlet duct ID. Actuator AC may be configured to compress a spring SG of the at least one cartridge arrangement CG to actuate the at least one cartridge arrangement CG from the sealed state to the unsealed state to allow passage of air through the scent media M toward outlet OT as shown schematically in FIGS. 31B and 32B. Component C may comprise a motor MR as shown schematically in FIG. 31A.

Component C for the scent dispensing apparatus SD may comprise at least one of (a) a console; (b) an overhead console; (c) a floor console; (d) a center console.

Figure 34A:
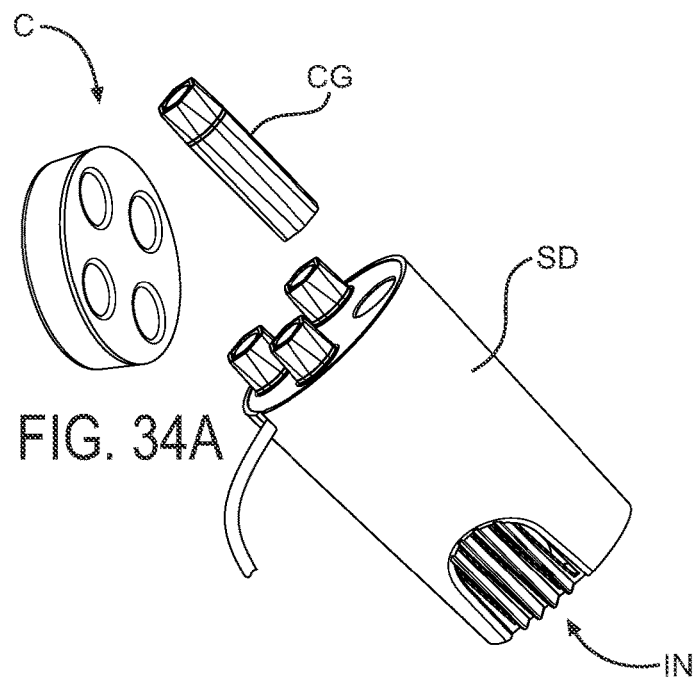
FIGS. 34A and 34B are schematic perspective views of a component/apparatus for dispensing scent according to an exemplary embodiment.
Figure 34B:
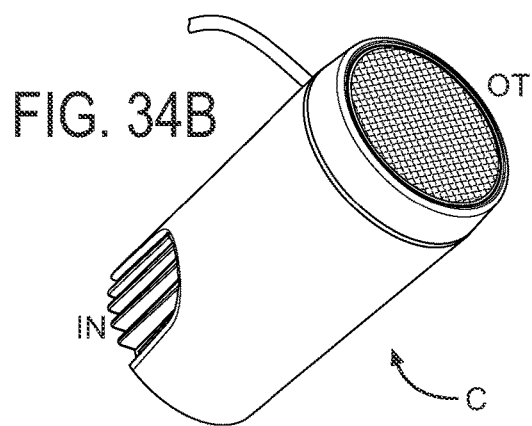
Figure 34C:
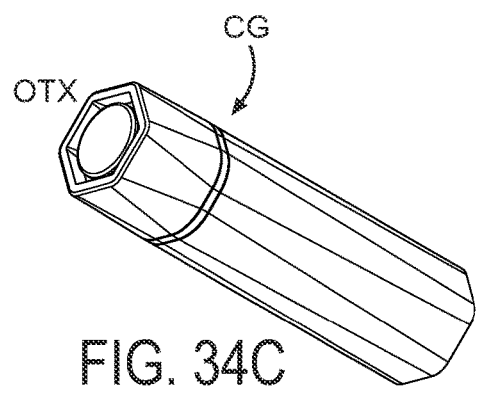
FIGS. 34C and 34D are schematic perspective views of an apparatus/system for dispensing scent with a cartridge according to an exemplary embodiment.
Figure 34D:
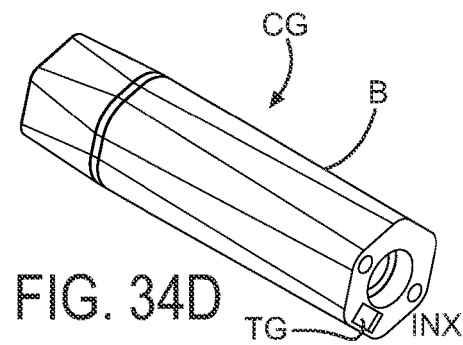
Figure 35:
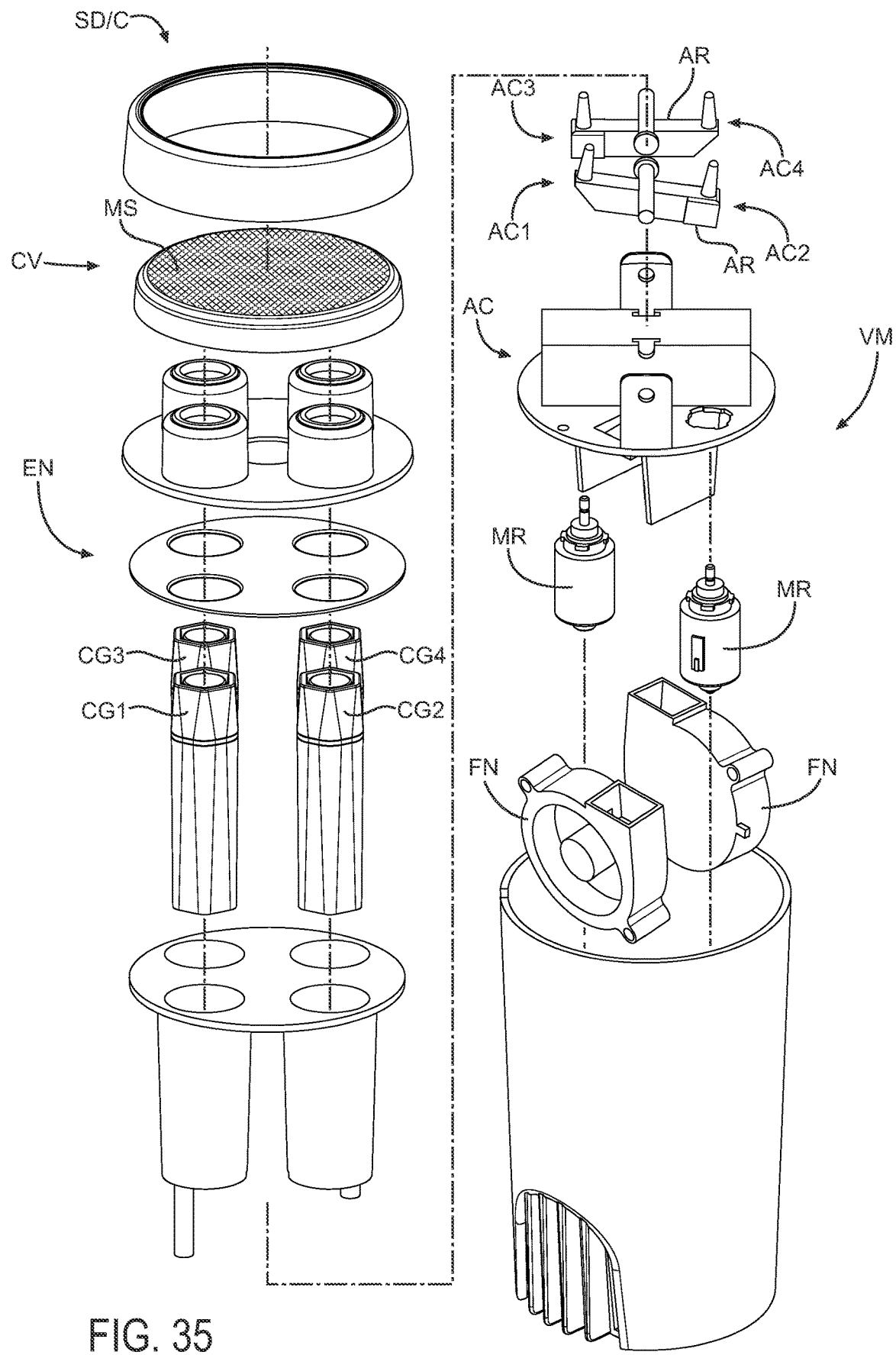
FIG. 35 is a schematic exploded perspective view of a component/apparatus for dispensing scent according to an exemplary embodiment.

As shown schematically in FIGS. 9A-9D, 34A-34D, 35, 36A-36C and 37A-37C, a component C for a vehicle interior configured to dispense scent from scent media into air in a vehicle interior may comprise: an inlet IN; an outlet OT; an enclosure EN configured for at least one scent cartridge CG/CG1/CG2/CG3/CG4 providing scent media; and an actuator AC/AC1/AC2/AC3/AC4 configured to actuate at least one scent cartridge between a sealed state (as shown schematically in FIGS. 36A and 37A) and an unsealed state (as shown schematically in FIGS. 36B, 36C, 37B and 37C). The at least one scent cartridge may comprise a first scent cartridge CG1 and a second scent cartridge CG2. The actuator may comprise (a) an actuator AC1 for the first scent cartridge; (b) an actuator AC2 for the second scent cartridge. The actuator may be configured to (a) rotate in a first direction to actuate the first scent cartridge (as shown schematically in FIGS. 36C and 37C) and (b) rotate in a second direction generally opposite the first direction to actuate the second scent cartridge (as shown schematically in FIGS. 36B and 37B). The actuator may be configured for (a) a default state with the first scent cartridge in a sealed state and the second scent cartridge in a sealed state (as shown schematically in FIGS. 36A and 37A); (b) a first actuation state actuating the first scent cartridge in an unsealed state with the second scent cartridge in the sealed state (as shown schematically in FIGS. 36C and 37C); (c) a second actuation state actuating the second scent cartridge in an unsealed state with the first scent cartridge in the sealed state (as shown schematically in FIGS. 36B and 37B). The actuator may comprise a shaft S configured to (a) actuate the first scent cartridge from the sealed state to the unsealed state to allow passage of air through scent media of the first scent cartridge toward the outlet (as shown schematically in FIGS. 36C and 37C); (b) actuate the second scent cartridge from the sealed state to the unsealed state to allow passage of air through scent media of the second scent cartridge toward the outlet (as shown schematically in FIGS. 36B and 37B). The shaft may be configured for (a) a first position to provide the first actuation state (as shown schematically in FIGS. 36C and 37C); (b) a second position to provide the second actuation state (as shown schematically in FIGS. 36B and 37B); (c) a third position to provide the default state (as shown schematically in FIGS. 36A and 37A). The first position may comprise an extended position; the second position may comprise a retracted position; the third position may comprise a middle position. The component may comprise a motor MR configured to move the shaft between the first position; the second position; the third position. The shaft may be configured to translate to actuate an actuator to rotate to actuate the first scent cartridge. The actuator may comprise a seesaw mechanism. The seesaw mechanism may comprise an arm AR comprising (a) an actuator AC1 for the first scent cartridge; (b) an actuator AC2 for the second scent cartridge. The seesaw mechanism may comprise a motor MR and a shaft S; the motor may be configured to move the shaft at an end of the arm to rotate the arm. The actuator may comprise an arm AR configured to rotate to actuate the at least one scent cartridge. The at least one scent cartridge may comprise a first scent cartridge and a second scent cartridge; the actuator may comprise a motor configured to pull the arm toward the motor to actuate the first scent cartridge; the motor may be configured to push the arm to actuate the second scent cartridge. The component may comprise a cover CV configured for (a) a closed state to conceal the at least one scent cartridge (as shown schematically in FIGS. 34B, 36A-36C and 37A-37C); (b) an open state to expose the at least one scent cartridge (as shown schematically in FIG. 34A). The cover may comprise a mesh MS configured to conceal the at least one scent cartridge and allow air to pass through the outlet. The cover may comprise the outlet. The cover may comprise a magnet configured to couple the cover and the enclosure. The component may comprise an inlet chamber IC. The inlet chamber may be separated from the outlet by the enclosure. The component may comprise a cover for the at least one scent cartridge; the cover may be configured to form the outlet. The actuator may be positioned at an end of the inlet chamber. The component may comprise a fan F. The fan may be configured to direct air (a) to the inlet chamber; (b) through scent media of the at least one scent cartridge; (c) through the outlet. The fan may be configured for at least one of (a) an off state; (b) an on state. The fan may be configured for (a) a high speed state; (b) a low speed state to provide (1) a high intensity scent dispersion; (2) a low intensity scent dispersion. The fan may be positioned at an end of the inlet chamber. The fan may comprise a first fan and a second fan. The fan may be configured for (1) a high intensity scent dispersion with the first fan on and the second fan on; (2) a low intensity scent dispersion with the first fan on and the second fan off. The at least one scent cartridge may comprise a first scent cartridge CG1, a second scent cartridge CG2, a third scent cartridge CG3 and a fourth scent cartridge CG4; the first fan may be configured to direct air through scent media of the first scent cartridge and through scent media of the second scent cartridge; the second fan may be configured to direct air through scent media of the third scent cartridge and through scent media of the fourth scent cartridge. The actuator may be configured to compress a spring SG of the at least one scent cartridge to actuate the at least one scent cartridge from the sealed state to the unsealed state to allow passage of air through the scent media toward the outlet (as shown schematically in FIGS. 37B and 37C). The component may comprise at least one of: (a) a console; (b) an overhead console; (c) a floor console; (d) a center console; (e) a cup holder; (f) a module configured to mount within a cupholder.

As shown schematically in FIGS. 34A-34D, 35, 36A-36C and 37A-37C, a system for a vehicle interior configured to dispense scent from scent media contained in at least one cartridge into air in a vehicle interior may comprise: an inlet; an outlet; an enclosure configured for at least one cartridge providing scent media; an actuator configured to actuate at least one cartridge between a sealed state and an unsealed state; and a user interface. The user interface may be configured to facilitate the selection of scent by selection of at least one cartridge for actuation. The user interface may be configured for selection of intensity of scent from at least one cartridge.

As shown schematically in FIGS. 34A-34D, 35, 36A-36C and 37A-37C, a vehicle interior configured to dispense scent from scent media contained in at least one cartridge into air in a vehicle interior may comprise: an inlet; an outlet; a chamber configured for at least one scent cartridge providing scent media; and an actuator configured to actuate at least one cartridge between a sealed state and an unsealed state. The scent may be dispensed from the outlet by selection of the at least one cartridge.

As shown schematically in FIGS. 34A-34D, 35, 36A-36C and 37A-37C, a module for a vehicle interior configured to dispense scent from scent media contained in at least one interchangeable cartridge into air in a vehicle interior comprising: an enclosure configured for at least one interchangeable scent-dispensing cartridge comprising scent media; an actuator configured to actuate at least one cartridge to dispense scent; and an interface between the at least one cartridge and the enclosure. The chamber may be configured so that at least one cartridge can be removed and replaced with at least one cartridge. The interface may comprise at least one of a data/network interface and a mechanical interface.

As shown schematically in FIGS. 34A-34D, 35, 36A-36C and 37A-37C, a system for a vehicle interior configured to dispense scent from scent media contained in at least one cartridge into air in a vehicle interior may comprise: an inlet IN; an outlet OT; an enclosure EN configured for at least one cartridge providing scent media; a valve mechanism VM configured to actuate at least one cartridge CG/CG1/CG2/CG3/CG4 between a sealed state and an unsealed state; and a user interface. The user interface may be configured to facilitate the selection of scent by selection of at least one cartridge for actuation.

As shown schematically in FIGS. 34A-34D, 35, 36A-36C and 37A-37C, an apparatus for a vehicle interior configured to dispense scent from scent media contained in at least one cartridge into air in a vehicle interior may comprise: an inlet IN; an outlet OT; a chamber configured for at least one scent cartridge CG/CG1/CG2/CG3/CG4 providing scent media; and a valve mechanism VM configured to actuate at least one cartridge between a sealed state and an unsealed state. The scent may be dispensed from the outlet by selection of the at least one cartridge.

As shown schematically in FIGS. 34A-34D, 35, 36A-36C and 37A-37C, a module for a vehicle interior configured to dispense scent from scent media contained in at least one interchangeable cartridge into air in a vehicle interior may comprise: an enclosure EN configured for at least one interchangeable scent-dispensing cartridge comprising scent media; a valve mechanism VM configured to actuate at least one cartridge CG/CG1/CG2/CG3/CG4 to dispense scent; and an interface between the at least one cartridge and the enclosure. The chamber may be configured so that at least one cartridge can be removed and replaced with at least one cartridge; the interface may comprise at least one of a data/network interface and a mechanical interface. The valve mechanism may comprise an actuator. The valve mechanism may be configured to be operated by a power supply. The interface may comprise a user interface for a vehicle component. The valve mechanism may be configured to be operated by the user interface. The valve mechanism may comprise a valve arrangement.

Exemplary Embodiments—System Function/Operation

Referring to FIGS. 2, 18A-18B and 27A-27B, the system and method of operation of the module/component for dispensing scent SD/C is shown schematically according to an exemplary embodiment. See also FIGS. 45A-45D and 46.

As shown schematically in FIGS. 18A-18B and 27A-27B, the system SD may comprise the module with cartridges and an interface (e.g. mechanical, data/electronic, instrumentation, network, etc.) as well as a user interface (e.g. control, touch screen, buttons, etc.) which can be provided on and/or adjacent to the module (e.g. in the vehicle accessible to an occupant through a dedicated and/or existing user interface system that may connect to other vehicle systems).

The module may provide a data interface that comprises interaction/connection with a data/information tag on the cartridge (e.g. to register, store, monitor, interact, etc.) and a mechanical interface that comprises a fit/connection (e.g. proprietary connection design, etc.); as indicated, cartridges are inserted/installed into the module may be seated/retained by tabs TB upon closure of the cover CV and/or retained by a mechanism (e.g. push-push latch, pop-out spring, etc.). See FIGS. 18A-18B and 25A.

As indicated schematically, in operation the system SD may provide an output OT/SN of scented air from an input supply IN of air from the vehicle and/or the vehicle ventilation system (or heating, ventilation, air conditioning system, etc.). According to an exemplary embodiment shown schematically in FIGS. 18A-18B 23C and 24C, the module/system may comprise a fan configured to operate at a fixed speed or to operate by modulation (e.g. pulsing, pulse-width modulation (PWM), dual speed, variable speed, etc.) to draw input air IN that will flow through the module; if a selected scent cartridge is open (e.g. actuated at the user interface and through motor MR) input air in some proportion will flow into the scent cartridge and mix into scented output air OT/SN with a fragrance from the selected scent cartridge. See generally FIGS. 23A-23C and 24A-24C (indicating operation of one selected cartridge of four potentially selectable cartridges). As indicated schematically in FIGS. 27A and 27B, the system may be configured to facilitate selection of a scent cartridge by an occupant of the vehicle using the user interface (e.g. by a control/connection that is mechanical, electronic, data, network, remote, etc.).

Figure 27A:
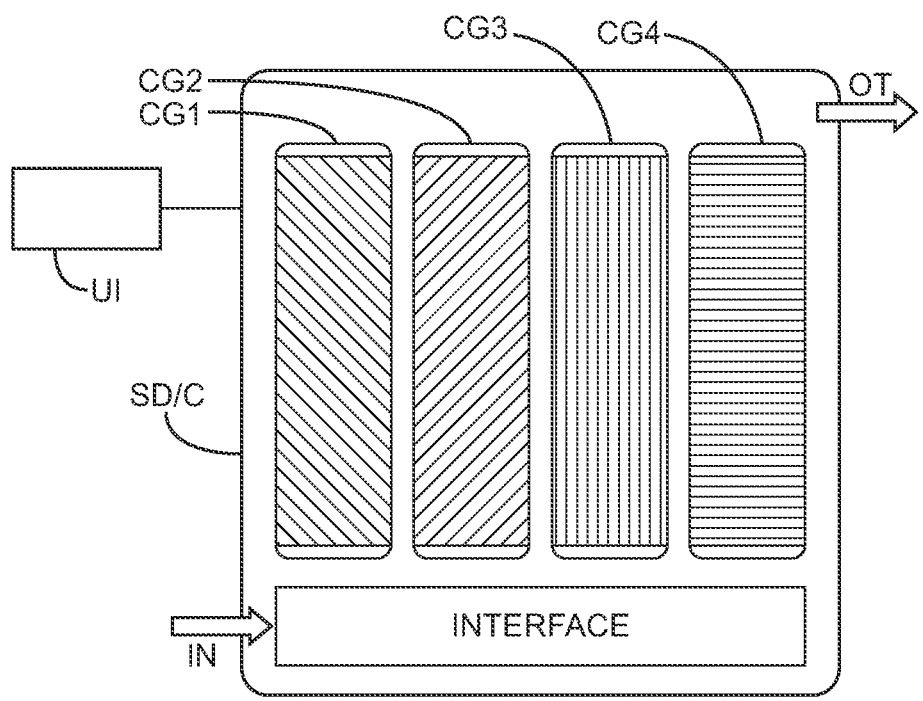
FIGS. 27A and 27B are schematic system diagrams according to an exemplary embodiment.
Figure 27B:
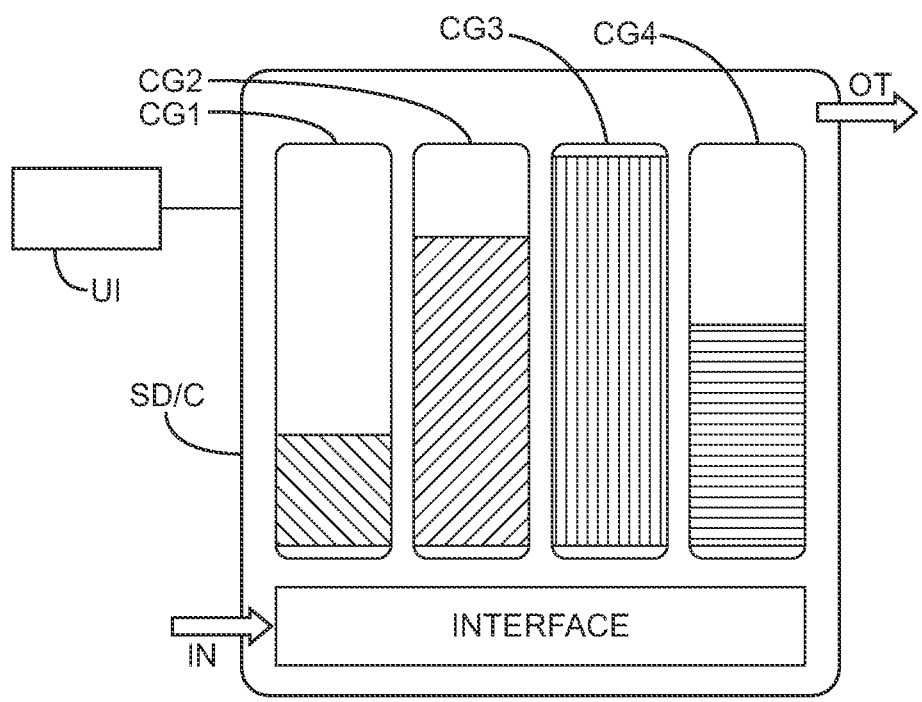
Figures 29A, 29B, 29C:
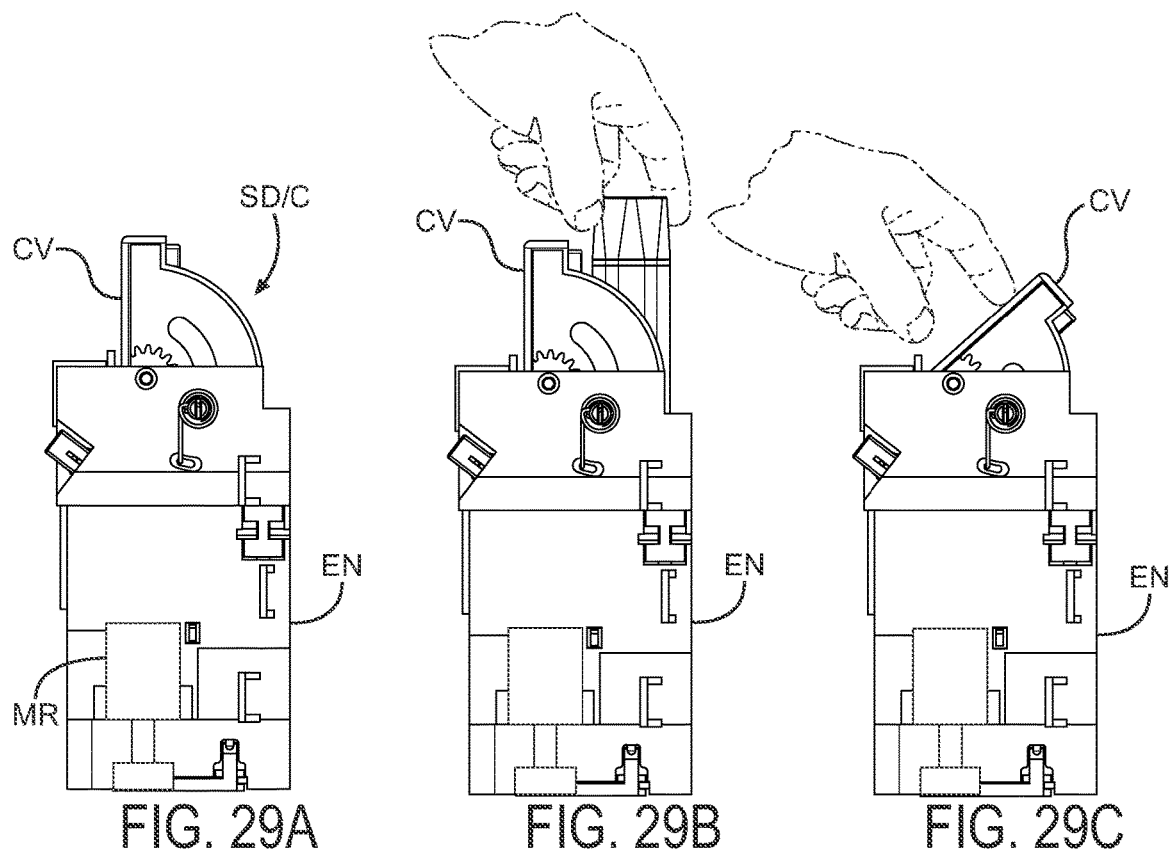
FIGS. 29A through 29C are schematic side views of a component/apparatus for dispensing scent according to an exemplary embodiment.
Figures 30A, 30B:
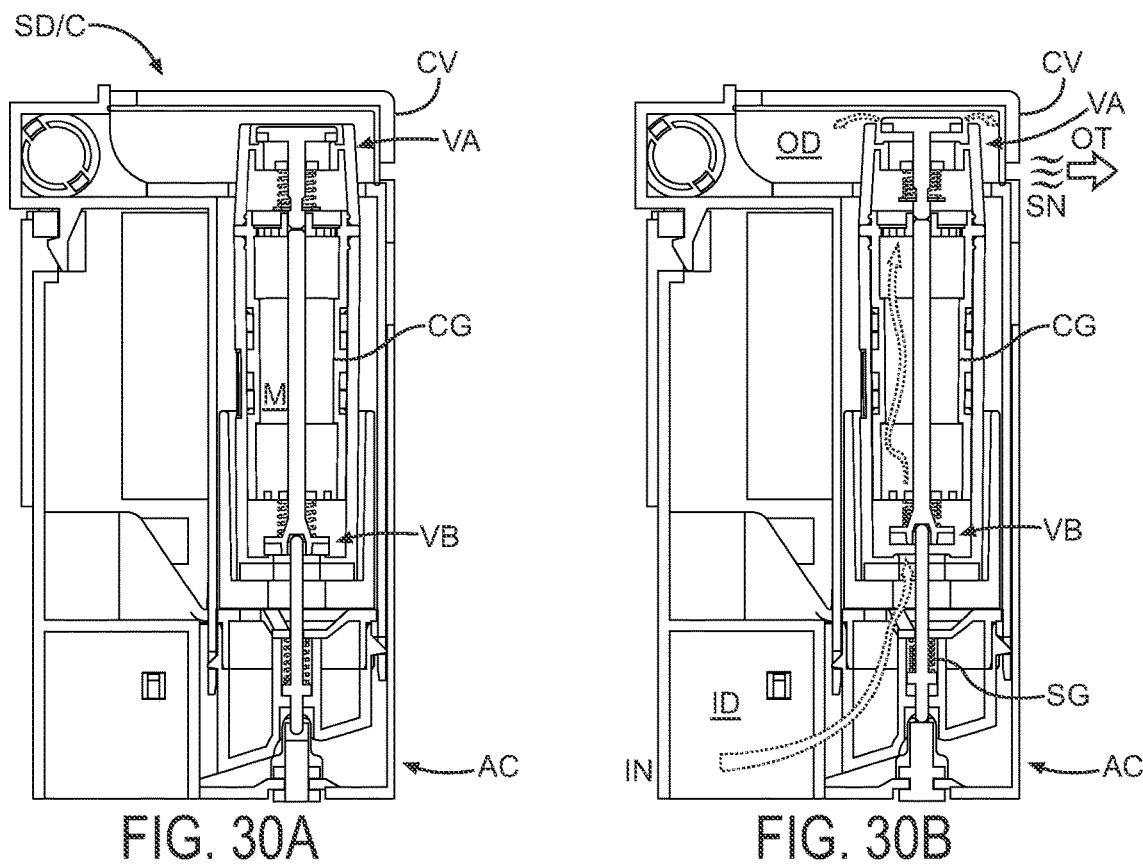
FIGS. 30A and 30B are schematic section views of a component/apparatus for dispensing scent according to an exemplary embodiment.

As indicated schematically according to an exemplary embodiment in FIGS. 23A and 27A-27B, the system may be configured to use data/information (e.g. from monitoring, instrumentation, interconnectivity, etc.) for use/operation of the module and/or for presentation at the user interface; for example, as indicated in FIGS. 27A and 27B, the level of efficacy/scent in a cartridge (or set of cartridges) may be monitored (e.g. by instrumentation, measurement, computation, proxy, etc.) to indicate when a replacement of a cartridge is needed (e.g. indicating that one or more cartridges are expended and/or nearly expended and to what degree).

As indicated schematically in FIGS. 27A-27B, the system may function according to a control program to facilitate operation and data display/interchange (e.g. indicated through or at the user interface and/or by the module) to present scent for the vehicle interior. The module may be activated and indicate presence/absence and/or type/compatibility of a cartridge (e.g. by detection of the tag/information at the data interface) and the state of operation of the system (e.g. by data flow/connectivity, detection, monitoring, etc.) such as whether any cartridge is depleted and/or in need of replacement (or not operational/functioning) and then may provide information/instructions to the occupant/user to take action such as replacement. As indicated schematically, operation of the system may be controlled at a user interface (e.g. access to control/information as to settings, options for operation, operating conditions, ambient conditions, etc.); for example, the module may be operated in a bypass mode (no scent) and/or with selection of one of the available/installed scent cartridges and setting of intensity of scent to be provided within an available range (e.g. by operation of the fan and/or flow control element of a cartridge, etc.); a different cartridge may be selected for diffusion of scent into the vehicle interior; the module may be turned off (e.g. operation ended). As indicated schematically, the cartridge replacement process may be guided by instructions presented at a user interface (e.g. removal/replacement of cartridges, bypass mode, etc.).

According to an exemplary embodiment, modes of system function/operation are indicated in TABLE 1.

TABLE 1

MODES OF SYSTEM FUNCTION/OPERATION

| Mode | Cover | Cartridges | Actuator | Fan |
|---|---|---|---|---|
| Install B | Open | All Sealed All Inaccessible | Bypass | Off |
| Install 1 | Open | All Sealed CG1 Accessible | Present CG1 | Off |
| Install 2 | Open | All Sealed CG2 Accessible | Present CG2 | Off |
| Bypass, Fan Off | Closed | All Sealed | Bypass | Off |
| Bypass, Fan On | Closed | All Sealed | Bypass | On |
| First Scent - Pulse | Closed | CG1 Unsealed | Actuate CG1 | Pulse |
| First Scent - High | Closed | CG1 Unsealed | Actuate CG1 | High Speed |
| First Scent - Low | Closed | CG1 Unsealed | Actuate CG1 | Low Speed |
| Second Scent - Pulse | Closed | CG2 Unsealed | Actuate CG2 | Pulse |
| Second Scent - High | Closed | CG2 Unsealed | Actuate CG2 | High Speed |
| Second Scent - Low | Closed | CG2 Unsealed | Actuate CG2 | Low Speed |

Exemplary Embodiments—Cartridge Function/Operation

As indicated schematically (including in the FIGURES) according to an exemplary embodiment, a scent-dispensing apparatus for an interior space may comprise a cartridge configured to contain scent media and with a fit/interconnection arrangement providing an interface to the scent-dispensing apparatus so that scent from the scent media can be dispensed effectively into an interior space such as a vehicle interior. The apparatus/cartridge may be included/oriented in any of a wide variety of arrangements within the vehicle interior.

According to an exemplary embodiment as shown schematically, the physical form/shape of the cartridge may be adapted and configured to provide a fit/interface with the apparatus for dispensing scent; the cartridge may selectively removable/replaceable and configured to include scent media intended to provide any of a variety of selected scents/combinations to be dispensed until expended or intended for interchange (e.g. by removal/replacement of cartridge/media for selection/replacement of scent media); the cartridge may be configured with a proprietary fit/interface (e.g. data/tag, physical/body fit, seating/interconnect arrangement, etc.) to promote/ensure use of an authentic cartridge with the apparatus for dispensing scent. As indicated schematically, the cartridge will be configured with a form/fit (e.g. body, cap, inlet/outlet ports, etc.) to contain scent media and to facilitate selection of scent media for use in the scent-dispensing apparatus.

According to an exemplary embodiment as shown schematically in the FIGURES, the cartridge is configured for efficient production/supply for use in the scent-dispensing apparatus and for efficient reliable/convenient use (including assembly, filling, supply/tracking, ordering, storage, shipment, selection, installation, removal, replacement/refill, interconnect/interchange, actuation/operation, information/data transmission/communication, etc.); the cartridge is configured for efficient interoperability with the scent-dispensing apparatus (including but not limited to one or more features such as effective sealing/leak-proofing at inlet/outlet, general or proprietary fit/interconnection, maintaining shelf-life/efficacy of scent media, selection of concentration/scent for outlet/air, cleaning/maintenance, use/reuse, replacement/replenishing, selection/ordering, authentication, data/information communications, user interface, actuation/adjusting and switching, etc.).

According to an exemplary embodiment as shown schematically, a cartridge system may be provided for a scent-dispensing apparatus configured to dispense scent from scent media into air in a vehicle interior. The cartridge system may comprise a cartridge body providing a chamber for scent media and a valve assembly configured to provide an inlet port and an outlet port; the valve assembly may be configured to provide flow of air from the inlet port across scent media to the outlet port when open and to provide a seal of the chamber of the cartridge body when closed. The cartridge system may comprise a tag for data/information. The seal may comprise an air-tight leak-proof seal. The cartridge system may further comprise a cap for the body to be removed to fill/refill the chamber of the body with scent media.

According to an exemplary embodiment as shown schematically, a component for a vehicle interior may provide an inlet and an outlet configured for an open position to allow passage of air from the inlet to the outlet and a closed position to prevent passage of air from the inlet to the outlet. The component may comprise a cartridge system providing a cartridge for a scent-dispensing apparatus. The component may comprise an enclosure; a screen within the enclosure; a valve mechanism within the enclosure; and scent media within the enclosure; the valve mechanism may be configured to move within the enclosure between a sealed position and an open position. The enclosure may comprise a cap and a bottom. The cap may comprise one of the outlet; the inlet; the bottom may comprise the other of the outlet; the inlet. One of (a) the cap; (b) the bottom may comprise the outlet and the inlet. The valve mechanism may comprise a valve and a seal; at least one of (a) the valve; (b) the seal may be configured to seal at least one of (1) the inlet to prevent passage of air through the inlet; (2) the outlet to prevent passage of air through the outlet. The valve may comprise a set of valves; the seal may comprise a set of seals. The valve may comprise a valve for the inlet and a valve for the outlet; the seal may comprise a seal for the inlet and a seal for the outlet. The valve mechanism may comprise a stem configured couple movement of the valve for the inlet; the valve for the outlet; the seal for the inlet; the seal for the outlet. The valve mechanism may comprise a spring configured to bias the valve mechanism in the sealed position. The spring may be configured to compress when the valve mechanism moves from the sealed position to the open position. The valve mechanism may comprise a valve. The spring may be configured to bias the valve. The valve may be configured to compress the spring. The valve may comprise a set of valves. The screen may comprise at least one aperture. The screen may be configured to position the scent media. The open position may comprise a gapped position.

Exemplary Embodiments

According to an exemplary embodiment as shown schematically in FIGS. 8A, 28A, 30A-30B, 31A, 32A and 33A-33D, the scent dispensing apparatus (SD/C) may comprise the actuator (AC) driven by motor (MR) with slider SL and cam/follower arrangement (CM/CF) to facilitate air flow from inlet (IN) and through a valve arrangement (VA/VB) for a selected cartridge (CG) containing scent media (M) and through outlet (OT) as a scent (SN) comprising air flow infused by the scent media (M) for the selected cartridge (CG).

Figure 33D:
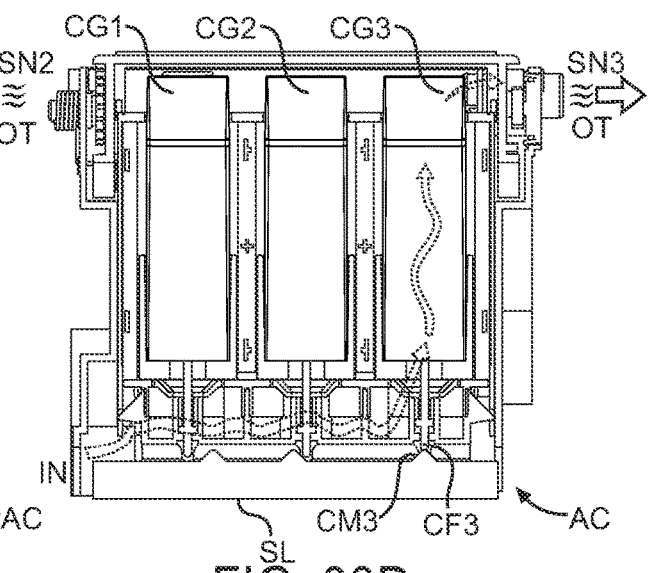

According to an exemplary embodiment as shown schematically in FIGS. 33A-33D, operation of the scent dispensing apparatus (SD/C) may comprise use of the actuator (AC) driven by motor (MR) with slider SL and cam/follower arrangement (CM/CF) to facilitate air flow from inlet (IN) and through a valve arrangement (VA/VB) for a selected cartridge (CG) containing scent media (M) and through outlet (OT) as a scent (SN) comprising air flow infused by the scent media (M) for the selected cartridge (CG). See also FIGS. 30A-30B, 31A-31B, 32A-32B. Operation of the scent dispenser may comprise an inactive state where no scent is dispensed from any cartridge with the valve arrangement for each cartridge closed (FIG. 6A); in a first state a first scent SN1 is dispensed from the first cartridge CG1 through valve arrangement opened by cam action from slider SL/actuator AC from the scent media contained within the first cartridge CG1 (FIG. 6B); in a second state a second scent SN2 is dispensed from the second cartridge CG2 through valve arrangement opened by cam action from slider SL/actuator AC from the scent media contained within the second cartridge CG2 (FIG. 33C); in a third state a third scent SN3 is dispensed from the third cartridge CG3 through valve arrangement opened by cam action from slider SL/actuator AC from the scent media contained within the third cartridge CG3 (FIG. 33D).

As indicated schematically in FIGS. 31A-31B and 32A-32B, operation of the scent dispensing apparatus for the vehicle interior may comprise selective engagement through the actuator (AC) with slider SL and cam/follower arrangement (CM/CF) of the valve arrangement (VA/VB) of a selected cartridge (CG) comprising scent media (M) to produce air flow with the corresponding selected scent (SN) as output into the passenger compartment of the vehicle; to provide scent SN1 from the scent media in first cartridge CG1 the actuator AC moves slider SL to position where cam element CM1 engages cam follower element CF1 to open the valve arrangement with valve VA1 and valve VA2 (against spring SG tending to close the valve arrangement).

As indicated schematically, to provide a first scent SN1 by airflow through the scent media in first cartridge CG1 the actuator AC moves slider SL to position where cam element CM1 engages cam follower element CF1 to open the valve arrangement with valve VA1 and valve VA2 (against spring SG tending to close the valve arrangement) for the first cartridge CG1; the valve arrangement remains closed for the other two cartridges (e.g. dispensing no scent from the two closed cartridges). See FIG. 33B.

As indicated schematically, to provide a first scent SN1 by airflow through the scent media in first cartridge CG1 the actuator AC moves slider SL to position where cam element CM1 engages cam follower element CF1 to open the valve arrangement with valve VA1 and valve VA2 (against spring SG tending to close the valve arrangement) for the second cartridge CG2; the valve arrangement remains closed for the other two cartridges (e.g. dispensing no scent from the two closed cartridges). See FIG. 33C.

As indicated schematically, to provide a third scent SN3 by airflow through the scent media in third cartridge CG3 the actuator AC may move slider SL to position where cam element CM3 engages cam follower element CF3 to open the valve arrangement with valve VA3 and valve VA3 (against spring SG tending to close the valve arrangement) for the third cartridge CG3; the valve arrangement remains closed for the other two cartridges (e.g. dispensing no scent from the two closed cartridges). See FIG. 33D.

According to an exemplary embodiment as shown schematically in FIGS. 30A-30B, 31A, 32A and 33A-33D, a component C for a vehicle interior configured to dispense scent SN from scent media M into air in a vehicle interior may comprise an inlet IN, an outlet OT; an enclosure EN configured for at least one scent-containing cartridge CG configured to contain scent media M and an actuator AC comprising a mechanism SL configured to actuate a valve arrangement (VA/VB) for each scent-containing cartridge CG between a sealed state to obstruct passage of air through scent media M of the scent-containing cartridge CG and an unsealed state to allow passage of air through scent media M of the scent-containing cartridge CG toward the outlet OT. The mechanism SL of the actuator AC may comprise a slider arrangement configured to provide cam action to open the valve arrangement (VA/VB) for a scent-containing cartridge CG for the unsealed state and to close the valve arrangement (VA/VB) for a scent-containing cartridge CG for the sealed state.

Exemplary Embodiments—System Function/Operation

Referring to FIGS. 34A-34B and 38A-38B, the system and method of operation of the module/component for dispensing scent SD/C is shown schematically according to an exemplary embodiment.

As shown schematically in FIGS. 34A-34B and 38A-38B, the system SD may comprise the module with cartridges and an interface (e.g. mechanical, data/electronic, instrumentation, network, etc.) as well as a user interface (e.g. control, touch screen, buttons, etc.) which can be provided on and/or adjacent to the module (e.g. in the vehicle accessible to an occupant through a dedicated and/or existing user interface system that may connect to other vehicle systems).

The module may provide a data interface that may comprise interaction/connection with a data/information tag on the cartridge (e.g. to register, store, monitor, interact, etc.)

and a mechanical interface that may comprise a fit/connection (e.g. proprietary connection design, etc.); as indicated.

As indicated schematically, in operation the system SD may provide an output OT/SN of scented air from an input supply IN of air from the vehicle and/or the vehicle ventilation system (or heating, ventilation, air conditioning system, etc.). According to an exemplary embodiment shown schematically in FIGS. 34A-34B and 35, the module/system may comprise a fan configured to operate at a fixed speed or to operate by modulation (e.g. pulsing, pulse-width modulation (PWM), dual speed, variable speed, etc.) to draw input air IN that will flow through the module; if a selected scent cartridge is open (e.g. actuated at the user interface and through motor MR) input air in some proportion will flow into the scent cartridge and mix into scented output air OT/SN with a fragrance from the selected scent cartridge. See generally FIGS. 36A-36C and 37A-37C (indicating operation of one selected cartridge of four potentially selectable cartridges). As indicated schematically in FIGS. 38A and 38B, the system may be configured to facilitate selection of a scent cartridge by an occupant of the vehicle using the user interface (e.g. by a control/connection that is mechanical, electronic, data, network, remote, etc.).

Figure 38A:
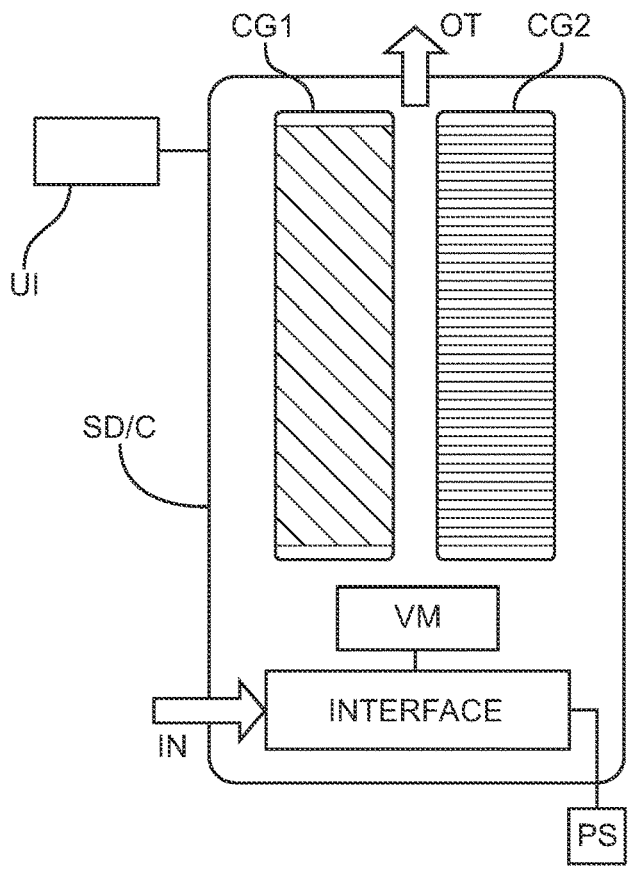
FIGS. 38A and 38B are schematic system diagrams according to an exemplary embodiment.
Figure 38B:
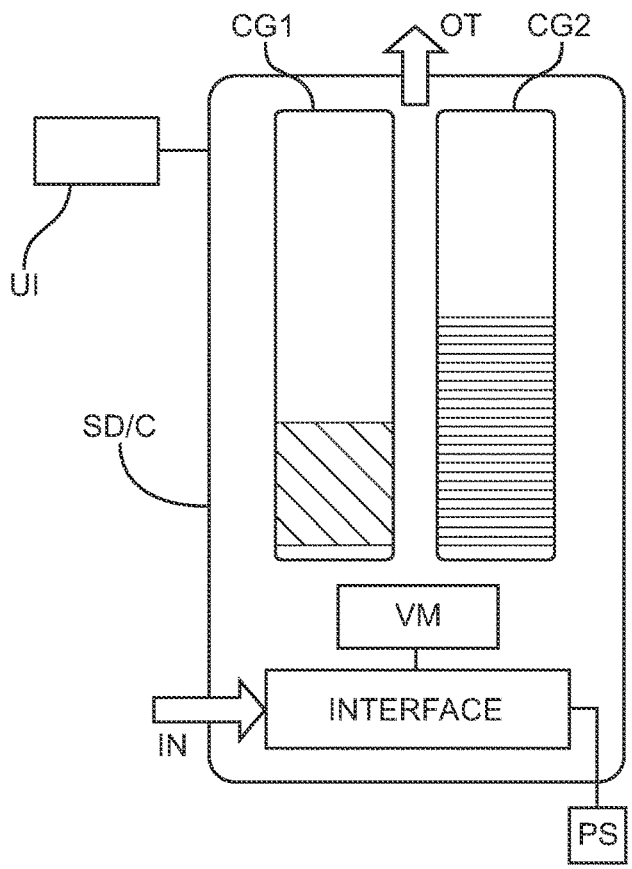
Figure 41A:
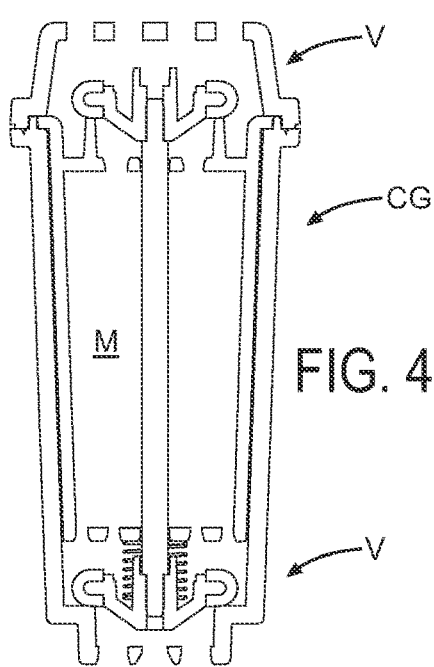
FIGS. 41A through 41D are schematic section views of an apparatus/system for dispensing scent with a cartridge according to an exemplary embodiment.
Figure 41B:
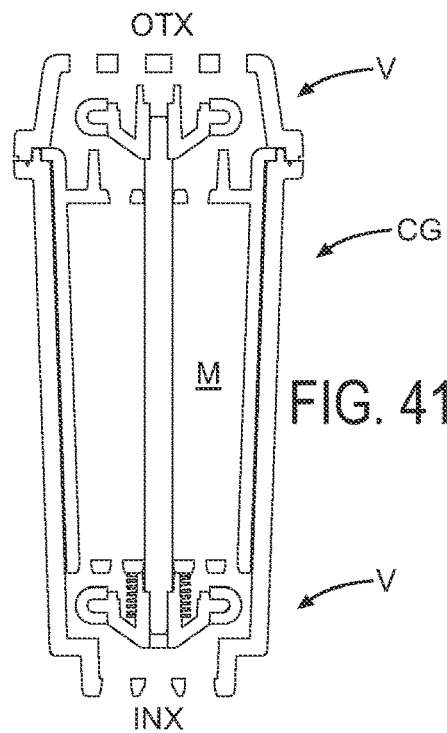
Figure 41C:
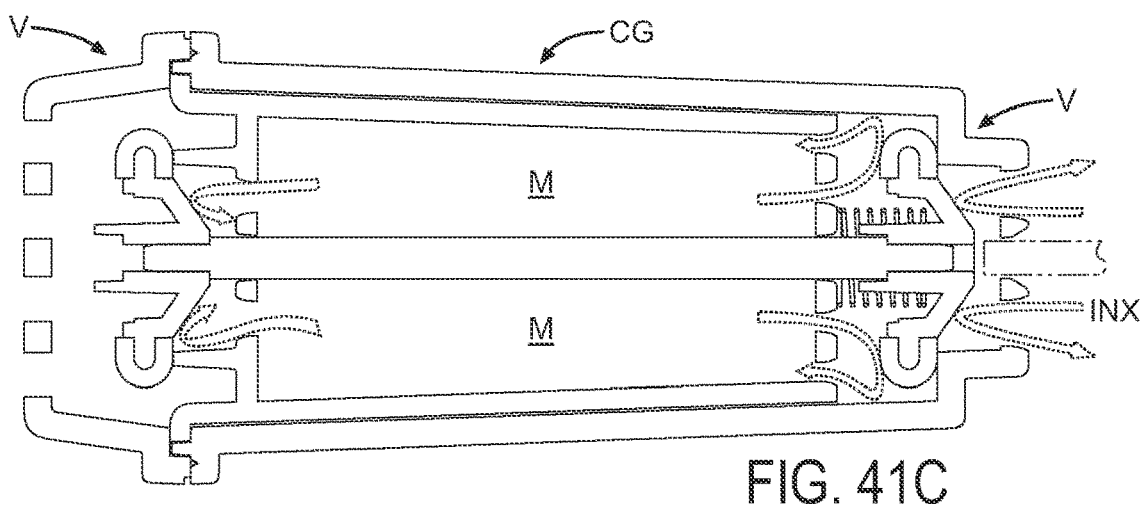
Figure 41D:
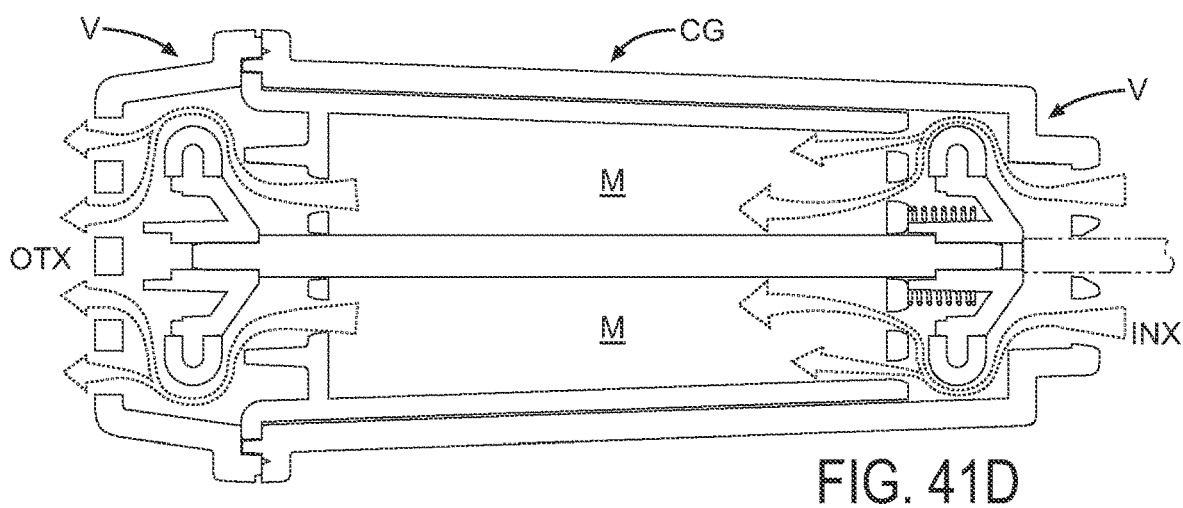
Figure 43A:
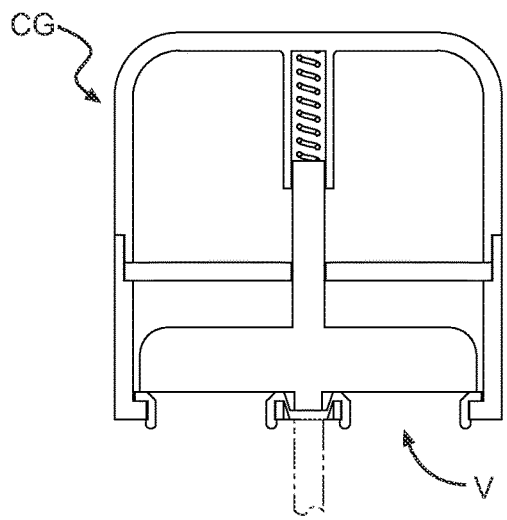
FIGS. 43A through 43D are schematic section views of an apparatus/system for dispensing scent with a cartridge according to an exemplary embodiment.
Figure 43B:
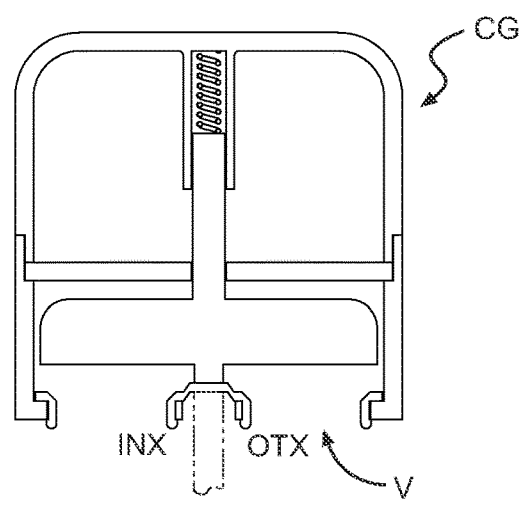
Figure 43C:
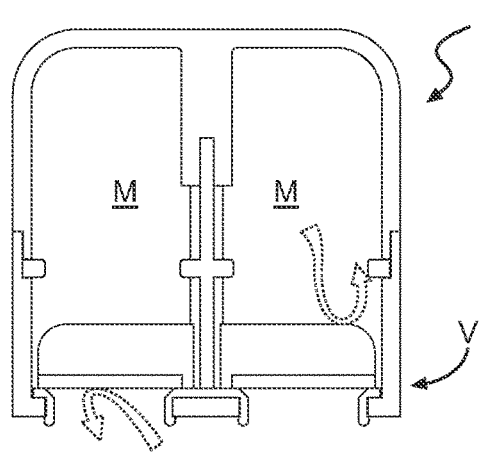
Figure 43D:
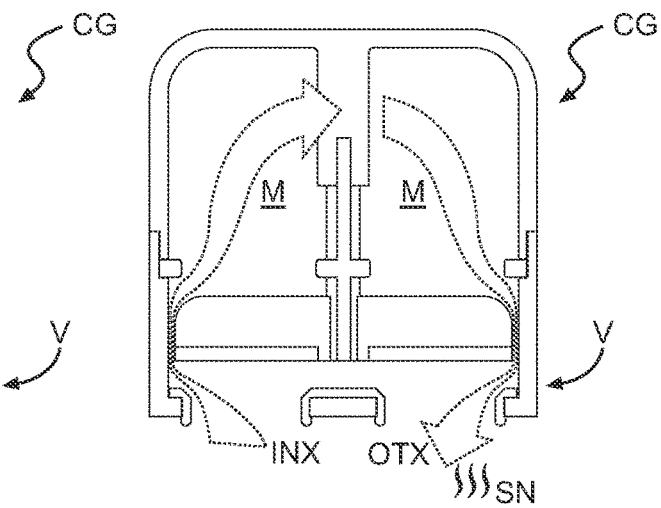
Figure 44A:
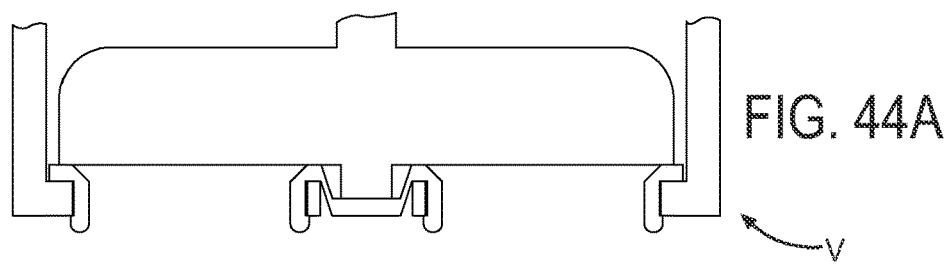
FIGS. 44A and 44B are schematic section views of an apparatus/system for dispensing scent with a cartridge according to an exemplary embodiment.
Figure 44B:
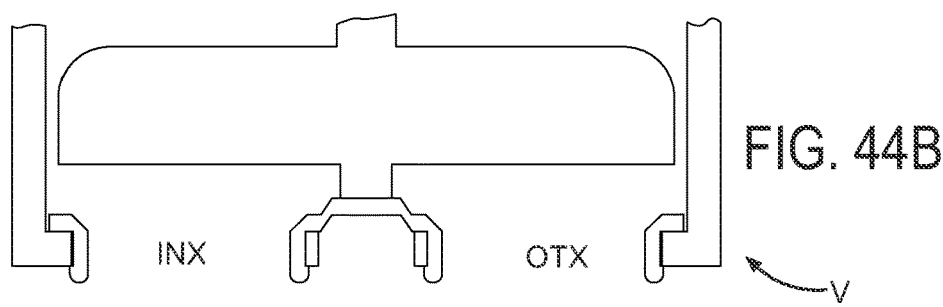

As indicated schematically according to an exemplary embodiment in FIGS. 38A-38B, the system may be configured to use data/information (e.g. from monitoring, instrumentation, interconnectivity, etc.) for use/operation of the module and/or for presentation at the user interface; for example, as indicated in FIGS. 38A and 38B, the level of efficacy/scent in a cartridge (or set of cartridges) may be monitored (e.g. by instrumentation, measurement, computation, proxy, etc.) to indicate when a replacement of a cartridge is needed (e.g. indicating that one or more cartridges are expended and/or nearly expended and to what degree).

As indicated schematically in FIGS. 38A-38B, the system may function according to a control program to facilitate operation and data display/interchange (e.g. indicated through or at the user interface and/or by the module) to present scent for the vehicle interior. The module may be activated and indicate presence/absence and/or type/compatibility of a cartridge (e.g. by detection of the tag/information at the data interface) and the state of operation of the system (e.g. by data flow/connectivity, detection, monitoring, etc.) such as whether any cartridge is depleted and/or in need of replacement (or not operational/functioning) and then may provide information/instructions to the occupant/user to take action such as replacement. As indicated schematically, operation of the system may be controlled at a user interface (e.g. access to control/information as to settings, options for operation, operating conditions, ambient conditions, etc.); for example, the module may be operated in a bypass mode (no scent) and/or with selection of one of the available/installed scent cartridges and setting of intensity of scent to be provided within an available range (e.g. by operation of the fan and/or flow control element of a cartridge, etc.); a different cartridge may be selected for diffusion of scent into the vehicle interior; the module may be turned off (e.g. operation ended). As indicated schematically, the cartridge replacement process may be guided by instructions presented at a user interface (e.g. removal/replacement of cartridges, etc.).

A component/system for a vehicle interior configured to dispense scent from scent media into air in a vehicle interior may comprise an inlet IN; an outlet OT; an enclosure EN for a scent-dispensing cartridge CG/CG1/CG2/CG3/CG4 providing scent media; and an actuator AC/AC1/AC2/AC3/AC4 to actuate the scent-dispensing cartridge between sealed and unsealed states. The component may comprise an inlet chamber IC separated from an outlet by the enclosure. The component may comprise a valve/ventilation mechanism VM comprising a fan F to direct airflow from the inlet through the outlet. The component may comprise at least one of a console; an overhead console; a floor console; a center console. The component may be configured in the form of a cup (e.g. to fit into a cupholder) and may be configured to connect to a power source PS in the vehicle (e.g. AC or DC power supply/outlet). The component/system may be connected to a network (e.g. such as a vehicle network, etc.) by an interface configured for data exchange. See FIGS. 38A-38B.

Exemplary Embodiments—General Operation

According to an exemplary embodiment as shown schematically in FIGS. 2, 5A-5B, 27A-27B, 38A-38B and 45A-45D, a vehicle interior may comprise a system comprising a component C configured to dispense scent into a vehicle interior; the component C may comprise a module SD comprising an inlet IN and an outlet OT and configured to dispense scent through actuation of a valve mechanism V/VM; and an actuation mechanism AC for the module SD. See also FIGS. 6A, 7A, 8A-8B, 10A-10D, 16A-16B, 23A-23C, 25A-25C, 27A-27B, 35, 38A-38B and 45A-45D. As indicated schematically, the module SD may be configured to contain at least one cartridge CG comprising scent media M so that scent from the scent media M is dispensed at the outlet OT of the module SD into the vehicle interior.

See FIGS. 2, 3, 5A-5B, 27A-27B, 28A-28C, 34A-34D, 38A-38B and 45A-45D. The valve mechanism VM may comprise at least one valve V configured as a flow control element between the inlet IN and the outlet OT; the actuation mechanism AC may be configured to actuate the valve mechanism V/VM; the system may comprise at least one cartridge CG; at least one cartridge CG may comprise a valve configured to be actuated by the valve mechanism V/VM; the valve mechanism V/VM may comprise a set of valves. See FIGS. 4, 5A, 11A-11D, 19A-19B, 21A-21C, 22D, 23A-23C, 25A-25C, 27A-27B, 30A-30B, 36A-36C, 37A-37C, 38A-38B, 39A-39D, 41A-41D, 43A-43D and 45A-45D.

As indicated schematically according to an exemplary embodiment, at least one cartridge CG may be removable from the module SD; at least one cartridge CG may be replaceable within the module SD. See e.g. FIGS. 9A-9B, 10A-10D, 22A-22D, 26A-26C, 29A-29C and 46. At least one cartridge CG may comprise a set of cartridges; the set of cartridges may comprise a first scent cartridge comprising first scent media M to provide a first scent and a second scent cartridge comprising second scent media M to provide a second scent; the set of cartridges may comprise a third scent cartridge comprising third scent media M to provide a third scent. See e.g. FIGS. 5A-5B.

The actuation mechanism AC may be configured to actuate the valve mechanism V/VM; the valve mechanism V/VM may comprise a first valve assembly for the first scent cartridge and a second valve assembly for the second scent cartridge; the actuation mechanism AC may be configured to actuate the first scent cartridge and the second scent cartridge. See FIGS. 5A-5B and 45A-45B. The actuation mechanism AC may be configured to actuate a valve of the first valve assembly and a valve of the second valve assembly; the actuation mechanism AC may comprise a cam mechanism CM; the actuation mechanism AC may comprise a cam mechanism CM operated by a controller. See e.g. FIGS. 10A-10D, 13A-13C, 14A-14F, 15A-15F, 16A-16C and 45A-45D. At least one cartridge CG may comprise a first scent cartridge comprising first scent media M and a first valve assembly and a second scent cartridge comprising second scent media M and a second valve assembly; the valve mechanism V/VM may comprise the first valve assembly and the second valve assembly; the actuation mechanism AC may comprise a cam mechanism CM configured to actuate the valve mechanism V/VM. A mechanism such as a cam mechanism may be configured to selectively open and close a valve of the first valve assembly for the first scent cartridge and to selectively open and close a valve of the second valve assembly of the second scent cartridge. See e.g. FIGS. 4, 5A, 11A-11D, 19A-19B, 21A-21C, 22D, 23A-23C, 25A-25C, 27A-27B, 30A-30B, 36A-36C, 37A-37C, 38A-38B, 39A-39D, 41A-41D, 43A-43D and 45A-45D. The cam mechanism CM may be configured to selectively open and close a set of valves of the first valve assembly for the first scent cartridge and to selectively open and close a set of valves of the second valve assembly of the second scent cartridge. The actuation mechanism AC may be operated by a controller and configured to selectively operate the valve mechanism V/VM to open and close a flow control element (shown as valve V) of the first valve assembly for the first scent cartridge and to open and close a valve of the second valve assembly of the second scent cartridge. See e.g. FIGS. 4, 5A, 11A-11D, 19A-19B, 21A-21C, 22D, 23A-23C, 25A-25C, 27A-27B, 30A-30B, 36A-36C, 37A-37C, 38A-38B, 39A-39D, 41A-41D, 43A-43D and 45A-45D.

As indicated schematically, the system may comprise a fan FN configured to provide air flow through the module SD. See FIGS. 5B and 45C-45D. As indicated schematically in FIGS. 5A-5B, 27A-27B, 38A-38B and 45A-45D, the valve mechanism V/VM may comprise at least one valve; the fan FN may be configured to provide air flow through at least one valve.

As indicated schematically in FIGS. 5A-5B, 27A-27B, 38A-38B and 45A-45D, the system may comprise at least one cartridge CG; at least one cartridge CG may comprise a first scent cartridge comprising first scent media M and a first valve assembly and a second scent cartridge comprising second scent media M and a second valve assembly; the valve mechanism V/VM may comprise the first valve assembly and the second valve assembly; the actuation mechanism AC may be configured to actuate the valve mechanism V/VM; the actuation mechanism AC may be configured to selectively operate the valve mechanism V/VM to open and close a valve of the first valve assembly for the first scent cartridge and to open and close a valve of the second valve assembly of the second scent cartridge. See also FIGS. 21A-21C, 22D, 23A-23C, 25A-25C, 30A-30B, 36A-36C, 37A-37C, 39A-39D, 41A-41D and 43A-43D. A fan FN may be configured to provide air flow through the valve of the first valve assembly into the first scent cartridge and through the valve of the second valve assembly into the second scent cartridge. The actuation mechanism AC may comprise a cam mechanism CM configured to selectively operate the valve mechanism V/VM to open and close a valve of the first valve assembly for the first scent cartridge and to open and close a valve of the second valve assembly of the second scent cartridge. See FIGS. 10A-10D, 13A-13C, 14A-14F, 15A-15F, 16A-16C and 35.

As indicated schematically in FIGS. 5A-5B and 45A-45D, a fan FN may be configured to provide air flow through the valve of the first valve assembly into the first scent cartridge and through the valve of the second valve assembly into the second scent cartridge; the system may be configured to provide the first scent during air flow through the first cartridge and the second scent during air flow through the second cartridge; the first cartridge may be sealed from air flow during air flow through the second cartridge and the second cartridge may be sealed from air flow during air flow through the first cartridge. See also FIGS. 4 and 46. The first valve assembly for the valve mechanism V/VM may comprise a set of valves; the second valve assembly may comprise a set of valves. See FIGS. 4, 5A, 27A-27B, 38A-38B and 45A-45D.

According to an exemplary embodiment as shown schematically in FIGS. 45A-45D, the system may comprise a control system for the module; the control system may comprise a controller for the module; the controller may be configured to operate the actuation mechanism/actuator; the controller may be configured to operate the fan FN; the controller may be operated through a user interface UI for the module/system. See also FIG. 46.

According to an exemplary embodiment as shown schematically in FIGS. 45A-45D and 46, the system may be operated in a vehicle by a process comprising the steps of: (a) activating a user interface UI for the module SD; (b) detecting a cartridge in the module SD. The user interface UI of the module SD may comprise control of at least one of (1) selection of scent; (2) operation of a fan FN; (3) display of information; (4) replacement of a cartridge; (5) cancellation of a command; (6) shut off of the module SD. See FIGS. 45A-45D and 46. The system may comprise at least one cartridge CG; at least one cartridge CG may comprise a first scent cartridge comprising first scent media M and a first valve assembly and a second scent cartridge comprising second scent media M and a second valve assembly; the valve mechanism V/VM may comprise the first valve assembly and the second valve assembly; the actuation mechanism AC may be configured to actuate the valve mechanism V/VM. See FIGS. 5A-5B, 45A-45D and 46. The fan FN may be configured to provide air flow through the valve of the first valve assembly into the first scent cartridge and through the valve of the second valve assembly into the second scent cartridge. See FIGS. 5A-5B, 45C-45D and 46.

The system may be configured to provide the first scent during air flow through the first cartridge and the second scent during air flow through the second cartridge; the first cartridge may be sealed from air flow during air flow through the second cartridge and the second cartridge may be sealed from air flow during air flow through the first cartridge. See FIGS. 5A-5B, 27A-27B, 38A-38B, 45A-45D and 46

As indicated schematically in FIGS. 45A-45D and 46, the system may be operated by a process further comprising the step of obtaining data from the vehicle for the controller of the module (e.g. data for interchange with and/or transmission to a vehicle network, internet/network, cloud/network, etc.); the data may comprise data from the vehicle interior; at least one cartridge CG may comprise an identification tag TG; data may comprise data from the identification tag TG. See FIGS. 4, 5A-5B, 45A-45D and 46.

As indicated schematically, the system may comprise an interface; the interface may comprise at least one of a data/network interface and a mechanical interface. See FIGS. 22D and 45A-45D. The system may comprise a power source/supply PS for the actuation mechanism AC. See FIGS. 45A-45D. The system may comprise a vehicle interior component C/SD comprising the module SD. See FIG. 2.

According to an exemplary embodiment, the vehicle interior component providing the scent-dispensing module/apparatus may comprise at least one of a console, overhead console, floor console, center console, armrest, trim panel, instrument panel, etc. See FIGS. 1A-1B and 2.

According to an exemplary embodiment as shown schematically in FIGS. 5A-5B and 45A-45D, a vehicle interior component C may comprise a module/apparatus SD configured to dispense scent from scent media M into air in a vehicle interior and may comprise an inlet IN; an outlet OT; an enclosure EN configured for at least one scent-containing cartridge arrangement providing scent media M (e.g. media contained within the body of the cartridge); and an actuator AC configured to actuate at least one scent-containing cartridge arrangement between a sealed state and an unsealed state (e.g. through a valve arrangement configured to open and close). See also FIGS. 27A-27B, 38A-38B (interface providing actuator for valve mechanism for module). As shown schematically according to an exemplary embodiment, at least one scent-containing cartridge arrangement may comprise a first scent-containing cartridge arrangement and a second scent-containing cartridge arrangement; at least one scent-containing cartridge arrangement may comprise a third scent-containing cartridge arrangement; at least one scent-containing cartridge arrangement may comprise a fourth scent-containing cartridge arrangement. See also FIGS. 10A-10D, 13A-13C, 14A-14F, 15A-15F, 16A-16C and 35.

As indicated schematically in FIGS. 13A-13C and 46, the actuator AC may be configured for (a) a bypass state with the first scent-containing cartridge arrangement in a sealed state and the second scent-containing cartridge arrangement in a sealed state and the third scent-containing cartridge arrangement in a sealed state and the fourth scent-containing cartridge arrangement in a sealed state; (b) a first actuation state actuating the first scent-containing cartridge arrangement in an unsealed state with the second scent-containing cartridge arrangement in the sealed state and the third scent-containing cartridge arrangement in the sealed state and the fourth scent-containing cartridge arrangement in the sealed state; (c) a second actuation state actuating the second scent-containing cartridge arrangement in an unsealed state with the first scent-containing cartridge arrangement and the third scent-containing cartridge arrangement in the sealed state and the fourth scent-containing cartridge arrangement in the sealed state; (d) a third actuation state actuating the third scent-containing cartridge arrangement in an unsealed state with the first scent-containing cartridge arrangement and the second scent-containing cartridge arrangement in the sealed state and the fourth scent-containing cartridge arrangement in the sealed state; (e) a fourth actuation state actuating the fourth scent-containing cartridge arrangement in an unsealed state with first scent-containing cartridge arrangement, the second scent-containing cartridge arrangement and the third scent-containing cartridge arrangement in the sealed state. See also FIGS. 5A-5B and 45A-45D. The actuator AC/mechanism may comprise a motor MR and a slider arrangement SL and may be configured for (a) a position to provide the bypass state; (b) a position to provide the first actuation state; (c) a position to provide the second actuation state; (d) a position to provide the third actuation state; (e) a position to provide the fourth actuation state. See FIGS. 10A-10D, 13A-13C, 14A-14F, 15A-15F and 16A-16C. The actuator AC may comprise (a) a cam/follower arrangement to operate a valve arrangement for the first cartridge arrangement; (b) a cam/follower arrangement to operate a valve arrangement for the second cartridge arrangement; (c) a cam/follower arrangement to operate a valve arrangement for the third cartridge arrangement; (d) a cam/follower arrangement to operate a valve arrangement for the fourth cartridge arrangement. See FIGS. 10A-10D, 13A-13C, 14A-14F, 15A-15F and 16A-16C.

As indicated schematically in FIGS. 10A-10D and 11A-11D, component C/SD may comprise a latch configured for (a) a latched state to secure at least one cartridge CG arrangement; (b) an unlatched state to present at least one cartridge CG arrangement for replacement. The component C/SD may comprise at least one plunger and at least one spring configured to present at least one cartridge CG arrangement for replacement; the component C/SD may comprise a catch; the latch may be configured to secure at least one cartridge CG arrangement at the catch. See FIGS. 10A-10D and 11A-11D.

As indicated schematically, the actuator AC/mechanism may comprise a motor MR and a cam shaft and may be configured for (a) a position to provide the bypass state; (b) a position to provide an actuation state. See FIGS. 10A-10D, 13A-13C, 14A-14F, 15A-15F and 16A-16C. The actuator AC may be configured to rotate to operate a valve arrangement for a cartridge arrangement. See e.g. FIGS. 4 and 38A-38B.

Figure 4:
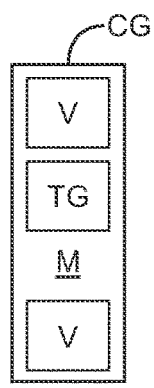
FIG. 4 is a schematic diagram of a cartridge for an apparatus for dispensing scent according to an exemplary embodiment.
Figure 6A:
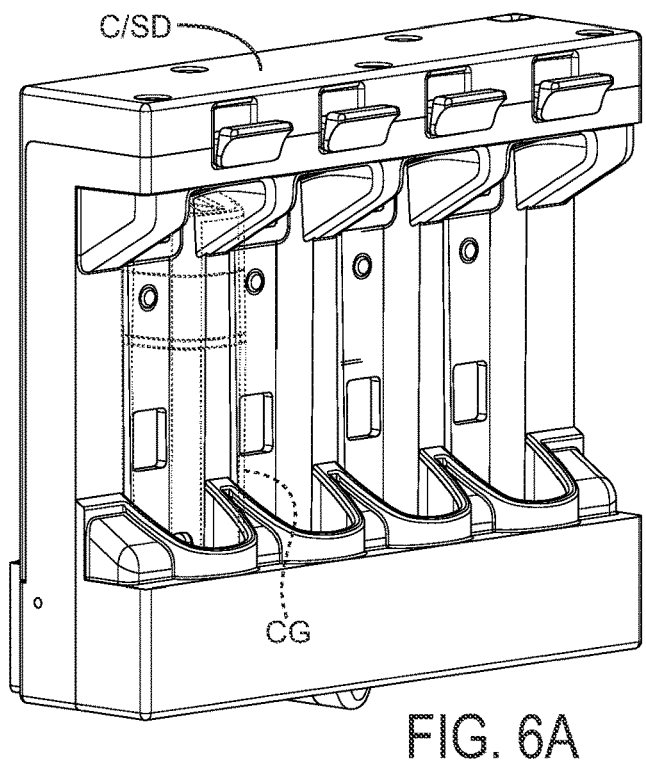
FIG. 6A is a schematic perspective view of a component/apparatus for dispensing scent according to an exemplary embodiment.
Figure 6B:
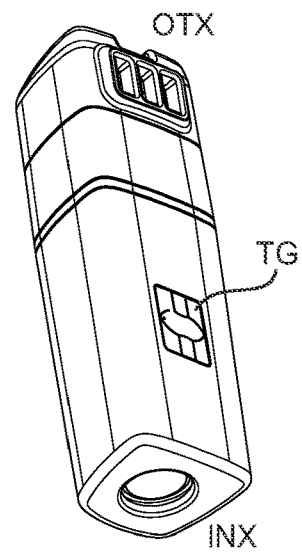
FIGS. 6B and 6C are schematic perspective views of an apparatus/system for dispensing scent with a cartridge according to an exemplary embodiment.
Figure 6C:
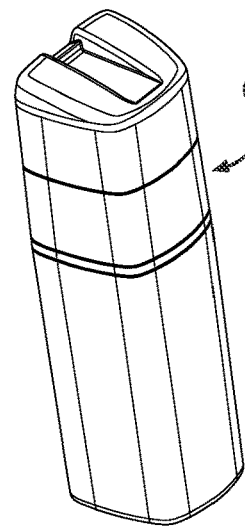
Figure 7A:
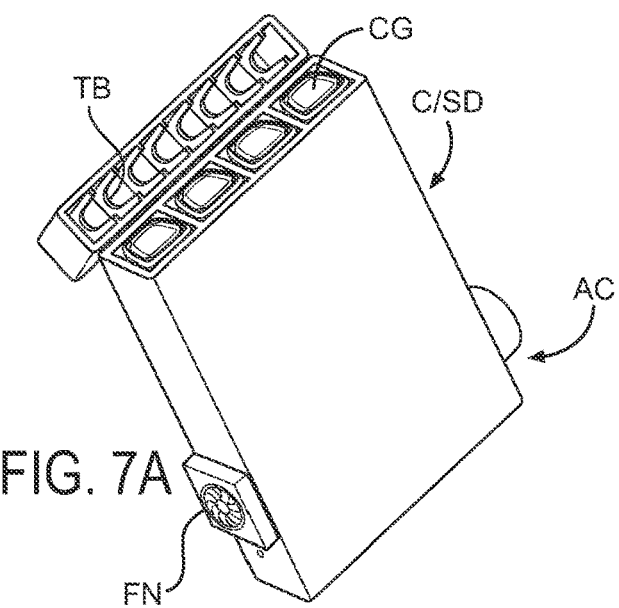
FIG. 7A is a schematic perspective view of a component/apparatus for dispensing scent according to an exemplary embodiment.
Figure 7B:
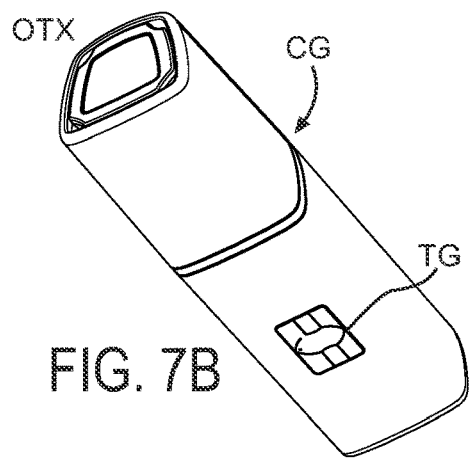
FIG. 7B is a schematic perspective view of an apparatus/system for dispensing scent with a cartridge according to an exemplary embodiment.

As indicated schematically according to an exemplary embodiment in FIGS. 4 and 6B-6C, the cartridge may comprise an inlet port INX and an outlet port OTX; the inlet port INX may be positioned at a bottom surface of the cartridge and the outlet port OTX may be positioned at a rear surface of the cartridge; the inlet port INX may be positioned at a bottom surface of the cartridge and the outlet port OTX may be positioned at a top surface of the cartridge generally opposite the bottom surface of the cartridge; the inlet port INX may be positioned at a bottom surface of the cartridge and the outlet port OTX may be positioned at a bottom surface of the cartridge.

According to an exemplary embodiment as shown schematically in FIGS. 5A-5B, 27A-27B, 38A-38B and 45A-45D, a vehicle interior component C may comprise a module/apparatus SD configured to dispense scent from scent media M into air in a vehicle interior comprising an inlet IN; an outlet OT; an enclosure configured for at least one scent cartridge CG providing scent media M; and an actuator AC configured to actuate at least one scent cartridge CG between a sealed state and an unsealed state; at least one scent cartridge CG may comprise a first scent cartridge and a second scent cartridge; the actuator AC may be configured for (a) a bypass state with the first scent cartridge in a sealed state and the second scent cartridge in a sealed state; (b) a first actuation state actuating the first scent cartridge in an unsealed state with the second scent cartridge in the sealed state; (c) a second actuation state actuating the second scent cartridge in an unsealed state with the first scent cartridge in the sealed state; the actuator AC may comprise (a) an actuator AC for the first scent cartridge; (b) an actuator AC for the second scent cartridge; the actuator AC may comprise a cam shaft configured to (a) actuate the first scent cartridge from the sealed state to the unsealed state to allow passage of air through scent media M of the first scent cartridge toward the outlet OT; (b) actuate the second scent cartridge from the sealed state to the unsealed state to allow passage of air through scent media M of the second scent cartridge toward the outlet OT. See e.g. FIGS. 10A-10D, 13A-13C, 14A-14F, 15A-15F and 16A-16C. The cam shaft may be configured for (a) a position to provide the bypass state; (b) a position to provide the first actuation state; (c) a position to provide the second actuation state. See e.g. FIGS. 10A-10D, 13A-13C, 14A-14F, 15A-15F and 16A-16C.

As indicated schematically in FIGS. 8A-8C, the component C/SD may comprise a cover CV configured for (a) a closed state to conceal at least one scent cartridge CG; (b) an open state to expose at least one scent cartridge CG; when the cover CV is in the open state, the actuator AC may be configured for at least one of (a) an inaccessible state with the first scent cartridge in an inaccessible position and the second scent cartridge in an inaccessible position; (b) a first accessible state actuating the first scent cartridge in an accessible position for replacement with the second scent cartridge in the inaccessible position; (c) a second accessible state actuating the second scent cartridge in an accessible position for replacement with the first scent cartridge in the inaccessible position. The component C/SD may comprise a spring configured to move the first scent cartridge and the second scent cartridge to an accessible position for replacement in response to movement of the cover CV from the closed state to the open state. The cover CV may be configured to compress the spring in the closed state. As indicated schematically according to an exemplary embodiment, the component C/SD may comprise a release mechanism such as a latch L configured to move at least one scent cartridge CG to an accessible position for replacement in response to an external force. See e.g. FIGS. 8A-8C and 10A-10D. The component C/SD may comprise a cover CV configured for (a) a closed state to conceal at least one scent cartridge CG; (b) an open state to expose at least one scent cartridge CG; the cover CV may comprise the outlet OT. The component C/SD may comprise an inlet duct ID and an outlet duct OD. The inlet duct ID may be separated from outlet duct OD by the enclosure EN. The component C/SD may comprise a cover CV for at least one scent cartridge CG; the cover CV may be configured to form the outlet duct OD. The actuator AC may be positioned at an end of the inlet duct ID. The component C/SD may comprise a fan FN. The fan FN may be configured to direct air (a) to the inlet duct ID; (b) through scent media M of at least one scent cartridge CG; (c) through the outlet duct OD; (d) to the outlet OT. The component C/SD may comprise a bypass duct BD; the fan FN may be configured to direct air (a) to the inlet duct ID; (b) through the bypass duct BD; (c) through the outlet duct OD; (d) to the outlet OT. The fan FN may be configured to direct air (a) to the inlet duct ID; (b) through the bypass duct BD and through scent media M of at least one scent cartridge CG; (c) through the outlet duct OD; (d) to the outlet OT. See e.g. FIGS. 13A-13C and 45A-45D. As indicated schematically in FIGS. 45A-45D and 46, the fan FN may be configured for at least one of an off state and an on state; the fan FN may be configured for a high speed state and a low speed state; the fan FN may provide a high intensity scent dispersion and a low intensity scent dispersion. The fan FN may be positioned at an end of the inlet duct ID. See e.g. FIGS. 5A-5B.

As indicated schematically in FIGS. 11A-11D, the actuator AC may be configured to compress a spring of at least one scent cartridge CG to actuate at least one scent cartridge CG from the sealed state to the unsealed state to allow passage of air through the scent media M toward the outlet OT.

According to an exemplary embodiment as shown schematically in FIGS. 5A-5B, 27A-27B, 38A-38B, 45A-45D and 46, a system for a vehicle interior may comprise a component C/SD configured to dispense scent from scent media M contained in at least one cartridge CG into air in a vehicle interior comprising an inlet IN and an outlet OT and an enclosure configured for at least one cartridge CG providing scent media M and an actuator AC configured to actuate at least one cartridge CG between a sealed state and an unsealed state and a user interface UI; the user interface UI may be configured to facilitate the selection of scent by selection of at least one cartridge CG for actuation; the user interface UI may be configured for selection of intensity of scent from at least one cartridge CG.

Figure 5A:
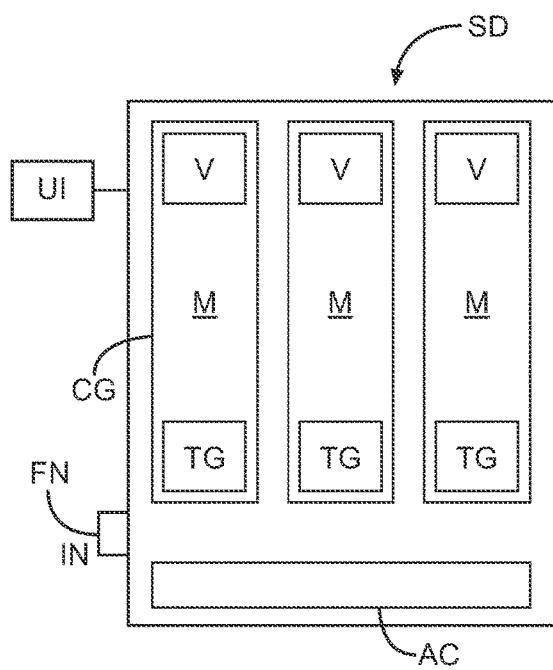
FIGS. 5A and 5B are schematic diagrams of a component/apparatus for dispensing scent according to an exemplary embodiment.
Figure 5B:
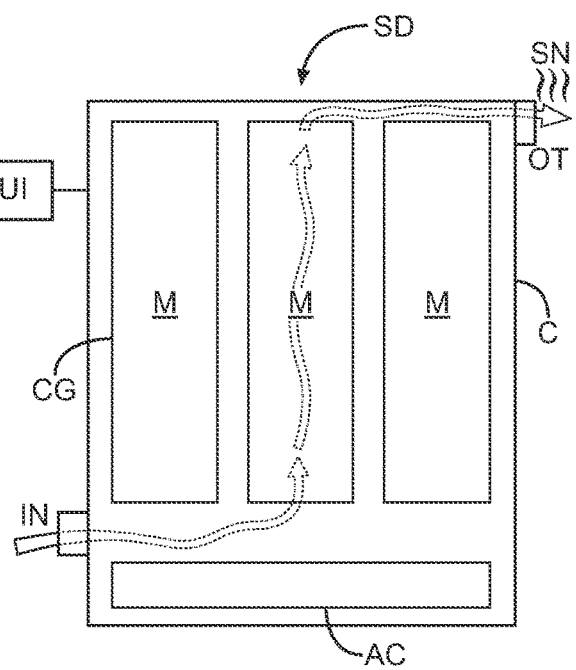

According to an exemplary embodiment as shown schematically in FIGS. 5A-5B, a vehicle interior component C/SD may comprise an apparatus SD configured to dispense scent from scent media M contained in at least one cartridge CG into air in a vehicle interior; the apparatus SD may comprise an inlet IN and an outlet OT and a chamber configured for at least one scent cartridge CG providing scent media M and an actuator AC configured to actuate at least one cartridge CG between a sealed state and an unsealed state; scent may be dispensed from the outlet OT by selection of at least one cartridge CG.

According to an exemplary embodiment as shown schematically in FIGS. 5A-5B and 45A-45D, a vehicle interior component C may comprise a module SD configured to dispense scent from scent media M contained in at least one interchangeable cartridge CG into air in a vehicle interior comprising an enclosure configured for at least one interchangeable scent-dispensing cartridge comprising scent media M and an actuator AC configured to actuate at least one cartridge CG to dispense scent and an interface between at least one cartridge CG and the enclosure; the chamber is configured so that at least one cartridge CG can be removed and replaced with at least one cartridge CG; the interface may comprise at least one of a data/network interface and a mechanical interface. See e.g. FIGS. 22D and 45A-45D.

According to an exemplary embodiment as shown schematically in FIGS. 5A-5B and 45A-45D, a vehicle interior component C/SD may comprise a cartridge system CG configured to dispense scent from scent media M into air in a vehicle interior. The cartridge system CG may comprise a cartridge comprising a body providing a chamber for scent media M and a valve assembly configured to provide an inlet port INX and an outlet port OTX; the valve assembly may be configured to provide flow of air from the inlet port INX across scent media M to the outlet port OTX when open and to provide a seal of the chamber of the body when closed. The seal may comprise an air-tight leak-proof seal (e.g. flow control element configured to prevent air flow). The cartridge system CG may further comprise a cap CP for the body to be removed to fill/refill the chamber of the body with scent media M. See e.g. FIGS. 39A-39C. The cartridge system CG may comprise a tag TG for data/information. See e.g. FIGS. 4, 5A, 45A-45D and 46.

According to an exemplary embodiment as shown schematically in FIGS. 5A-5B and 45A-45D, a vehicle interior component C/SD for a vehicle interior may provide an inlet IN and an outlet OT configured for an open position to allow passage of air from the inlet IN to the outlet OT and a closed position to prevent passage of air from the inlet IN to the outlet OT. The component C/SD may comprise an enclosure; a chamber/screen within the body of the cartridge for scent media; a valve mechanism V/VM within the body; and scent media M within the body; the valve mechanism V/VM may be configured to move between a sealed position and an open position. As indicated schematically in FIGS. 12A-12C, the cartridge CG may comprise a cap CP and a bottom. The cap CP may comprise one of the outlet or the inlet (the bottom may comprise the other of the outlet or inlet). The valve mechanism V/VM may comprise a flow control element comprising a valve and/or a seal; at least one of the valve or the seal may be configured to seal at least one of the inlet to prevent passage of air through the inlet or the outlet to prevent passage of air through the outlet; the valve may comprise a set of valves; the seal may comprise a set of seals; the valve may comprise a valve for the inlet and a valve for the outlet; the seal may comprise a seal for the inlet and a seal for the outlet. See e.g. FIGS. 4, 5A, 11A-11D, 19A-19B, 21A-21C, 22D, 23A-23C, 25A-25C, 27A-27B, 30A-30B, 36A-36C, 37A-37C, 38A-38B, 39A-39D, 41A-41D, 43A-43D and 45A-45D. The valve mechanism V/VM may comprise a connecting member shown as stem ST configured to couple movement of the valve for the inlet IN; the valve for the outlet OT; the seal for the inlet IN; the seal for the outlet OT. See e.g. FIGS. 28A-28E, 39A-39D. The valve for the inlet IN may be configured to move relative to the valve for the outlet OT. The valve mechanism V/VM may comprise a spring for the inlet IN and a spring for the outlet OT. At least one of the spring for the inlet IN and/or the spring for the outlet OT may be configured to compress when the valve mechanism V/VM moves from the sealed position to the open position. The spring for the inlet IN and the spring for the outlet OT may be configured to compress when the valve mechanism V/VM moves from the sealed position to the open position. The valve mechanism V/VM may be configured for movement to a transitional position to (1) allow passage of air through the inlet IN and (2) prevent passage of air through the outlet OT. The valve mechanism V/VM may comprise a spring configured to bias the valve mechanism V/VM in the sealed position. The spring may be configured to compress when the valve mechanism V/VM moves from the sealed position to the open position. The valve mechanism V/VM may comprise a valve. The spring may be configured to bias the valve. The valve may be configured to compress the spring. The valve may comprise a set of valves. The screen may comprise at least one aperture. The screen may be configured to position the scent media M. The open position may comprise a gapped position.

According to an exemplary embodiment as shown schematically in FIGS. 4, 5A-5B and 45A-45D, a vehicle interior component C/SD may comprise a cartridge system CG configured to dispense scent from scent media M into air in a vehicle interior comprising (a) a cartridge comprising a body providing a chamber for scent media M; (b) a valve assembly configured to provide an inlet port INX and an outlet port OTX. See also FIGS. 6A-6D and 12A-12C. As indicated schematically in FIGS. 4, 5A-5B, 21A-21C, 27A-27B and 38A-38B, the valve assembly may be configured for (1) an enclosed state to provide a seal at the inlet port INX and a seal at the outlet port OTX; (2) a transitional state to provide a seal at one of the inlet port INX and the outlet port OTX and to provide flow of air through the other of the inlet port INX and the outlet port OTX; (3) a pass-through state to provide flow of air through the inlet port INX across scent media M through the outlet port OTX. See also FIGS. 11A-11D, 19A-19B, 22D, 23A-23C, 25A-25C, 30A-30B, 36A-36C, 37A-37C, 39A-39D, 41A-41D, 43A-43D and 45A-45D. The valve mechanism V/VM may comprise a valve and a seal (e.g. operating as flow control elements); at least one of the valve and/or the seal may be configured to seal at least one of the inlet to prevent passage of air or the outlet to prevent passage of air. The valve may comprise a set of valves; the seal may comprise a set of seals. The valve may comprise a valve for the inlet port INX and a valve for the outlet port OTX; the seal may comprise a seal for the inlet port INX and a seal for the outlet port OTX. The valve for the inlet port INX may be configured to move relative to the valve for the outlet port OTX. The valve mechanism V/VM may comprise a spring for the inlet port INX and a spring for the outlet port OTX. At least one of (a) the spring for the inlet port INX; (b) the spring for the outlet port OTX may be configured to compress when the valve mechanism V/VM moves from the enclosed state to the transitional state. The spring for the inlet port INX and the spring for the outlet port OTX may be configured to compress when the valve mechanism V/VM moves from the enclosed state to the pass-through state.

According to an exemplary embodiment as shown schematically in FIGS. 4, 6A-6C and 12A-12C, a vehicle interior component C/SD may comprise a cartridge system CG configured to dispense scent from scent media M into air in a vehicle interior comprising: (a) a cartridge comprising a body providing a chamber for scent media M; (b) a valve assembly configured to provide an inlet port INX and an outlet port OTX. The valve assembly may comprise an inlet valve configured to provide the inlet port INX and an outlet valve configured to provide the outlet port OTX. The inlet valve may be configured (1) to move relative to the outlet port OTX to provide flow of air from the inlet port INX across scent media M to the outlet port OTX when open and (2) to provide a seal of the chamber of the body when closed. The inlet valve may be configured to move the outlet valve to provide flow of air across scent media M through the outlet port OTX. See FIGS. 4 and 5A-5B.

According to an exemplary embodiment as shown schematically, a vehicle interior component C/SD may comprise a cartridge system CG configured to dispense scent from scent media M into air in a vehicle interior comprising: (a) a cartridge comprising a body providing a chamber for scent media M; (b) a valve assembly configured to provide an inlet port INX and an outlet port OTX. See e.g. FIGS. 4, 5A, 11A-11D, 19A-19B, 21A-21C, 22D, 23A-23C, 25A-25C, 27A-27B, 30A-30B, 36A-36C, 37A-37C, 38A-38B, 39A-39D, 41A-41D, 43A-43D and 45A-45D. The valve assembly may comprise an inlet valve configured to provide the inlet port INX and an outlet valve configured to provide the outlet port OTX. The body may comprise an inlet section and an outlet section. The inlet valve may be configured (1) to move relative to the outlet port OTX to provide flow of air from the inlet port INX across scent media M to the outlet port OTX when open and (2) to provide a seal of the chamber of the body when closed. The inlet valve may be configured to move the outlet valve to provide flow of air across scent media M through the outlet port OTX. The inlet section may comprise the chamber for scent media M and the outlet section may comprise an outlet chamber. The outlet section may comprise the outlet valve. The inlet section may comprise the inlet valve.

According to an exemplary embodiment as shown schematically, a vehicle interior component C may comprise a module/apparatus SD configured to dispense scent from scent media M into air in a vehicle interior comprising: an inlet IN; an outlet OT; an enclosure configured for at least one scent cartridge CG providing scent media M; and an actuator AC configured to actuate at least one scent cartridge CG between a sealed state and an unsealed state. See e.g. FIGS. 4, 5A, 11A-11D, 19A-19B, 21A-21C, 22D, 23A-23C, 25A-25C, 27A-27B, 30A-30B, 36A-36C, 37A-37C, 38A-38B, 39A-39D, 41A-41D, 43A-43D and 45A-45D. At least one scent cartridge CG may comprise a first scent cartridge and a second scent cartridge. The actuator AC may comprise (a) an actuator AC for the first scent cartridge; (b) an actuator AC for the second scent cartridge. The actuator AC may be configured to (a) rotate in a first direction to actuate the first scent cartridge and (b) rotate in a second direction generally opposite the first direction to actuate the second scent cartridge. The actuator AC may be configured for (a) a default state with the first scent cartridge in a sealed state and the second scent cartridge in a sealed state; (b) a first actuation state actuating the first scent cartridge in an unsealed state with the second scent cartridge in the sealed state; (c) a second actuation state actuating the second scent cartridge in an unsealed state with the first scent cartridge in the sealed state. The actuator AC may comprise a shaft configured to (a) actuate the first scent cartridge from the sealed state to the unsealed state to allow passage of air through scent media M of the first scent cartridge toward the outlet OT; (b) actuate the second scent cartridge from the sealed state to the unsealed state to allow passage of air through scent media M of the second scent cartridge toward the outlet OT. The shaft may be configured for (a) a first position to provide the first actuation state; (b) a second position to provide the second actuation state; (c) a third position to provide the default state. The first position may comprise an extended position; the second position may comprise a retracted position; the third position may comprise a middle position. The component C/SD may comprise a motor MR configured to move the shaft between the first position; the second position; the third position. The shaft may be configured to translate to actuate an actuator AC to rotate to actuate the first scent cartridge. The actuator AC may comprise a seesaw mechanism. The seesaw mechanism may comprise an arm comprising (a) an actuator AC for the first scent cartridge; (b) an actuator AC for the second scent cartridge. The seesaw mechanism may comprise a motor MR and a shaft; the motor MR may be configured to move the shaft at an end of the arm to rotate the arm. The actuator AC may comprise an arm configured to rotate to actuate at least one scent cartridge CG. At least one scent cartridge CG may comprise a first scent cartridge and a second scent cartridge; the actuator AC may comprise a motor MR configured to pull the arm toward the motor MR to actuate the first scent cartridge; the motor MR may be configured to push the arm to actuate the second scent cartridge. The component C/SD may comprise a cover CV configured for (a) a closed state to conceal at least one scent cartridge CG; (b) an open state to expose at least one scent cartridge CG. The cover CV may comprise a mesh configured to conceal at least one scent cartridge CG and allow air to pass through the outlet OT. The cover CV may comprise the outlet OT. The cover CV may comprise a magnet configured to couple the cover CV and the enclosure EN. The component C/SD may comprise an inlet chamber. The inlet chamber may be separated from the outlet OT by the enclosure EN. The component C/SD may comprise a cover CV for at least one scent cartridge CG; the cover CV may be configured to form the outlet OT. The actuator AC may be positioned at an end of the inlet chamber. The component C/SD may comprise a fan FN. The fan FN may be configured to direct air (a) to the inlet chamber; (b) through scent media M of at least one scent cartridge CG; (c) through the outlet OT. The fan FN may be configured for at least one of (a) an off state; (b) an on state. The fan FN may be configured for (a) a high speed state; (b) a low speed state to provide (1) a high intensity scent dispersion; (2) a low intensity scent dispersion. The fan FN may be positioned at an end of the inlet chamber. The fan FN may comprise a first fan FN and a second fan FN. The fan FN may be configured for (1) a high intensity scent dispersion with the first fan FN on and the second fan FN on; (2) a low intensity scent dispersion with the first fan FN on and the second fan FN off. At least one scent cartridge CG may comprise a first scent cartridge, a second scent cartridge, a third scent cartridge and a fourth scent cartridge; the first fan FN may be configured to direct air through scent media M of the first scent cartridge and through scent media M of the second scent cartridge; the second fan FN may be configured to direct air through scent media M of the third scent cartridge and through scent media M of the fourth scent cartridge. The actuator AC may be configured to compress a spring of at least one scent cartridge CG to actuate at least one scent cartridge CG from the sealed state to the unsealed state to allow passage of air through the scent media M toward the outlet OT. The component C/SD may comprise at least one of: (a) a console; (b) an overhead console; (c) a floor console; (d) a center console; (e) a cup holder; (f) a module SD configured to mount within a cupholder.

According to an exemplary embodiment as shown schematically, a system for a vehicle interior may comprise a component C/SD configured to dispense scent from scent media M contained in at least one cartridge CG into air in a vehicle interior comprising: an inlet IN; an outlet OT; an enclosure EN configured for at least one cartridge CG providing scent media M; an actuator AC configured to actuate at least one cartridge CG between a sealed state and an unsealed state; and a user interface UI. See e.g. FIGS. 4, 5A, 11A-11D, 19A-19B, 21A-21C, 22D, 23A-23C, 25A-25C, 27A-27B, 30A-30B, 36A-36C, 37A-37C, 38A-38B, 39A-39D, 41A-41D, 43A-43D and 45A-45D. The user interface UI may be configured to facilitate the selection of scent by selection of at least one cartridge CG for actuation. The user interface UI may be configured for selection of intensity of scent from at least one cartridge CG. See FIG. 46.

According to an exemplary embodiment as shown schematically, a vehicle interior component C/SD may comprise an apparatus SD configured to dispense scent from scent media M contained in at least one cartridge CG into air in a vehicle interior comprising: an inlet IN; an outlet OT; a chamber configured for at least one scent cartridge CG providing scent media M; and an actuator AC configured to actuate at least one cartridge CG between a sealed state and an unsealed state. The scent may be dispensed from the outlet OT by selection of at least one cartridge CG.

According to an exemplary embodiment as shown schematically, a vehicle interior component C may comprise a module SD configured to dispense scent from scent media M contained in at least one interchangeable cartridge CG into air in a vehicle interior comprising: an enclosure EN configured for at least one interchangeable scent-dispensing cartridge comprising scent media M; an actuator AC configured to actuate at least one cartridge CG to dispense scent; and an interface between at least one cartridge CG and the enclosure EN. The chamber may be configured so that at least one cartridge CG can be removed and replaced with at least one cartridge CG. The interface may comprise at least one of a data/network interface and a mechanical interface. See also FIGS. 22D and 45A-45D.

According to an exemplary embodiment as shown schematically, a system for a vehicle interior may comprise a component C/SD configured to dispense scent from scent media M contained in at least one cartridge CG into air in a vehicle interior comprising: an inlet IN; an outlet OT; an enclosure EN configured for at least one cartridge CG providing scent media M; a valve mechanism V/VM configured to actuate at least one cartridge CG between a sealed state and an unsealed state; and a user interface UI. The user interface UI may be configured to facilitate the selection of scent by selection of at least one cartridge CG for actuation.

According to an exemplary embodiment as shown schematically, a vehicle interior component C/SD may comprise an apparatus SD configured to dispense scent from scent media M contained in at least one cartridge CG into air in a vehicle interior comprising: an inlet IN; an outlet OT; a chamber configured for at least one scent cartridge CG providing scent media M; and a valve mechanism V/VM configured to actuate at least one cartridge CG between a sealed state and an unsealed state. The scent may be dispensed from the outlet OT by selection of at least one cartridge CG. See e.g. FIGS. 5A-5B and 45A-45D.

According to an exemplary embodiment as shown schematically, a vehicle interior component C may comprise a module SD configured to dispense scent from scent media M contained in at least one interchangeable cartridge CG into air in a vehicle interior comprising: an enclosure EN configured for at least one interchangeable scent-dispensing cartridge comprising scent media M; a valve mechanism V/VM configured to actuate at least one cartridge CG to dispense scent; and an interface between at least one cartridge CG and the enclosure EN. See e.g. FIGS. 4, 5A, 11A-11D, 19A-19B, 21A-21C, 22D, 23A-23C, 25A-25C, 27A-27B, 30A-30B, 36A-36C, 37A-37C, 38A-38B, 39A-39D, 41A-41D, 43A-43D and 45A-45D. The chamber may be configured so that at least one cartridge CG can be removed and replaced with at least one cartridge CG; the interface may comprise at least one of a data/network interface DI and a mechanical interface MI. See FIGS. 22D and 45A-45D. The valve mechanism V/VM may comprise an actuator AC. The valve mechanism V/VM may be configured to be operated by a power supply PS. The interface may comprise a user interface UI for a vehicle component C/SD. The valve mechanism V/VM may be configured to be operated by the user interface UI. According to an exemplary embodiment, the valve mechanism may comprise a valve arrangement (e.g. a flow control element with one or more valves, seals, etc.).

Exemplary Embodiments—System/Method of Operation

According to an exemplary embodiment as shown schematically in FIGS. 2, 4, 5A-5B, 27A-27B, 38A-38B, 45A-45D and 46, a vehicle interior I may comprise a system comprising a component C providing a scent-dispensing module SD comprising an inlet IN and an outlet OT and configured to dispense scent from a set of cartridges/cartridge system CG containing scent media M through actuation of a mechanism/interface. See also FIGS. 6A, 7A, 8A-8B, 10A-10D, 16A-16B, 23A-23C and 25A-25C. As indicated schematically, the module SD may be configured to contain at least one cartridge CG comprising scent media M so that the scent from the scent media M is dispensed at the outlet OT of the module SD into the vehicle interior. See FIGS. 2, 3, 5A-5B, 27A-27B, 28A-28C, 34A-34D, 38A-38B and 45A-45D. As indicated in FIGS. 4, 5A-5B, 27A-27B, 38A-38B and 45A-45D, the system/module may comprise an actuator/actuation mechanism configured to actuate a valve mechanism VM (e.g. at least one flow control element such as a valve V or seal) between the inlet IN and the outlet OT; the actuator/actuation mechanism may be configured to actuate the valve mechanism selectively through a user interface UI. See also FIG. 46.

As shown schematically in FIGS. 45A-45D, the system/module SD may be configured for connection to a network system that may comprise a vehicle network, intranet/network, local area network, cloud network, etc.; the system/module may comprise a fan FN and power source/supply and a control system/controller with interface for operation (e.g. operation of the actuator, valve mechanism/valve VM/V, fan, etc.). As indicated in FIGS. 45C-45D, in operation of system/module SD (e.g. under operation of control system/interface by user interface to select cartridge CG an operate fan FN, actuator, valve mechanism, etc.) scent SN from scent media M in a selected cartridge CG when actuated from a sealed state to an unsealed state is dispensed by air flow from inlet IN into cartridge CG across scent media M and from cartridge CG and to outlet OT of the system/module SD.

Figure 46:
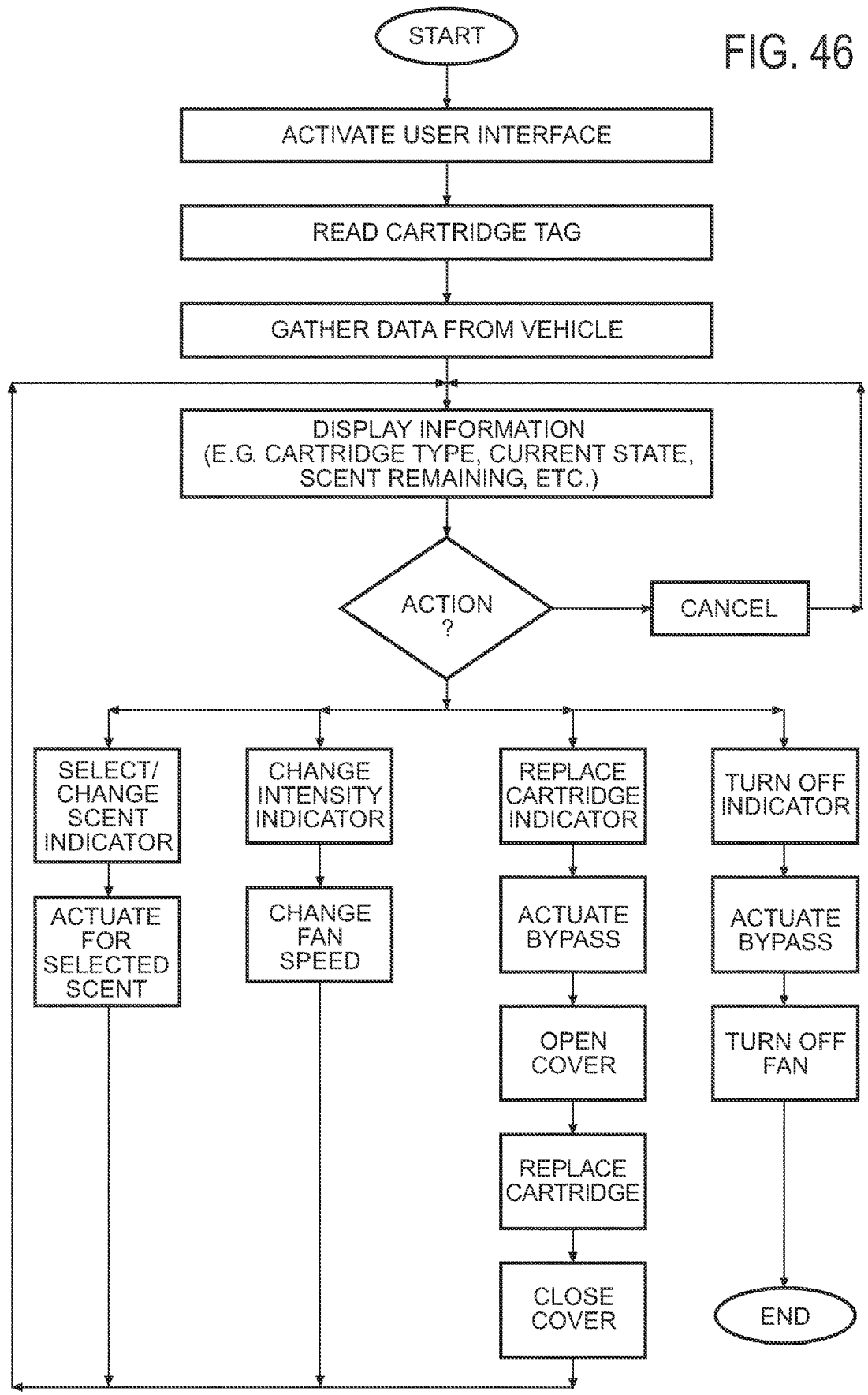
FIG. 46 is a schematic flow diagram of operation of a component/apparatus for dispensing scent according to an exemplary embodiment.

As indicated schematically according to an exemplary embodiment in FIG. 46, the operation of the system/module for dispensing scent into a vehicle interior may comprise the steps of activating the user interface and reading the data/information tag of each cartridge and gathering data (including from the vehicle and connected networks); information may be displayed for/through a user interface/display (e.g. cartridge type/scent, state/status of cartridges and module, remaining scent/life of scent media contained in a cartridge, etc.); actions may be initiated at the user interface/control including changing of scent (e.g. selection of cartridges, selectively sealing/unsealing, actuation of valve, etc.), changing of intensity of scent (e.g. actuation of control system, fan speed, valve mechanism), replacement of cartridge (actuation/bypass, open cover, replace and close cover) and turning the module on/off (e.g. actuation, bypass, turn fan off, turn module off, etc.). According to an exemplary embodiment, the system/module may be operated by any of a wide variety of control programs including but not limited to local/vehicle control and network control and/or data interchange.

It is important to note that the present inventions (e.g. inventive concepts, etc.) have been described in the specification and/or illustrated in the FIGURES of the present patent document according to exemplary embodiments; the embodiments of the present inventions are presented by way of example only and are not intended as a limitation on the scope of the present inventions. The construction and/or arrangement of the elements of the inventive concepts embodied in the present inventions as described in the specification and/or illustrated in the FIGURES is illustrative only. Although exemplary embodiments of the present inventions have been described in detail in the present patent document, a person of ordinary skill in the art will readily appreciate that equivalents, modifications, variations, etc. of the subject matter of the exemplary embodiments and alternative embodiments are possible and contemplated as being within the scope of the present inventions; all such subject matter (e.g. modifications, variations, embodiments, combinations, equivalents, etc.) is intended to be included within the scope of the present inventions. It should also be noted that various/other modifications, variations, substitutions, equivalents, changes, omissions, etc. may be made in the configuration and/or arrangement of the exemplary embodiments (e.g. in concept, design, structure, apparatus, form, assembly, construction, means, function, system, process/method, steps, sequence of process/method steps, operation, operating conditions, performance, materials, composition, combination, etc.) without departing from the scope of the present inventions; all such subject matter (e.g. modifications, variations, embodiments, combinations, equivalents, etc.) is intended to be included within the scope of the present inventions. The scope of the present inventions is not intended to be limited to the subject matter (e.g. details, structure, functions, materials, acts, steps, sequence, system, result, etc.) described in the specification and/or illustrated in the FIGURES of the present patent document. It is contemplated that the claims of the present patent document will be construed properly to cover the complete scope of the subject matter of the present inventions (e.g. including any and all such modifications, variations, embodiments, combinations, equivalents, etc.); it is to be understood that the terminology used in the present patent document is for the purpose of providing a description of the subject matter of the exemplary embodiments rather than as a limitation on the scope of the present inventions.

It is also important to note that according to exemplary embodiments the present inventions may comprise conventional technology (e.g. as implemented and/or integrated in exemplary embodiments, modifications, variations, combinations, equivalents, etc.) or may comprise any other applicable technology (present and/or future) with suitability and/or capability to perform the functions and processes/operations described in the specification and/or illustrated in the FIGURES. All such technology (e.g. as implemented in embodiments, modifications, variations, combinations, equivalents, etc.) is considered to be within the scope of the present inventions of the present patent document.

The invention claimed is:

1. A component for a vehicle interior configured to dispense scent from at least one scent-dispensing cartridge containing scent media into air in the vehicle interior comprising:
   a scent-dispensing apparatus comprising a module providing an inlet and an outlet;
   a latch configured to retain the at least one scent-dispensing cartridge for use in the module; and
   a plunger comprising a spring-actuated plunger configured to present the at least one scent-dispensing cartridge to facilitate removal from the module;
   wherein the module comprises an enclosure configured for the at least one scent-dispensing cartridge providing the scent media;
   wherein the module comprises an actuator comprising an arm configured to actuate the at least one scent-dispensing cartridge between a sealed state and an unsealed state;
   wherein the at least one scent-dispensing cartridge comprises a first scent-dispensing cartridge and a second scent-dispensing cartridge;
   wherein the actuator comprises a motor configured to pull the arm toward the motor to actuate the first scent-dispensing cartridge and to push the arm to actuate the second scent-dispensing cartridge;
   wherein the latch is configured to provide the scent-dispensing cartridge with a latched state for use in the enclosure of the module and an unlatched state for removal from the enclosure of the module facilitated by the plunger;
   wherein the spring-actuated plunger comprises a spring configured to present the at least one scent-dispensing cartridge to facilitate removal from the module for replacement in response to movement of the latch.

2. The component of claim 1 wherein the scent media comprises first scent media in the first scent-dispensing cartridge and second scent media in the second scent-dispensing cartridge.

3. The component of claim 2 wherein the actuator is configured to provide the scent-dispensing apparatus with (a) a bypass state with the first scent-dispensing cartridge in a sealed state and the second scent-dispensing cartridge in a sealed state; (b) a first actuation state actuating the first scent-dispensing cartridge in an unsealed state with the second scent-dispensing cartridge in the sealed state; (c) a second actuation state actuating the second scent-dispensing cartridge in an unsealed state with the first scent-dispensing cartridge in the sealed state.

4. The component of claim 3 wherein the actuator comprises an actuation mechanism comprising a cam mechanism; wherein the cam mechanism comprises a slider comprising (a) a cam for the first scent-dispensing cartridge; (b) a cam for the second scent-dispensing cartridge.

5. The component of claim 4 wherein the actuation mechanism comprises a cam shaft configured to (a) actuate the first scent-dispensing cartridge from the sealed state to the unsealed state to allow passage of air through the first scent media of the first scent-dispensing cartridge toward the outlet; (b) actuate the second scent-dispensing cartridge from the sealed state to the unsealed state to allow passage of air through the second scent media of the second scent-dispensing cartridge toward the outlet.

6. The component of claim 5 wherein the cam shaft is configured (a) to provide the bypass state; (b) to provide the first actuation state; (c) to provide the second actuation state.

7. The component of claim 2 wherein the latch comprises a spring-actuated latch configured for (a) the latched state to secure the first scent-dispensing cartridge; (b) the unlatched state to present the first scent-dispensing cartridge for replacement.

8. The component of claim 7 wherein the spring of the plunger is configured to apply force to pivot the first scent-dispensing cartridge at least partially out of the enclosure of the module to present the first scent-dispensing cartridge for replacement in response to movement of the latch for the first scent-dispensing cartridge from the latched state to the unlatched state.

9. The component of claim 4 wherein the actuation mechanism comprises (a) a first cam-follower arrangement to operate a first valve arrangement for the first scent-dispensing cartridge; (b) a second cam-follower arrangement to operate a second valve arrangement for the second scent-dispensing cartridge;
   wherein the first cam-follower arrangement comprises a first cam on the slider and a first follower; wherein the second cam-follower arrangement comprises a second cam on the slider and a second follower.

10. A component for a vehicle interior configured to dispense scent from scent media into air in the vehicle interior comprising:
   a scent-dispensing apparatus comprising a module providing an inlet and an outlet;
   wherein the module comprises an enclosure configured for at least one scent-dispensing cartridge providing the scent media;
   wherein the at least one scent-dispensing cartridge comprises a first scent-dispensing cartridge and a second scent-dispensing cartridge;
   wherein the module comprises an actuator configured (a) to actuate the at least one scent-dispensing cartridge between a sealed state and an unsealed state and (b) to move the at least one scent-dispensing cartridge from the enclosure to facilitate removal from the module;
   wherein the module comprises a cover configured for (a) a closed state to conceal the at least one scent-dispensing cartridge and (b) an open state to expose the at least one scent-dispensing cartridge;

wherein the cover comprises an outlet for the at least one scent-dispensing cartridge and a cover structure for the at least one scent-dispensing cartridge configured to form an outlet chamber for the at least one scent-dispensing cartridge.

11. The component of claim 10 wherein when the cover is in the open state the actuator is configured for (a) a first accessible state actuating the first scent-dispensing cartridge in an accessible position for replacement with the second scent-dispensing cartridge in the inaccessible position; (b) a second accessible state actuating the second scent-dispensing cartridge in an accessible position for replacement with the first scent-dispensing cartridge in the inaccessible position.

12. The component of claim 10 wherein the apparatus comprises an inlet duct to the inlet and an outlet duct to the outlet; wherein the inlet duct is separated from the outlet duct within the module of the apparatus.

13. The component of claim 10 further comprising a fan configured to provide air flow between the inlet and the outlet.

14. The component of claim 13 further comprising a bypass duct; wherein the fan is configured to direct air (a) to the inlet; (b) through the bypass duct; (c) through the outlet.

15. The component of claim 13 wherein the fan is configured for a high speed state and a low speed state; wherein the high speed state is configured to provide high intensity scent dispersion; wherein the low speed state is configured to provide low intensity scent dispersion.

16. The component of claim 10 wherein the actuator comprises a cam mechanism configured to (a) rotate in a first direction to actuate the first scent-dispensing cartridge and (b) rotate in a second direction generally opposite the first direction to actuate the second scent-dispensing cartridge.

17. A component for a vehicle interior configured to dispense scent from a cartridge system comprising at least one scent-dispensing cartridge providing a scent media into air in the vehicle interior comprising:
 a scent-dispensing apparatus comprising a module providing an inlet and an outlet;
 wherein the module comprises an enclosure configured for the cartridge system comprising the at least one scent-dispensing cartridge providing the scent media;
 wherein the module comprises an actuator for a valve assembly configured to actuate the at least one scent-dispensing cartridge between a sealed state and an unsealed state;
 wherein the at least one scent-dispensing cartridge comprises a body comprising an inlet port and an outlet port and a chamber configured to contain the scent media;
 wherein the valve assembly comprises a flow control element configured to facilitate air flow for the at least one scent-dispensing cartridge;
 wherein the flow control element of the valve assembly is configured to control the air flow for the at least one scent-dispensing cartridge into the inlet port across the scent media in the chamber and from the outlet port; so that the flow control element when open is configured to facilitate the air flow across the scent media in the chamber of the body and when closed is configured to provide a seal of the air flow to the scent media in the chamber of the body;
 wherein the actuator comprises a cam mechanism comprising a slider configured to selectively open and close the flow control element for the at least one scent-dispensing cartridge;
 wherein the slider comprises a cam configured to actuate a follower to open the flow control element to facilitate air flow for the at least one scent-dispensing cartridge.

18. The component of claim 17 wherein the actuator is configured to compress a spring of the at least one scent-dispensing cartridge to actuate the at least one scent-dispensing cartridge from the sealed state to the unsealed state to allow the air flow through the scent media toward the outlet.

19. The component of claim 17 wherein the actuator comprises an actuation mechanism comprising a shaft; wherein the shaft is configured to actuate the at least one scent-dispensing cartridge.

20. The component of claim 17 wherein the flow control element comprises a valve; wherein the cam mechanism is configured to open the air flow by the valve for the unsealed state and to close the air flow by the valve for the sealed state.

* * * * *

UNITED STATES PATENT AND TRADEMARK OFFICE
CERTIFICATE OF CORRECTION

PATENT NO. : 11,679,648 B2
APPLICATION NO. : 17/463496
DATED : June 20, 2023
INVENTOR(S) : Michael Robert Catlin et al.

Page 1 of 1

It is certified that error appears in the above-identified patent and that said Letters Patent is hereby corrected as shown below:

On the Title Page

Item (30) add the following:
Foreign Application Priority Data
Feb. 20, 2020 (CN) 2020201896737

Signed and Sealed this
Twenty-fourth Day of September, 2024

Katherine Kelly Vidal
*Director of the United States Patent and Trademark Office*